US007592324B2

(12) United States Patent
Shepard et al.

(10) Patent No.: US 7,592,324 B2
(45) Date of Patent: Sep. 22, 2009

(54) RNAI-MEDIATED INHIBITION OF OCULAR TARGETS

(75) Inventors: Allan R. Shepard, Fort Worth, TX (US); Jon E. Chatterton, Crowley, TX (US); Abbot F. Clark, Arlington, TX (US); Martin B. Wax, Westlake, TX (US)

(73) Assignee: Alcon, Inc., Hunenberg (CH)

( * ) Notice: Subject to any disclaimer, the term of this patent is extended or adjusted under 35 U.S.C. 154(b) by 165 days.

(21) Appl. No.: 11/345,361

(22) Filed: Feb. 1, 2006

(65) Prior Publication Data

US 2006/0172965 A1    Aug. 3, 2006

Related U.S. Application Data

(60) Provisional application No. 60/648,926, filed on Feb. 1, 2005, provisional application No. 60/753,364, filed on Dec. 22, 2005.

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl. ................ 514/44; 435/6; 435/320.1; 435/375; 536/23.1; 536/24.1; 536/24.5

(58) Field of Classification Search ............... None
See application file for complete search history.

(56) References Cited

U.S. PATENT DOCUMENTS

| | | | |
|---|---|---|---|
| 6,326,193 | B1 | 12/2001 | Liu et al. |
| 6,506,559 | B1 | 1/2003 | Fire et al. |
| 7,022,828 | B2 | 4/2006 | McSwiggen |
| 2002/0086356 | A1 | 7/2002 | Tuschl et al. |
| 2002/0114784 | A1* | 8/2002 | Li et al. ............... 424/93.2 |
| 2002/0162126 | A1 | 10/2002 | Beach et al. |
| 2003/0027783 | A1 | 2/2003 | Zernicka-Goetz et al. |
| 2003/0153524 | A1 | 8/2003 | Hinton et al. |
| 2004/0053411 | A1 | 3/2004 | Cullen et al. |
| 2004/0147475 | A1 | 7/2004 | Li et al. |
| 2004/0175732 | A1 | 9/2004 | Rana |
| 2004/0203145 | A1 | 10/2004 | Zamore et al. |
| 2004/0259247 | A1* | 12/2004 | Tuschl et al. ............ 435/375 |
| 2005/0203043 | A1 | 9/2005 | Fedorov et al. |
| 2005/0223427 | A1 | 10/2005 | Leake et al. |
| 2005/0245475 | A1* | 11/2005 | Khvorova et al. ............ 514/44 |
| 2005/0246794 | A1 | 11/2005 | Khvorova et al. |
| 2005/0255487 | A1 | 11/2005 | Khvorova et al. |
| 2006/0058266 | A1* | 3/2006 | Manoharan et al. ............ 514/81 |

FOREIGN PATENT DOCUMENTS

| | | |
|---|---|---|
| CA | 2359180 | 7/2001 |
| WO | WO 00/44895 | 8/2000 |
| WO | WO 01/36646 A1 | 5/2001 |
| WO | WO 01/68836 A2 | 9/2001 |
| WO | 0210449 | 2/2002 |
| WO | WO 02/44321 A3 | 6/2002 |
| WO | 03087367 | 10/2003 |
| WO | 2004020583 | 3/2004 |
| WO | 2004022750 | 3/2004 |
| WO | WO 2004/022782 A2 | 3/2004 |
| WO | 2004042024 | 5/2004 |
| WO | WO 2005/079815 A2 | 9/2005 |
| WO | 2006021817 | 3/2006 |
| WO | WO 2006/021817 A2 | 3/2006 |

OTHER PUBLICATIONS

Ambros, "The functions of animal microRNAs", *Nature*, pp. 350-355, vol. 431, Sep. 16, 2004, © 2004, Nature Publishing Group.
Bartel, "MicroRNAs: Genomics, Biogenesis, Mechanism, and Function", *Cell*, pp. 281-297, vol. 116, Jan. 23, 2004, © 2004, Cell Press.
Dorsett, et al., "SiRNAs: Applications in Functional Genomics and Potential as Therapeutics", *Nature*, pp. 318-329, vol. 3, Apr. 2004, © 2004, Nature Publishing Group.
Echeverri, et al., "siRNA Design: It's All in the Algorithm", *Ambion TechNotes*, pp. 1-6, vol. 11:3, http://www.ambion.com/techlib/tn/113/14. html, 2006.
Elbashir, et al., "Duplexes of 21—nucleotide RNAs Mediate RNA Interference in Cultured Mammalian Cells", *Letters to Nature*, pp. 494-498, vol. 411, May 24, 2001, © 2001, McMillan Magazines Ltd.
Elbashir, et al., "Functional Anatomy of siRNAs for Mediating Efficient RNAi in *Drosophila melanogaster* embryo lysate", *The EMBO Journal*, pp. 6877-6888, vol. 20, No. 23, 2001, © European Molecular Biology Organization.
Elbashir, et al., "RNA interference is mediated by 21- and 22-nucleotide RNAs", *Genes & Development*, pp. 188-200, vol. 15, © 2001 Cold Spring Harbor Laboratory Press, ISSN 0890-9369/01.
Elbashir, et al., "Analysis of gene function in somatic mammalian cells uisng small interfering RNAs", *Methods*, pp. 199-213, vol. 26, © 2002 Elsevier Science (USA).
Hannon, et al., "Unlocking the potential of the human genome with RNA interference", *Nature*, pp. 371-378, vol. 431, Sep. 16, 2004, © 2004, Nature Publishing Group.
He, et al., "MicroRNAs: Small RNAs With A Big Role In Gene Regulation", *Reviews*, pp. 522-531, vol. 5, Jul. 2004, www.nature.com/reviews/genetics.
Jackson, et al., "Expression Profiling Reveals Off-Target Gene Regulation by RNAi", *Nature Biotechnology*, pp. 635-638, vol. 21, No. 6, Jun. 2003, © 2003, Nature Publishing Group.
Kawasaki, et al., "Induction of DNA methylation and gene silencing by short interfering RNAs in human cells", *Nature*, pp. 211-217, vol. 431, Sep. 9, 2004, © 2004, Nature Publishing Group.
Lim, et al., "Vertebrate MicroRNA Genes", *Science*, pp. 1540, vol. 299, Mar. 7, 2003, www.sciencemag.org.

(Continued)

*Primary Examiner*—Sean R McGarry
(74) *Attorney, Agent, or Firm*—Jason J. Derry

(57) ABSTRACT

RNA interference is provided for inhibition of ocular hypertension target mRNA expression for lowering elevated intraocular pressure in patients with open-angle glaucoma or ocular hypertension. Ocular hypertension targets include carbonic anhydrase II, IV, and XII; β1- and β2 adrenergic receptors; acetylcholinesterase; $Na^+/K^+$-ATPase; and Na—K-2Cl cotransporter. Ocular hypertension is treated by administering interfering RNAs of the present invention.

37 Claims, 1 Drawing Sheet

OTHER PUBLICATIONS

Liu, et al., "Argonaute2 is the Catalytic Engine of Mammalian RNAi", *Science*, pp. 1437-1441, vol. 305, Sep. 3, 2004, www.sciencemag.org.

Morris, et al., "Small Interfering RNA-Induced Transcriptional Gene Silencing in Human Cells", *Science*, pp. 1289-1292, vol. 305, Aug. 27, 2004, www.sciencemag.org.

Novina, et al., "The RNAi revolution", *Nature*, pp. 161-164, vol. 430, Jul. 8, 2004, © 2004, Nature Publishing Group.

Paddison, et al., "Short hairpin RNAs (shRNAs) induce sequence-specific silencing in mammalian cells", *Genes & Development*, pp. 948-958, vol. 16, © 2002, Cold Spring Harbor Laboratory Press, ISSN 0890-9369/02.

Pang, et al., "Preliminary characterization of a transformed cell strain derived from human trabecular meshwork", *Current Eye Research*, pp. 51-63, vol. 13, No. 1, 1994, © Oxford University Press.

"psiRNA System A simple and innovative tool to create Short Hairpin SiRNAs" Small Interfering RNAs (siRNA): psiRNA System, pp. 1-3, http://www.invivogen.com/siRNA/psiRNA_system.htm, printed Nov. 3, 2004.

"RNAi Shows Cracks in Its Armor", *Science*, pp. 1124-1125, vol. 306, Nov. 12, 2004, www.sciencemag.org.

"Selection of siRNA duplexes from the target mRNA sequence", *The siRNA user guide* (revised May 6, 2004), pp. 1-7, Tuschi Lab, http://www.rockerfeller.edu/labheads/tuschl/sima.html plus one page of supplementary information.

Shepard, et al., "Importance of quantitative PCR primer location for short interfering RNA efficacy determination", *Analytical Biochemistry*, pp. 287-288, vol. 344, © 2005, Elsevier Inc.

"siRNA Design Guidelines", Ambion Technical Bulletin #506, pp. 1-8, © 2004, Ambion, Inc. http://www.ambion.com/techlib/tb/tb_506.html.

"Small Interfering RNAs (siRNA) A revolution in functional genomics", Small Interfering RNAs (siRNA): Overview, pp. 1-3, http://www.invivogen.com/siRNA/siRNA_overview.htm, printed Nov. 3, 2004.

Soutschek, et al., "Therapeutic silencing of an endogenous gene by systemic administration of modified SiRNAs", *Nature*, pp. 173-178, vol. 432, Nov. 11, 2004, © 2004, Nature Publishing Group.

Zhou, et al., "Inhibition of HIV-1 Fusion With Small Interfering RNAs Targeting The Chemokine Coreceptor CXCR4", *Gene Therapy*, pp. 1703-1712, vol. 11, Aug. 12, 2004, © 2004 Nature Publishing Group.

U.S. Appl. No. 11/313,200 entitled "RNAi Inhibition of CTGF For Treatment of Ocular Disorder," Shepard et al., filed Dec. 20, 2006, (34576.39).

U.S. Appl. No. 11/313,210 entitled "RNAi Inhibition of Serum Amyloid A For Treatment Of Glaucoma," Clark et al., filed Dec. 19, 2004, (34576.43).

U.S. Appl. No. 11/373,376 entitled "RNAi-Mediated Inhibition of Frizzled Related Protein-1 For Treatment of Glaucoma," Clark et al., filed Mar. 10, 2006.

U.S. Appl. No. 11/344,702 entitled "RNAi-Mediated Inhibition of Ocular Hypertension Targets" Shepard et al. filed Feb. 1, 2006.

NCBI Sequence NM_000067, "*Homo sapiens* carbonic anhydrase II (CA2) mRNA." pp. 1-5, http://www.ncbi.nlm.nih.gov, printed Jan. 14, 2005.

NCBI Sequence M77181, "*H. sapiens* carbonic anhydrase II (CAII) gene, exon 7, and complete cds." pp. 1, 2, http://www.ncbi.nlm.nih.gov, printed Apr. 6, 2006.

NCBI Sequence X03251, "Human gene fragment for carbonic anhydrase II (exons 1 and 2)." pp. 1, 2, http://www.ncbi.nlm.nih.gov, printed Apr. 6, 2006.

NCBI Sequence BC011949, "*Homo sapiens* carbonic anhydrase II, mRNA (cDNa clone MGC:9006 IMAGE:3863603), complete cds." pp. 1.3, http://www.ncbi.nlm.nih.gov, printed Apr. 6, 2006.

NCBI Sequence BC035424, "*Homo sapiens* carbonic anhydrase II, mRNA (cDNA clone IMAGE:3860618)." pp. 1-3, http://www.ncbi.nlm.nih.gov, printed Apr. 6, 2006.

NCBI Sequence CR536526, "*Homo sapiens* full open reading frame cDNA clone RZPDo834C0222D for gene CA2, cargonic anhydrase II; complete cds, incl. stopcodon." pp. 1, 2, http://www.ncbi.nlm.nih.gov, printed Apr. 6, 2006.

NCBI Sequence CR541875, "*Homo sapiens* full open reading frame cDNA Clone RZPDo834B0233D for gene CA2, carbonic anhydrase II; complete cds, without stopcodon." pp. 1, 2, http://www.ncbi.nlm.nih.gov, printed Apr. 6, 2006.

NCBI Sequence J03037, "Human carbonic anhydrase II mRNA, Complete cds." pp. 1, 2, http://www.ncbi.nlm.nih.gov, printed Apr. 6, 2006.

NCBI Sequence M36532, "Human carbonic anhydrase II mRNA, complete cds." pp. 1, 2, http://www.ncbi.nlm.nih.gov, printed Apr. 6, 2006.

NCBI Sequence S69526, "carbonic anhydrase II {clone pDRM12, exon 7} [human, leukocytes, mRNA Partial, 54 nt]." pp. 1, 2, http://www.ncbi.nlm.nih.gov, printed Apr. 6, 2006.

NCBI Sequence Y00339, "Human mRNA for carbonic anhydrase II {EC 4.2.1.1}.", pp. 1, 2, http://www.ncbi.nlm.nih.gov, printed Apr. 6, 2006.

NCBI Sequence $NM_{13}$ 000717, "*Homo sapiens* carbonic anhydrase IV (CA4), mRNA." pp. 1-5, http://www.ncbi.nlm.nih.gov, printed Apr. 6, 2006.

NCBI Sequence L10955, "Human carbonic anhydrase IV gene, exon 7." pp. 1, 2, http://www.ncbi.nlm.nih.gov, printed Apr. 6, 2006.

NCBI Sequence BC057792, "*Homo sapiens* carbonic anhydrase IV, mRNA (cDNA clone MGC:71638 IMAGE:30331755), complete cds." pp. 1-3, http://www.ncbi.nlm.nih.gov, printed Apr. 6, 2006.

NCBI Sequence BC069649, "*Homo sapiens* carbonic anhydrase IV, mRNA (cDNA clone MGC:97195 IMAGE:7262441), complete cds." pp. 1-3, http://www.ncbi.nlm.nih.gov, printed Apr. 6, 2006.

NCBI Sequence BC074768, "*Homo sapiens* ADP-ribosylarginine hydrolase, mRNA (cDNA clone MGC:103809 IMAGE:30915190), complete cds." pp. 1-3, http://www.ncbi.nlm.nih.gov, printed Apr. 6, 2006.

NCBI Sequence CR541766, "*Homo sapiens* full open reading frame cDNA clone RZPDo834A0430D for gene CA4, carbonic anhydrase IV; complete cds, incl. stopcodon." pp. 1, 2, http://www.ncbi.nlm.nih.gov, printed Apr. 6, 2006.

NCBI Sequence M83670, "Human carbonic anhydrase IV mRNA, complete cds." pp. 1, 2, http://www.ncbi.nlm.nih.gov, printed Apr. 6, 2006.

NCBI Sequence NM_001218, "*Homo sapiens* carbonic anhydrase XII (CA12), transcript variant 1, mRNA." http://www.ncbi.nlm.nih.gov, printed Apr. 6, 2006.

NCBI Sequence NM_206925, "*Homo sapiens* carbonic anhydrase XII (CA12), transcript variant 2, mRNA." http://www.ncbi.nlm.nih.gov, printed Apr. 6, 2006.

Herkel U et al: "Update on Topical Carbonic Anhydrase Inhibitors"; Current Opinion In Opthalmology, Philadelphia, PA, US; vol. 12, No. 2; Apr. 2001; pp. 88-93.

Mallory Julia C et al: "A novel group of genes regulates susceptibility to antineoplastic drugs in highly tumorigenic breast cancer cells." Molecular Pharmacology, vol. 68, No. 6; Dec. 2005; pp. 1747-1756.

Campochiaro P A: "Potential applications for RNAi to probe pathogenesis and develop new treatments for ocular disorders." Gene Therapy; vol. 13, No. 6; Sep. 2005; pp. 559-562.

Fuchshofer R et al: "Transforming growth factor-beta 2 modulated extracellular matrix component expression in cultured human optic nerve head astrocytes." Investigative Ophthalmology & Visual Science, Association for Research in Vision; vol. 46, No. 2; Feb. 2005; pp. 568-578.

Pastorekova Silvia et al: "Carbonic anhydrases: current state of the art, therapeutic applications and future prospects." Journal of Enzyme Inhibition and Medicinal Chemistry; vol. 19, No. 3; Jun. 2004; pp. 199-229.

Sly W S et al: "Human Carbonic Anhydrase and Carbonic Anhydrase Deficiencies"; Annual Review of Biochemistry, Palto Alto, CA, US; vol. 64, 1995; pp. 375-401.

Liao S-Y et al: "Expression of cell surface transmembrane carbonic anhydrase genes CA9 and CA12 in the human eye: glaucoma." Journal of Mecial Genetics; vol. 40, No. 4; Apr. 2003; pp. 257-261.

Croci S et al: "Inhibition of connective tissue growth factor (CTGF/CCN2) expression decreases the survival and myogenic differentiation of human rhabdomyosarcoma cells." Cancer Research, American Association for Cancer Research, Baltimore, MD, US; vol. 64, No. 5; Mar. 2004; pp. 1730-1736.

Nakamura Hiroshi et al: "RNA interference targeting transforming growth factor-beta type II receptor suppresses ocular inflammation and fibrosis." Molecular Vision [Electronic Resource]; vol. 10; Oct. 2004; pp. 703-711.

Anonymous: "Matched siRNAs and assays." TechNotes 11(4), Ambion Inc. [online]; vol. 11, No. 4; Jul. 2004; Retrieved from the Internet @ http://www.ambion.com/techlib/tn/114/4.html.

Anonymous: "CA12, human, RegSeq Accession NM_001218"; Abmion Inc. [online]; Retrieved from the Internet @ URL: http://www.ambion.com/catalog/sirna_search.php?num=20&page=1&BInFTVars=gi.name%2Cgi.full_name&BInFT=carbonic+anhydrase+XII&BInFTMod=c_all_p&t.primary_idnetifier=&t.primary_identifierMod=str_eq&other_gene_name=&other_gene-Nam.

* cited by examiner

SEQUENCE LISTING

<160> NUMBER OF SEQ ID NOS: 724

<210> SEQ ID NO 1
<211> LENGTH: 1551
<212> TYPE: DNA
<213> ORGANISM: Homo sapiens

<400> SEQUENCE: 1

```
ggcgcccaag ccgccgccgc cagatcggtg ccgattcctg ccctgccccg accgccagcg      60
cgaccatgtc ccatcactgg gggtacggca aacacaacgg acctgagcac tggcataagg     120
acttccccat tgccaaggga gagcgccagt ccctgttga catcgacact catacagcca      180
agtatgaccc ttccctgaag cccctgtctg tttcctatga tcaagcaact tccctgagga     240
tcctcaacaa tggtcatgct ttcaacgtgg agtttgatga ctctcaggac aaagcagtgc     300
tcaagggagg accctggat ggcacttaca gattgattca gtttcacttt cactggggtt      360
cacttgatgg acaaggttca gagcatactg tggataaaaa gaaatatgct gcagaacttc     420
acttggttca ctggaacacc aaatatgggg attttgggaa agctgtgcag caacctgatg     480
gactggccgt tctaggtatt tttttgaagg ttggcagcgc taaaccgggc cttcagaaag     540
ttgttgatgt gctggattcc attaaaacaa agggcaagag tgctgacttc actaacttcg     600
atcctcgtgg cctccttcct gaatccctgg attactggac ctacccaggc tcactgacca     660
ccctcctct tctggaatgt gtgacctgga ttgtgctcaa ggaacccatc agcgtcagca     720
gcgagcaggt gttgaaattc cgtaaactta acttcaatgg ggagggtgaa cccgaagaac     780
tgatggtgga caactggcgc ccagctcagc cactgaagaa caggcaaatc aaagcttcct     840
tcaaataaga tggtcccata gtctgtatcc aaataatgaa tcttcgggtg tttcccttta     900
gctaagcaca gatctacctt ggtgatttgg accctggttg ctttgtgtct agttttctag     960
acccttcatc tcttacttga tagacttact aataaaatgt gaagactaga ccaattgtca    1020
tgcttgacac aactgctgtg gctggttggt gctttgttta tggtagtagt ttttctgtaa    1080
cacagaatat aggataagaa ataagaataa agtaccttga ctttgttcac agcatgtagg    1140
gtgatgagca ctcacaattg ttgactaaaa tgctgctttt aaaacatagg aaagtagaat    1200
ggttgagtgc aaatccatag cacaagataa attgagctag ttaaggcaaa tcaggtaaaa    1260
tagtcatgat tctatgtaat gtaaaccaga aaaataaat gttcatgatt tcaagatgtt     1320
atattaaaga aaaactttaa aaattattat atatttatag caaagttatc ttaaatatga    1380
attctgttgt aatttaatga cttttgaatt acagagatat aaatgaagta ttatctgtaa    1440
aaaattgttat aattagagtt gtgatacaga gtatatttcc attcagacaa tatatcataa   1500
cttaataaat attgtatttt agatatattc tctaataaaa ttcagaattc t             1551
```

<210> SEQ ID NO 2
<211> LENGTH: 1104
<212> TYPE: DNA
<213> ORGANISM: Homo sapiens

<400> SEQUENCE: 2

```
ctcggtgcgc gaccccggct cagaggactc tttgctgtcc cgcaagatgc ggatgctgct      60
ggcgctcctg gccctctccg cggcgcggcc atcggccagt gcagagtcac actggtgcta    120
cgaggttcaa gccgagtcct ccaactaccc ctgcttggtg ccagtcaagt gggagaaa      180
ctgccagaag gaccgccagt ccccatcaa catcgtcacc accaaggcaa aggtggacaa    240
```

| | |
|---|---|
| aaaactggga cgcttcttct tctctggcta cgataagaag caaacgtgga ctgtccaaaa | 300 |
| taacgggcac tcagtgatga tgttgctgga gaacaaggcc agcatttctg gaggaggact | 360 |
| gcctgcccca taccaggcca aacagttgca cctgcactgg tccgacttgc catataaggg | 420 |
| ctcggagcac agcctcgatg gggagcactt tgccatggag atgcacatag tacatgagaa | 480 |
| agagaagggg acatcgagga atgtgaaaga ggcccaggac cctgaagacg aaattgcggt | 540 |
| gctggccttt ctggtggagg ctggaaccca ggtgaacgag gcttccagc cactggtgga | 600 |
| ggcactgtct aatatcccca aacctgagat gagcactacg atggcagaga gcagcctgtt | 660 |
| ggacctgctc cccaaggagg agaaactgag gcactacttc cgctacctgg gctcactcac | 720 |
| cacaccgacc tgcgatgaga aggtcgtctg gactgtgttc cgggagccca ttcagcttca | 780 |
| cagagaacag atcctggcat tctctcagaa gctgtactac gacaaggaac agacagtgag | 840 |
| catgaaggac aatgtcaggc ccctgcagca gctggggcag cgcacggtga taaagtccgg | 900 |
| ggccccgggt cggccgctgc cctgggccct gcctgccctg ctgggcccca tgctggcctg | 960 |
| cctgctggcc ggcttcctgc gatgatggct cacttctgca cgcagcctct ctgttgcctc | 1020 |
| agctctccaa gttccaggct tccggtcctt agccttccca ggtgggactt taggcatgat | 1080 |
| taaaatatgg acatattttt ggag | 1104 |

<210> SEQ ID NO 3
<211> LENGTH: 1723
<212> TYPE: DNA
<213> ORGANISM: Homo sapiens

<400> SEQUENCE: 3

| | |
|---|---|
| tgctacccgc gcccgggctt ctggggtgtt ccccaaccac ggcccagccc tgccacaccc | 60 |
| cccgccccccg gcctccgcag ctcggcatgg gcgcggggt gctcgtcctg ggcgcctccg | 120 |
| agcccggtaa cctgtcgtcg gccgcaccgc tccccgacgg cgcggccacc gcggcgcggc | 180 |
| tgctggtgcc cgcgtcgccg cccgcctcgt tgctgcctcc cgccagcgaa agccccgagc | 240 |
| cgctgtctca gcagtggaca gcgggcatgg gtctgctgat ggcgctcatc gtgctgctca | 300 |
| tcgtggcggg caatgtgctg gtgatcgtgg ccatcgccaa gacgccgcgg ctgcagacgc | 360 |
| tcaccaacct cttcatcatg tccctggcca gcgccgacct ggtcatgggg ctgctggtgg | 420 |
| tgccgttcgg ggccaccatc gtggtgtggg gccgctggga gtacggctcc ttcttctgcg | 480 |
| agctgtggac ctcagtggac gtgctgtgcg tgacggccag catcgagacc ctgtgtgtca | 540 |
| ttgccctgga ccgctacctc gccatcacct cgcccttccg ctaccagagc ctgctgacgc | 600 |
| gcgcgcgggc gcggggcctc gtgtgcaccg tgtgggccat ctcggccctg gtgtccttcc | 660 |
| tgcccatcct catgcactgg tggcgggcgg agagcgacga ggcgcgccgc tgctacaacg | 720 |
| accccaagtg ctgcgacttc gtcaccaacc gggcctacgc catcgcctcg tccgtagtct | 780 |
| ccttctacgt gcccctgtgc atcatggcct tcgtgtacct gcgggtgttc cgcgaggccc | 840 |
| agaagcaggt gaagaagatc gacagctgcg agcgccgttt cctcggcggc cagcgcggc | 900 |
| cgccctcgcc ctcgccctcg cccgtccccg cgcccgcgcc gcgcccgga ccccgcgcc | 960 |
| ccgccgccgc cgccgccacc gcccgctggc caacgggcg tgcgggtaag cggcggccct | 1020 |
| cgcgcctcgt ggcctacgc gagcagaagg cgctcaagac gctgggcatc atcatgggcg | 1080 |
| tcttcacgct ctgctggctg cccttcttcc tggccaacgt ggtgaaggcc ttccaccgcg | 1140 |
| agctggtgcc cgaccgcctc ttcgtcttct caactggct gggctacgcc aactcggcct | 1200 |

| | | |
|---|---|---|
| tcaaccccat catctactgc cgcagccccg acttccgcaa ggccttccag ggactgctct | 1260 |
| gctgcgcgcg cagggctgcc cgccggcgcc acgcgaccca cggagaccgg ccgcgcgcct | 1320 |
| cgggctgtct ggcccggccc ggaccccgc catcgcccgg ggccgcctcg acgacgacg | 1380 |
| acgacgatgt cgtcggggcc acgccgcccg cgcgcctgct ggagccctgg gccggctgca | 1440 |
| acggcggggc ggcggcggac agcgactcga gcctggacga gccgtgccgc cccggcttcg | 1500 |
| cctcggaatc caaggtgtag ggcccggcgc ggggcgcgga ctccgggcac ggcttcccag | 1560 |
| gggaacgagg agatctgtgt ttacttaaga ccgatagcag gtgaactcga agcccacaat | 1620 |
| cctcgtctga atcatccgag gcaaagagaa aagccacgga ccgttgcaca aaaaggaaag | 1680 |
| tttgggaagg gatgggagag tggcttgctg atgttccttg ttg | 1723 |

<210> SEQ ID NO 4
<211> LENGTH: 2015
<212> TYPE: DNA
<213> ORGANISM: Homo sapiens

<400> SEQUENCE: 4

| | | |
|---|---|---|
| actgcgaagc ggcttcttca gagcacgggc tggaactggc aggcaccgcg agccctagc | 60 |
| acccgacaag ctgagtgtgc aggacgagtc cccaccacac ccacaccaca gccgctgaat | 120 |
| gaggcttcca ggcgtccgct cgcggcccgc agagccccgc cgtgggtccg cccgctgagg | 180 |
| cgcccccagc cagtgcgctt acctgccaga ctgcgcgcca tggggcaacc cgggaacggc | 240 |
| agcgccttct tgctggcacc caatagaagc catgcgccgg accacgacgt cacgcagcaa | 300 |
| agggacgagg tgtgggtggt gggcatgggc atcgtcatgt ctctcatcgt cctggccatc | 360 |
| gtgtttggca atgtgctggt catcacagcc attgccaagt tcgagcgtct gcagacggtc | 420 |
| accaactact tcatcacttc actggcctgt gctgatctgg tcatgggcct ggcagtggtg | 480 |
| ccctttgggg ccgcccatat tcttatgaaa atgtggactt ttggcaactt ctggtgcgag | 540 |
| ttttggactt ccattgatgt gctgtgcgtc acggccagca ttgagaccct gtgcgtgatc | 600 |
| gcagtggatc gctactttgc cattacttca ccctttcaagt accagagcct gctgaccaag | 660 |
| aataaggccc gggtgatcat tctgatggtg tggattgtgt caggccttac ctccttcttg | 720 |
| cccattcaga tgcactggta ccgggccacc caccaggaag ccatcaactg ctatgccaat | 780 |
| gagacctgct gtgacttctt cacgaaccaa gcctatgcca ttgcctcttc catcgtgtcc | 840 |
| ttctacgttc ccctggtgat catggtcttc gtctactcca gggtcttca ggaggccaaa | 900 |
| aggcagctcc agaagattga caaatctgag ggccgcttcc atgtccagaa ccttagccag | 960 |
| gtggagcagg atgggcggac ggggcatgga ctccgcagat cttccaagtt ctgcttgaag | 1020 |
| gagcacaaag ccctcaagac gttaggcatc atcatgggca ctttcaccct ctgctggctg | 1080 |
| cccttcttca tcgttaacat tgtgcatgtg atccaggata acctcatccg taaggaagtt | 1140 |
| tacatcctcc taaattggat aggctatgtc aattctggtt tcaatcccct tatctactgc | 1200 |
| cggagcccag atttcaggat tgccttccag gagcttctgt gcctgcgcag gtcttctttg | 1260 |
| aaggcctatg gaatggcta ctccagcaac ggcaacacag gggagcagag tggatatcac | 1320 |
| gtggaacagg agaaagaaaa taaactgctg tgtgaagacc tcccaggcac ggaagacttt | 1380 |
| gtgggccatc aaggtactgt gcctagcgat aacattgatt cacaagggag gaattgtagt | 1440 |
| acaaatgact cactgctgta aagcagtttt tctactttta aagaccccc cccccccaac | 1500 |
| agaacactaa acagactatt taacttgagg gtaataaaact tagaataaaa ttgtaaaaat | 1560 |
| tgtatagaga tatgcagaag gaagggcatc cttctgcctt tttatttttt ttaagctgta | 1620 |

| | |
|---|---|
| aaaagagaga aaacttattt gagtgattat ttgttatttg tacagttcag ttcctctttg | 1680 |
| catggaattt gtaagtttat gtctaaagag ctttagtcct agaggacctg agtctgctat | 1740 |
| attttcatga cttttccatg tatctacctc actattcaag tattagggt aatatattgc | 1800 |
| tgctggtaat ttgtatctga aggagatttt ccttcctaca cccttggact tgaggatttt | 1860 |
| gagtatctcg gacctttcag ctgtgaacat ggactcttcc cccactcctc ttatttgctc | 1920 |
| acacggggta ttttaggcag ggatttgagg agcagcttca gttgttttcc cgagcaaagg | 1980 |
| tctaaagttt acagtaaata aaatgtttga ccatg | 2015 |

<210> SEQ ID NO 5
<211> LENGTH: 2909
<212> TYPE: DNA
<213> ORGANISM: Homo sapiens

<400> SEQUENCE: 5

| | |
|---|---|
| cagcctgcgc cggggaacat cggccgcctc cagctcccgg cgcggccgg cccggcccgg | 60 |
| ctcggccgcc tcagacgccg cctgccctgc agccatgagg cccccgcagt gtctgctgca | 120 |
| cacgccttcc ctggcttccc cactccttct cctcctcctc tggctcctgg gtggaggagt | 180 |
| gggggctgag ggccgggagg atgcagagct gctggtgacg gtgcgtgggg gccggctgcg | 240 |
| gggcattcgc ctgaagaccc cgggggccc tgtctctgct ttcctgggca tcccttttgc | 300 |
| ggagccaccc atgggacccc gtcgcttttct gccaccggag cccaagcagc cttggtcagg | 360 |
| ggtggtagac gctacaacct tccagagtgt ctgctaccaa tatgtggaca ccctataccc | 420 |
| aggttttgag ggcaccgaga tgtggaaccc caaccgtgag ctgagcgagg actgcctgta | 480 |
| cctcaacgtg tggacaccat accccggcc tacatccccc accctgtcc tcgtctggat | 540 |
| ctatgggggt ggcttctaca gtgggcctc ctccttggac gtgtacgatg ccgcttctt | 600 |
| ggtacaggcc gagaggactg tgctggtgtc catgaactac cgggtgggag cctttggctt | 660 |
| cctggccctg ccggggagcc gagaggcccc gggcaatgtg gtctcctgg atcagaggct | 720 |
| ggccctgcag tgggtgcagg agaacgtggc agccttcggg gtgacccga catcagtgac | 780 |
| gctgtttggg gagagcgcgg gagccgcctc ggtgggcatg cacctgctgt ccccgcccag | 840 |
| ccggggcctt ttccacaggg ccgtgctgca gagcggtgcc cccaatggac cctgggccac | 900 |
| ggtgggcatg ggagaggccc gtcgcagggc cacgcagctg gcccaccttg tgggctgtcc | 960 |
| tccaggcggc actggtggga atgacacaga gctggtagcc tgccttcgga cacgaccagc | 1020 |
| gcaggtcctg gtgaaccacg aatggcacgt gctgcctcaa gaaagcgtct tccggttctc | 1080 |
| cttcgtgcct gtggtagatg agacttcct cagtgacacc ccagaggccc tcatcaacgc | 1140 |
| gggagacttc cacggcctgc aggtgctggt gggtgtggtg aaggatgagg ctcgtatttt | 1200 |
| tctggtttac ggggccccag gcttcagcaa agacaacgag tctctcatca gccgggccga | 1260 |
| gttcctggcc ggggtgcggg tcggggttcc ccaggtaagt gacctggcag ccgaggctgt | 1320 |
| ggtcctgcat tacacagact ggctgcatcc cgaggacccg gcacgcctga gggaggccct | 1380 |
| gagcgatgtg gtgggcgacc acaatgtcgt gtgccccgtg gccagctggc tgggcgact | 1440 |
| ggctgcccag ggtgcccggg tctacgccta cgtctttgaa caccgtgctt ccacgctctc | 1500 |
| ctggccctg tggatggggg tgccccacgg ctacgagatc gagttcatct ttgggatccc | 1560 |
| cctggaccc tctcgaaact acacggcaga ggagaaaatc ttcgcccagc gactgatgcg | 1620 |
| atactgggcc aactttgccc gcacagggga tcccaatgag ccccgagacc caaggccccc | 1680 |

```
acaatggccc ccgtacacgg cgggggctca gcagtacgtt agtctggacc tgcggccgct    1740
ggaggtgcgg cggggggctgc gcgcccaggc ctgcgccttc tggaaccgct tcctcccaa    1800 attgctcagc gccaccgcct cggaggctcc cagcacctgc ccaggcttca cccatgggga    1860
ggctgctccg aggcccggcc tcccctgcc cctcctcctc ctccaccagc ttctcctcct     1920
cttcctctcc cacctccggc ggctgtgaac acggcctctt cccctacggc cacaggggcc    1980
cctcctctaa tgagtggtcg gaccgtgggg aagggcccca ctcagggatc tcagacctag    2040
tgctcccttc ctcctcaaac cgagagactc acactggaca gggcaggagg aggggccgt     2100 gcctcccacc cttctcaggg accccacgc ctttgttgtt tgaatggaaa tggaaaagcc     2160
agtattcttt tataaaatta tcttttggaa cctgagcctg acattgggg gaagtgggag     2220 gccccggacg gggtagcacc cccccattggg gctataacgg tcaaccattt ctgtctcttc   2280 ttttttccccc aacctccccc tcctgtcccc tctgttcccg tcttccggtc attcttttct   2340
cctcctctct ccttcctgct gtccttctcc ggccccgcct ctgccctcat cctccctctc    2400
gtctttcgca cattctcctg atcctcttgc caccgtccca cgtggtcgcc tgcatttctc    2460
cgtgcgtcct ccctgcactg aaacccccc ttcaacccgc ccaaatgtcc gatccccgac     2520
cttcctcgtg ccgtcctccc ctcccgcctc gctgggcgcc ctggccgcag acacgctcga    2580
cgaggcggag cgccagtgga aggccgagtt ccaccgctgg agctcctaca tggtgcactg    2640
gaagaaccag ttcgaccact acagcaagca ggatcgctgc tcagacctgt gaccccggcg    2700 ggaccccccat gtcctccgct ccgccggcc cctagctgt atatactatt tatttcaggg     2760
ctgggctata acacagacga gccccagact ctgcccatcc ccaccccacc ccgacgtccc    2820
ccggggctcc cggtcctctg gcatgtcttc aggctgagct cctccccgcg tgccttcgcc    2880
ctctggctgc aaataaactg ttacaggcc                                      2909

<210> SEQ ID NO 6
<211> LENGTH: 5468
<212> TYPE: DNA
<213> ORGANISM: Homo sapiens

<400> SEQUENCE: 6
tctctgtctg ccagggtctc cgactgtccc agacgggctg gtgtgggctt gggatcctcc      60
tggtgacctc tcccgctaag gtccctcagc cactctgccc caagatgggc cgtggggctg    120
gccgtgagta ctcacctgcc gccaccacgg cagagaatgg gggcggcaag aagaaacaga    180
aggagaagga actggatgag ctgaagaagg aggtggcaat ggatgaccac aagctgtcct    240
tggatgagct gggccgcaaa taccaagtgg acctgtccaa gggcctcacc aaccagcggg    300
ctcaggacgt tctggctcga gatgggccca acgccctcac accacctccc acaaccctg     360 agtgggtcaa gttctgccgt cagcttttcg gggggttctc catcctgctg tggattgggg    420
ctatcctctg cttcctggcc tacggcatcc aggctgccat ggaggatgaa ccatccaacg    480
acaatctata tctgggtgtg gtgctggcag ctgtggtcat tgtcactggc tgcttctcct    540
actaccagga ggccaagagc tccaagatca tggattcctt caagaacatg gtacctcagc    600
aagcccttgt gatccgggag ggagagaaga tgcagatcaa cgcagaggaa gtggtggtgg    660
gagacctggt ggaggtgaag ggtggagacc gcgtccctgc tgacctccgg atcatctctt    720
ctcatggctg taaggtggat aactcatcct taacaggaga gtcggagccc cagacccgct    780
cccccgagtt caccatgag aaccccctgg agaccgcaa tatctgtttc ttctccacca    840
actgtgttga aggcactgcc aggggcattg tgattgccac aggagaccgg acggtgatgg    900
```

```
gccgcatagc tactctcgcc tcaggcctgg aggttgggcg gacacccata gcaatggaga    960
ttgaacactt catccagctg atcacagggg tcgctgtatt cctgggggtc tccttcttcg   1020
tgctctccct catcctgggc tacagctggc tggaggcagt catcttcctc atcggcatca   1080
tagtggccaa cgtgcctgag gggcttctgg ccactgtcac tgtgtgcctg accctgacag   1140
ccaagcgcat ggcacggaag aactgcctgg tgaagaacct ggaggcgtg gagacgctgg    1200
gctccacgtc caccatctgc tcggacaaga cgggcaccct cacccagaac cgcatgaccg   1260
tcgcccacat gtggttcgac aaccaaatcc atgaggctga caccaccgaa gatcagtctg   1320
gggccacttt tgacaaacga tccctacgt ggacggccct gtctcgaatt gctggtctct    1380
gcaaccgcgc cgtcttcaag gcaggacagg agaacatctc cgtgtctaag cgggacacag   1440
ctggtgatgc ctctgagtca gctctgctca agtgcattga gctctcctgt ggctcagtga   1500
ggaaaatgag agacagaaac cccaaggtgg cagagattcc tttcaactct accaacaagt   1560
accagctgtc tatccacgag cgagaagaca gcccccagag ccacgtgctg gtgatgaagg   1620
gggcccagga gcgcattctg gaccggtgct ccaccatcct ggtgcagggc aaggagatcc   1680
cgctcgacaa ggagatgcaa gatgcctttc aaaatgccta catggagctg ggggacttg    1740
gggagcgtgt gctgggattc tgtcaactga atctgccatc tggaaagttt cctcggggct   1800
tcaaattcga cacggatgag ctgaacttc ccacggagaa gctttgcttt gtggggctca    1860
tgtctatgat tgaccctccc cgggctgctg tgccagatgc tgtgggcaag tgccgaagcg   1920
caggcatcaa ggtgatcatg gtaaccgggg atcaccctat cacagccaag gccattgcca   1980
aaggcgtggg catcatatca gagggtaacg agactgtgga ggacattgca gcccggctca   2040
acattcccat gagtcaagtc aaccccgag aagccaaggc atgcgtggtg cacggctctg    2100
acctgaagga catgacatcg gagcagctcg atgagatcct caagaaccac acagagatcg   2160
tctttgctcg aacgtctccc cagcagaagc tcatcattgt ggagggatgt cagaggcagg   2220
gagccattgt ggccgtgacg ggtgacgggg tgaacgactc ccctgcattg aagaaggctg   2280
acattggcat tgccatgggc atctctggct ctgacgtctc taagcaggca gccgacatga   2340
tcctgctgga tgacaacttt gcctccatcg tcacgggggt ggaggagggc cgcctgatct   2400
ttgacaactt gaagaaatcc atcgcctaca ccctgaccag caacatcccc gagatcaccc   2460
ccttcctgct gttcatcatt gccaacatcc ccctacctct gggcactgtg accatcctt    2520
gcattgacct gggcacagat atggtccctg ccatctcctt ggcctatgag gcagctgaga   2580
gtgatatcat gaagcggcag ccacgaaact cccagacgga caagctggtg aatgagaggc   2640
tcatcagcat ggcctacgga cagatcggga tgatccaggc actgggtggc ttcttcacct   2700
actttgtgat cctggcagag aacggtttcc tgccatcacg gctactggga atccgcctcg   2760
actgggatga ccgaccatg aatgatctgg aggacagcta tggacaggag tggacctatg    2820
agcagcggaa ggtggtggag ttcacgtgcc acacggcatt ctttgccagc atcgtggtgg   2880
tgcagtgggc tgacctcatc atctgcaaga cccgccgcaa ctcagtcttc cagcagggca   2940
tgaagaacaa gatcctgatt ttgggctcc tggaggagac ggcgttggct gcctttctct    3000
cttactgccc aggcatgggt gtagcccctcc gcatgtaccc gctcaaagtc acctggtggt   3060
tctgcgcctt cccctacagc ctcctcatct tcatctatga tgaggtccga aagctcatcc   3120
tgcgcggta tcctggtggc tgggtggaga aggagacata ctactgaccc cattggaaga   3180
agaaccaggc atggaaagat ggggagctct ggaggtgttg tggggatggt gatggagagg   3240
```

-continued

```
gatggaaata acgggtggca ttgggtggca acatttgggg agagataatg aggcaactca    3300
gcaggctaag ttgcgtggta tataaattgg ggtgatgacc ccatagacct aactgtgaac    3360
aatcagatta gacactatgt gttagagtcc ccccgaccag atccttttcc atcccactcc    3420
actatgttgt ctatttttc tgaggaatta agggttaccc caccctgccc actcccatcc    3480
cttcaacccc acttcctact gtaatagatc agcatccaaa agcaggaacc catctaaacc    3540
agaaggaagc cctctcagat caccccagcc tcactccatt tcccacttcc accccgtta    3600
gcttcctgca ggactctatc cctggcttcc ccttcagacc ttgcaatcac aaaaggttct    3660
tctggtgagt gcaagagcct gagactggaa aaggtggact tgtctcccag tcgaggctgg    3720
taagggacct tcaggagag ctgggcagac aggtgggaga tggaggtagg gctggctgga    3780
ggaaggaaac aacaaaggaa gtgaggtagt gccaatgaca ggacatttga catgagtctc    3840
cagatagatg tcgtggactc cagctctacg tcccacattt tagaataccc caccagcaga    3900
acaaactcag atctcatcag ggtagcagca gaggcaggac cagaaggcaa tcaagagctt    3960
ccagaaatgc cacacttgtg tgccacagag ttccccgctg acccttggtt aggggtcctc    4020
ttagtccaca aggtccggat gtcactcatg tacttaataa cacttcacct tctgtaatac    4080
taagtcctca gagctccatg ctgttctgaa agggatggcc acaagttctt tcccagcctc    4140
ttccattccc tttcttttca tgcccatccc gatgaacctg catcattccc cgacactgcc    4200
aagccaaccc tggaaaagga gttcgctggc cattggctag aatcagggtg gagaagttcc    4260
ctgaaccttc ctgtctccca gggacatgta tgcttccagg acaagctta ggtcatgaac    4320
atggtcagaa ccttttggaca agaggaaaaa tactaagaga tttgctttt ctgggtgcgg    4380
tggctcatgc ctgtaatccc agcactttgg gaggccgagg caggtggatc atgaggtcag    4440
gagttcgagg cgagcctggc caacatggtg aaaccctgtc tctactaaaa gtacaaaaaa    4500
ttagccagtc atggtggcac acgcctgtaa tctcagctac tcaggaggct gaggcaggag    4560
aattgcttga acctgtgagg aagaggttgc agtgagctga gatcgtgcca ttacactcca    4620
gcctgggcga aagggtgaga ctccatctca aaaaaaaaaa aaatgatttg cttttgacgt    4680
cttaggtggc agggctgttc cctccaggca aatgcccttc aaaccgacga tcattgtgcc    4740
cacttaccct gggctggaga gttggtttca ggttcctaca ggagatagct ttctttccct    4800
tactccctat ctaacacttt tgctctgcag gcagccttgc ccattctcta agcctggctt    4860
agaaggcact gggaatgtcc tgtagagaga gacctagata ggtcatgcaa gtgagaaaga    4920
catctgagga aaatgaaaga cctaaggcag acaggaagga agcacaaaag acaagcattg    4980
ggtcagaccc ataaccacc tcccaaaggc tgtcatttca ttgcactgga attttgcttt    5040
atcagaagca aggaagtaag ggagtcattg ccttgggcct gggaatctaa gtgggagaca    5100
atattaattt ggatccgatt aattggagat tactaactgt ggacaaaagt ttatctttgc    5160
acaatcaata aaaatggcat tttttagta aattaagagc ataaacaata ttgctagagg    5220
tggcatgttt agtctaccaa aaacaatact tttcaggcac tttagaaata tccttttaga    5280
agcagcgagt gcatgggcta attatcatca atctttatgt atttgttaaa gaaacatcta    5340
caggatcttt attggtgacc ttttgtaaga cattagtttg aggtactacc tatgtacttg    5400
aaaataataa agtggcattt ctttatgaaa aaaaaaaaa aaaaaaaaa aaaaaaaaa    5460
aaaaaaaa                                                            5468
```

<210> SEQ ID NO 7
<211> LENGTH: 3362

<212> TYPE: DNA
<213> ORGANISM: Homo sapiens

<400> SEQUENCE: 7

```
aaaaaatcaa ttttggaaga tgtcactgaa caactcttcc aatgtatttc tggattcagt      60
gcccagtaat accaatcgct ttcaagttag tgtcataaat gagaaccatg agagcagtgc     120
agctgcagat gacaatactg acccaccaca ttatgaagaa acctcttttg gggatgaagc     180
tcagaaaaga ctcagaatca gctttaggcc tgggaatcag gagtgctatg acaatttcct     240
ccacagtgga gaaactgcta aaacagatgc cagttttcac gcttatgatt ctcacacaaa     300
cacatactat ctacaaactt ttggccacaa caccatggat gccgttccca agatagagta     360
ctatcgtaac accggcagca tcagtgggcc caaggtcaac cgacccagcc tgcttgagat     420
tcacgagcaa ctcgcaaaga atgtggcagt caccccaagt tcagctgaca gagttgctaa     480
cggtgatggg atacctggag atgaacaagc tgaaaataag gaagatgatc aagctggtgt     540
tgtgaagttt ggatgggtga aggtgtgct ggtaagatgc atgctgaaca tctggggagt     600
catgctcttc attcgcctct cctggattgt tggagaagct ggaattggtc ttggagttat     660
catcattggc ctatccacca tagtaacgac aatcacaggt atgtccacgt ctgctattgc     720
cacgaacgga gttgttagag gaggtggggc ctactatctt atttccagaa gtttagggcc     780
cgagttcggt gggtcaatag gcctgatctt tgcttttgct aatgcagtgg ctgttgctat     840
gtatgtggtg ggattcgctg aaactgtagt agatctactt aaggagagtg attcgatgat     900
ggtggatcca accaatgaca tccggattat aggctccatc acagtggtga ttcttctagg     960
aatttcagta gctggaatgg aatgggaggc aaaggcccaa gtcattcttc tggtcattct    1020
tctaattgct attgcaaact tcttcattgg aactgtcatt ccatccaaca atgagaaaaa    1080
gtccagaggt ttctttaatt accaagcatc aatatttgca gaaaactttg gccacgctt    1140
cacaaagggt gaaggcttct ctctgtctt tgccattttt tcccagcag ctactgggat    1200
tcttgctggt gccaatatct caggagattt ggaggatccc caagatgcca tccccagagg    1260
aaccatgctg gccatttca tcaccactgt tgcctactta ggggttgcaa tttgtgtagg    1320
ggcctgtgtg gtccgagatg ccaccgggaa catgaatgac accatcattt ctgggatgaa    1380
ctgcaatggt tcagcagcat gtgggttggg ctatgacttc tcaagatgtc gacatgaacc    1440
atgtcagtac gggctgatga caatttcca ggtcatgagc atggtatcag gttcggccc    1500
cctcatcact gcgggaatct tttctgcaac actctcctcc gccctggcct cccttgtcag    1560
cgcacccaaa gtgttccagg ctctgtgcaa ggacaacatc tacaaagccc tgcagttttt    1620
tgcaaaggga tatgggaaaa acaatgaacc cctgagagga tatattctca ctttttctta t    1680
agccatggca tttattctta ttgcggaact gaacaccatt gctcccatca tctccaactt    1740
tttcctggcc tcatatgcac ttattaattt ctcctgcttc catgcctctt atgccaaatc    1800
tccaggatgg agacctgcgt atggaattta caacatgtgg gtatctcttt ttggagctgt    1860
tttgtgctgt gcagtcatgt ttgtcatcaa ctggtgggca gctgtcatca cctatgtcat    1920
tgaattcttc ctttacgtct atgtgacttg taagaagcca gatgtgaact ggggctcctc    1980
cacacaggct ctttcctacg tgagtgcttt agacaatgct ctggaattaa ccacagtgga    2040
agaccacgta aaaaacttca ggccccagtg cattgtctta acaggggac ccatgacaag    2100
acctgctctc ctggacataa ctcacgcctt taccaagaac agtggccttt gcatctgctg    2160
tgaagtcttt gtgggaccgc gcaaactgtg tgttaaggag atgaacagtg gcatggcgaa    2220
```

-continued

```
aaaacaggcc tggcttataa agaacaaaat caaggctttt tatgctgcag tggcggcaga    2280
ctgtttcagg gatggtgtcc gaagtcttct tcaggcctca ggcttaggaa gaatgaaacc    2340
aaacactctg gtgattggat ataagaaaaa ctggaggaaa gctcccttga cagagattga    2400
gaactacgtg ggaatcatac atgatgcatt tgattttgag attggcgtgg ttatagtcag    2460
aatcagccaa ggatttgaca tctctcaggt tcttcaggtg caagaggaat tagagagatt    2520
agaacaggag agactagcat tggaagcgac tatcaaagat aatgagtgtg aagaggaaag    2580
tggaggcatc cgaggcttgt ttaaaaaagc tggcaagttg aacattacta agacaacgcc    2640
taaaaaagat ggcagcatta acacaagcca gtcgatgcat gtgggagagt tcaaccagaa    2700
actggtggaa gccagcactc aatttaaaaa gaaacaagaa aaaggcacaa ttgatgtttg    2760
gtggttgttt gatgatggag ggttaacact tcttatcccc tatatcttaa ctctcagaaa    2820
aaaatggaaa gactgtaaat taagaatcta tgtgggaggg aagatcaacc gcattgaaga    2880
agaaaaaatt gcaatggctt cccttctgag caaatttagg ataaaatttg cagacatcca    2940
tatcatcggt gacatcaaca ttaggccaaa caaagagagc tggaaagtct ttgaagagat    3000
gattgaacca tatcgtctcc atgaaagctg caaagattta acaactgctg agaaattaaa    3060
aagagaaact ccgtggaaaa ttacagatgc agaactggaa gcagtcaagg aaaagagtta    3120
ccgccaagtt cgactgaatg aactcttaca ggagcactcc agagctgcta atctcattgt    3180
cctgagcctt cccgtggcaa gaaagggatc catatcggat ttgttgtata tggcttggtt    3240
ggaaatcctc acaaagaacc tcccacctgt cttactagtt agaggaaatc acaaaaatgt    3300
cttgacattt tactcttaaa acatgaaaga ttggaataca ttttaactta atgtaatgca    3360
ta                                                                  3362
```

<210> SEQ ID NO 8
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 8
ccctgaggat cctcaacaa                                                19

<210> SEQ ID NO 9
<211> LENGTH: 21
<212> TYPE: DNA
<213> ORGANISM: Artificial Sequence
<220> FEATURE:
<223> OTHER INFORMATION: SENSE STRAND
<220> FEATURE:
<221> NAME/KEY: misc_feature
<222> LOCATION: (20)..(21)
<223> OTHER INFORMATION: any, A, T/U, C, G

<400> SEQUENCE: 9
cccugaggau ccucaacaan n                                             21

<210> SEQ ID NO 10
<211> LENGTH: 21
<212> TYPE: DNA
<213> ORGANISM: Artificial Sequence
<220> FEATURE:
<223> OTHER INFORMATION: ANTISENSE STRAND
<220> FEATURE:
<221> NAME/KEY: misc_feature
<222> LOCATION: (20)..(21)
<223> OTHER INFORMATION: any, A, T/U, C, G

```
<400> SEQUENCE: 10
uuguugagga uccucagggn n                                          21

<210> SEQ ID NO 11
<211> LENGTH: 21
<212> TYPE: RNA
<213> ORGANISM: Artificial Sequence
<220> FEATURE:
<223> OTHER INFORMATION: SENSE STRAND

<400> SEQUENCE: 11
cccugaggau ccucaacaau u                                          21

<210> SEQ ID NO 12
<211> LENGTH: 21
<212> TYPE: RNA
<213> ORGANISM: Artificial Sequence
<220> FEATURE:
<223> OTHER INFORMATION: ANTISENSE STRAND

<400> SEQUENCE: 12
uuguugagga uccucagggu u                                          21

<210> SEQ ID NO 13
<211> LENGTH: 48
<212> TYPE: DNA
<213> ORGANISM: Artificial Sequence
<220> FEATURE:
<223> OTHER INFORMATION: HAIRPIN DUPLEX WITH LOOP
<220> FEATURE:
<221> NAME/KEY: misc_RNA
<222> LOCATION: (1)..(19)
<223> OTHER INFORMATION: RIBONUCLEOTIDES
<220> FEATURE:
<221> NAME/KEY: misc_feature
<222> LOCATION: (20)..(27)
<223> OTHER INFORMATION: ANY, A, T/U, C, G
<220> FEATURE:
<221> NAME/KEY: misc_feature
<222> LOCATION: (28)..(48)
<223> OTHER INFORMATION: RIBONUCLEOTIDES

<400> SEQUENCE: 13
cccugaggau ccucaacaan nnnnnnnuug uugaggaucc ucagggu              48

<210> SEQ ID NO 14
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 14
gggccttcag aaagttgtt                                             19

<210> SEQ ID NO 15
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 15
gcgagcaggt gttgaaatt                                             19

<210> SEQ ID NO 16
```

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 16
ggtgttgaaa ttccgtaaa                                              19

<210> SEQ ID NO 17
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 17
gccactgaag aacaggcaa                                              19

<210> SEQ ID NO 18
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 18
ccactgaaga acaggcaaa                                              19

<210> SEQ ID NO 19
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 19
cccatagtct gtatccaaa                                              19

<210> SEQ ID NO 20
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 20
ccatagtctg tatccaaat                                              19

<210> SEQ ID NO 21
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 21
ggtgatttgg accctggtt                                              19

<210> SEQ ID NO 22
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 22
```

```
gggtgatgag cactcacaa                                                    19
```

<210> SEQ ID NO 23
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 23

```
tcgtcaccac caaggcaaa                                                    19
```

<210> SEQ ID NO 24
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 24

```
gcttcttctt ctctggcta                                                    19
```

<210> SEQ ID NO 25
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 25

```
tcttctctgg ctacgataa                                                    19
```

<210> SEQ ID NO 26
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 26

```
ggctacgata agaagcaaa                                                    19
```

<210> SEQ ID NO 27
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 27

```
ggtccgactt gccatataa                                                    19
```

<210> SEQ ID NO 28
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 28

```
ggagatgcac atagtacat                                                    19
```

<210> SEQ ID NO 29
<211> LENGTH: 19
<212> TYPE: DNA

```
<213> ORGANISM: Artificial Sequence
<220> FEATURE:
<223> OTHER INFORMATION: TARGETING SEQUENCE

<400> SEQUENCE: 29
gcacatagta catgagaaa                                                    19

<210> SEQ ID NO 30
<211> LENGTH: 19
<212> TYPE: DNA
<213> ORGANISM: Artificial
<220> FEATURE:
<223> OTHER INFORMATION: TARGETING SEQUENCE

<400> SEQUENCE: 30
gacatcgagg aatgtgaaa                                                    19

<210> SEQ ID NO 31
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 31
ggtggaggca ctgtctaat                                                    19

<210> SEQ ID NO 32
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 32
gggactttag gcatgatta                                                    19

<210> SEQ ID NO 33
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 33
tccttcttct gcgagctgt                                                    19

<210> SEQ ID NO 34
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 34
tcgagaccct gtgtgtcat                                                    19

<210> SEQ ID NO 35
<211> LENGTH: 19
<212> TYPE: DNA
<213> ORGANISM: Artificial
<220> FEATURE:
<223> OTHER INFORMATION: TARGETING SEQUENCE

<400> SEQUENCE: 35
gcatcatggc cttcgtgta                                                    19
```

```
<210> SEQ ID NO 36
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 36
gaacgaggag atctgtgtt                                                    19

<210> SEQ ID NO 37
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 37
acgaggagat ctgtgttta                                                    19

<210> SEQ ID NO 38
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 38
ggagatctgt gtttactta                                                    19

<210> SEQ ID NO 39
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 39
gatagcaggt gaactcgaa                                                    19

<210> SEQ ID NO 40
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 40
cccacaatcc tcgtctgaa                                                    19

<210> SEQ ID NO 41
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 41
ccacaatcct cgtctgaat                                                    19

<210> SEQ ID NO 42
<211> LENGTH: 19
<212> TYPE: DNA
<213> ORGANISM: Artificial Sequence
<220> FEATURE:
```

```
<223> OTHER INFORMATION: TARGETING SEQUENCE

<400> SEQUENCE: 42
tctgaatcat ccgaggcaa                                              19

<210> SEQ ID NO 43
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 43
gcatcgtcat gtctctcat                                              19

<210> SEQ ID NO 44
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 44
gctggtcatc acagccatt                                              19

<210> SEQ ID NO 45
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 45
ccctcaagac gttaggcat                                              19

<210> SEQ ID NO 46
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 46
gcatcatcat gggcacttt                                              19

<210> SEQ ID NO 47
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 47
cctaaattgg ataggctat                                              19

<210> SEQ ID NO 48
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 48
gctatgtcaa ttctggttt                                              19
```

<210> SEQ ID NO 49
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 49
ggaagacttt gtgggccat                    19

<210> SEQ ID NO 50
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 50
gcctagcgat aacattgat                    19

<210> SEQ ID NO 51
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 51
gggaggaatt gtagtacaa                    19

<210> SEQ ID NO 52
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 52
gctgtgaaca tggactctt                    19

<210> SEQ ID NO 53
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 53
ccagagtgtc tgctaccaa                    19

<210> SEQ ID NO 54
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 54
gctaccaata tgtggacac                    19

<210> SEQ ID NO 55
<211> LENGTH: 19
<212> TYPE: DNA
<213> ORGANISM: Artificial Sequence
<220> FEATURE:
<223> OTHER INFORMATION: TARGETING SEQUENCE

```
<400> SEQUENCE: 55
ccaatatgtg gacaccta                                            19

<210> SEQ ID NO 56
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 56
gctggtgtcc atgaactac                                           19

<210> SEQ ID NO 57
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 57
tcatcaacgc gggagactt                                           19

<210> SEQ ID NO 58
<211> LENGTH: 19
<212> TYPE: DNA
<213> ORGANISM: Artificial
<220> FEATURE:
<223> OTHER INFORMATION: TARGETING SEQUENCE

<400> SEQUENCE: 58
ggtctacgcc tacgtcttt                                           19

<210> SEQ ID NO 59
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 59
gctacgagat cgagttcat                                           19

<210> SEQ ID NO 60
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 60
gctataacgg tcaaccatt                                           19

<210> SEQ ID NO 61
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 61
ggctgcaaat aaactgtta                                           19

<210> SEQ ID NO 62
<211> LENGTH: 19
```

```
<212> TYPE: DNA
<213> ORGANISM: Artificial Sequence
<220> FEATURE:
<223> OTHER INFORMATION: TARGETING SEQUENCE

<400> SEQUENCE: 62
gctgcaaata aactgttac                                           19

<210> SEQ ID NO 63
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 63
ccatccaacg acaatctat                                           19

<210> SEQ ID NO 64
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 64
gcatcatatc agagggtaa                                           19

<210> SEQ ID NO 65
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 65
cctcctcatc ttcatctat                                           19

<210> SEQ ID NO 66
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 66
ggaagtgagg tagtgccaa                                           19

<210> SEQ ID NO 67
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 67
ggatgtcact catgtactt                                           19

<210> SEQ ID NO 68
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 68
```
gctccatgct gttctgaaa         19

<210> SEQ ID NO 69
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 69
gctggccatt ggctagaat         19

<210> SEQ ID NO 70
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 70
ggtcagaacc tttggacaa         19

<210> SEQ ID NO 71
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 71
gctagaggtg gcatgttta         19

<210> SEQ ID NO 72
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 72
gcgagtgcat gggctaatt         19

<210> SEQ ID NO 73
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 73
ccaccatagt aacgacaat         19

<210> SEQ ID NO 74
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 74
ggaatggaat gggaggcaa         19

<210> SEQ ID NO 75
<211> LENGTH: 19
<212> TYPE: DNA
<213> ORGANISM: Artificial Sequence

```
<220> FEATURE:
<223> OTHER INFORMATION: TARGETING SEQUENCE

<400> SEQUENCE: 75
gggatgaact gcaatggtt                                                    19

<210> SEQ ID NO 76
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 76
ccatgcctct tatgccaaa                                                    19

<210> SEQ ID NO 77
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 77
cctgctctcc tggacataa                                                    19

<210> SEQ ID NO 78
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 78
gcatctgctg tgaagtctt                                                    19

<210> SEQ ID NO 79
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 79
gcctcaggct taggaagaa                                                    19

<210> SEQ ID NO 80
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 80
ggaagcgact atcaaagat                                                    19

<210> SEQ ID NO 81
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 81
gctggcaagt tgaacatta                                                    19
```

<210> SEQ ID NO 82
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 82
gcaagaaagg gatccatat                                                  19

<210> SEQ ID NO 83
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 83
gaaggttggc agcgctaaa                                                  19

<210> SEQ ID NO 84
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 84
atgtgctgga ttccattaa                                                  19

<210> SEQ ID NO 85
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 85
tgtgctggat tccattaaa                                                  19

<210> SEQ ID NO 86
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 86
ccgtaaactt aacttcaat                                                  19

<210> SEQ ID NO 87
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 87
gatctacctt ggtgatttg                                                  19

<210> SEQ ID NO 88
<211> LENGTH: 19
<212> TYPE: DNA
<213> ORGANISM: Artificial Sequence
<220> FEATURE:
<223> OTHER INFORMATION: TARGETING SEQUENCE

```
<400> SEQUENCE: 88
gaccaattgt catgcttga                                              19

<210> SEQ ID NO 89
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 89
ggtgatgagc actcacaat                                              19

<210> SEQ ID NO 90
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 90
cactcacaat tgttgacta                                              19

<210> SEQ ID NO 91
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 91
actcacaatt gttgactaa                                              19

<210> SEQ ID NO 92
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 92
ctcacaattg ttgactaaa                                              19

<210> SEQ ID NO 93
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 93
aggaaagtag aatggttga                                              19

<210> SEQ ID NO 94
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 94
gtagaatggt tgagtgcaa                                              19

<210> SEQ ID NO 95
```

<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 95
tagaatggtt gagtgcaaa                                            19

<210> SEQ ID NO 96
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 96
caagataaat tgagctagt                                            19

<210> SEQ ID NO 97
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 97
agttaaggca aatcaggta                                            19

<210> SEQ ID NO 98
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 98
gagttgtgat acagagtat                                            19

<210> SEQ ID NO 99
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 99
agttgtgata cagagtata                                            19

<210> SEQ ID NO 100
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 100
gttgtgatac agagtatat                                            19

<210> SEQ ID NO 101
<211> LENGTH: 3992
<212> TYPE: DNA
<213> ORGANISM: Homo sapiens

<400> SEQUENCE: 101
ataaaagctg cccggggaag ccaggagagc gaagggcgga cgtactcgcc acggcaccca     60

```
ggctgcgcgc acgcggtccc ggtgtgcagc tggagagcga gcggccaccg ggagccccg      120 gcacagcccg cgcccgcccc gcaggagccc gcgaagatgc cccggcgcag cctgcacgcg      180
gcggccgtgc tcctgctggt gatcttaaag gaacagcctt ccagcccggc cccagtgaac      240
ggttccaagt ggacttattt tggtcctgat ggggagaata gctggtccaa gaagtacccg      300
tcgtgtgggg gcctgctgca gtcccccata gacctgcaca gtgacatcct ccagtatgac      360
gccagcctca cgcccctcga gttccaaggc tacaatctgt ctgccaacaa gcagtttctc      420
ctgaccaaca atggccattc agtgaagctg aacctgccct cggacatgca catccagggc      480
ctccagtctc gctacagtgc cacgcagctg cacctgcact gggggaaccc gaatgacccg      540
cacggctctg agcacaccgt cagcggacag cacttcgccg ccgagctgca cattgtccat      600
tataactcag acctttatcc tgacgccagc actgccagca caagtcaga aggcctcgct      660 gtcctggctg ttctcattga gatgggctcc ttcaatccgt cctatgacaa gatcttcagt      720
caccttcaac atgtaaagta caaggccag gaagcattcg tcccgggatt caacattgaa      780
gagctgcttc cggagaggac cgctgaatat taccgctacc gggggtccct gaccacaccc      840
ccttgcaacc ccactgtgct ctggacagtt ttccgaaacc ccgtgcaaat tcccaggag      900 cagctgctgg ctttggagac agccctgtac tgcacacaca tggacgaccc ttcccccaga      960
gaaatgatca acaacttccg gcaggtccag aagttcgatg agaggctggt atacacctcc     1020
ttctcccaag tgcaagtctg tactgcggca ggactgagtc tgggcatcat cctctcactg     1080
gccctggctg gcattcttgg catctgtatt gtggtggtgg tgtccatttg gcttttcaga     1140
aggaagagta tcaaaaaagg tgataacaag ggagtcattt acaagccagc caccaagatg     1200
gagactgagg cccacgcttg aggtccccgg agctcccggg cacatccagg aaggaccttg     1260
ctttggaccc tacacacttc ggctctctgg acacttgcga cacctcaagg tgttctctgt     1320
agctcaatct gcaaacatgc caggcctcag ggatcctctg ctgggtgcct ccttgccttg     1380
ggaccatggc cacccagag ccatccgatc gatggatggg atgcactctc agaccaagca     1440
gcaggaattc aaaagctgctt gctgtaactg tgtgagattg tgaagtggtc tgaattctgg     1500
aatcacaaac caagccatgc tggtgggcca ttaatggttg gaaaacactt tcatccgggg     1560
ctttgccaga gcgtgctttc aagtgtcctg gaaattctgc tgcttctcca agctttcaga     1620
caagaatgtg cactctctgc ttaggttttg cttgggaaac tcaacttctt tcctctggag     1680
acggggcatc tccctctgat ttccttctgc tatgacaaaa cctttaatct gcaccttaca     1740
actcggggac aaatggggac aggaaggatc aagttgtaga gagaaaaaga aaacaagaga     1800
tatacattgt gatatattag ggacactttc acagtcctgt cctctggatc acagacactg     1860
cacagacctt agggaatggc aggttcaagt tccacttctt ggtggggatg agaagggaga     1920
gagagctaga gggacaaaga gaatgagaag acatggatga tctgggagag tctcactttg     1980
gaatcagaat tggaatcaca ttctgtttat caagccataa tgtaaggaca gaataataca     2040
atattaagtc caaatccaac ctcctgtcag tggagcagtt atgttttata ctctacagat     2100
tttacaaata atgaggctgt tccttgaaaa tgtgttgttg ctgtgtcctg gaggagacat     2160
gagttccgag atgacccaat ctgcctttga atctggagga aataggcaga aacaaaatga     2220
ctgtagaact tattctctgt aggccaaatt tcatttcagc cacttctgca ggatccctac     2280
tgccaacctg gaatggagac ttttatctac ttctctctct ctgaagatgt caaatcgtgg     2340
tttagatcaa atatatttca agctataaaa gcaggaggtt atctgtgcag ggggctggca     2400
```

-continued

```
tcatgtattt aggggcaagt aataatggaa tgctactaag atactccata ttcttccccg    2460
aatcacacag acagtttctg acaggcgcaa ctcctccatt ttcctcccgc aggtgagaac    2520
cctgtggaga tgagtcagtg ccatgactga aaggaaccg accccctagtt gagagcacct    2580 tgcagttccc cgagaacttt ctgattcaca gtctcatttt gacagcatga aatgtcctct    2640
tgaagcatag cttttaaat atctttttcc ttctactcct ccctctgact ctaagaattc     2700
tctcttctgg aatcgcttga acccaggagg cggaggttgc agtaagccaa ggtcatgcca    2760
ctgcactcta gcctgggtga cagagcgaga ctccatctca aaaaaaaaaa aaaaaaaatt    2820
attctgtacc atcacaactt ttcacaacga tggcaagcct tatgtcttgg gagcctgttt    2880
tgctaggcaa agttacaagt gacctaatgg gagctcaaat gtgtgtgtgt ctctctgtgt    2940
gtttgtgtgt gtgtgtgcac tcaagacctc taacagcctc gaagcctggg gtggcatccc    3000
ggccttgcca ttagcatgcc tcatgcatca tcagatgaca aggacaaccc tcatgacgaa    3060
gcaacatgaa ttaggggggcc tcttggcctt ggtccaaaat tgtcaatcag aaatgaacat   3120
aaaggactcc agagcagtgg gactgtctgt caaaagactc tgtatatctt ttgtggatga    3180
gttttgtgag agaacagaga gaccattgta cctggcacaa gggctgttca tgaaaaggga   3240
gacttactgg gaggtgcaag acagtggcat ttctcctctc ctcttgctgc tcagcacagc    3300
cctggattgc agccccgagg ctgagaccag acaaagcccg ggaggcagaa agatgctcca    3360
agaaccaaca ctatcaatgt ctttgcaaat cctcacagga ttcctgtggg tccagctttg    3420
gaactgggaa acctttcttc ggatccgcac tcattccact gatgccagct gccccctgaag  3480 gatgccagta ctgtggtgtg tgagtctcag cagccgccca cacgctccta actctgctgc    3540
atggcagatg cctaggtgga aatagcaaaa acaaggccca ggctggggcc agggccagag    3600
gggaaggccc tggattctca ctcatgtgag atcttgaatc tctttctttg ttctgtttgt    3660
ttagttagta tcatctggta aaatagttaa aaaacaacaa aaaactctgt atctgtttct    3720
agcatgtgct gcattgactc tattaatcac atttcaaatt caccctacat tcctctcctc    3780
ttcactagcc tctctgaagg tgtcctggcc agccctggag aagcactggt gtctgcagca    3840
cccctcagtt cctgtgcctc agcccacagg ccactgtgat aatggtctgt ttagcacttc    3900
tgtatttatt gtaagaatga ttataatgaa gatacacact gtaactacaa gaaattataa    3960
atgttttcca catcaaaaaa aaaaaaaaaa aa                                   3992
```

<210> SEQ ID NO 102
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 102
tcctgctggt gatcttaaa                                                    19

<210> SEQ ID NO 103
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 103
acggttccaa gtggactta                                                    19

```
<210> SEQ ID NO 104
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 104
gagaatagct ggtccaaga                                               19

<210> SEQ ID NO 105
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 105
agaatagctg gtccaagaa                                               19

<210> SEQ ID NO 106
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 106
gtgacatcct ccagtatga                                               19

<210> SEQ ID NO 107
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 107
gctacaatct gtctgccaa                                               19

<210> SEQ ID NO 108
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 108
cagtttctcc tgaccaaca                                               19

<210> SEQ ID NO 109
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 109
agtttctcct gaccaacaa                                               19

<210> SEQ ID NO 110
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 110
gaccaacaat ggccattca                                               19

<210> SEQ ID NO 111
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 111
ctccttcaat ccgtcctat                                               19

<210> SEQ ID NO 112
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 112
ccttcaatcc gtcctatga                                               19

<210> SEQ ID NO 113
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 113
atccgtccta tgacaagat                                               19

<210> SEQ ID NO 114
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 114
agatcttcag tcaccttca                                               19

<210> SEQ ID NO 115
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 115
cggagaggac cgctgaata                                               19

<210> SEQ ID NO 116
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 116
ggagaggacc gctgaatat                                               19

<210> SEQ ID NO 117
<211> LENGTH: 19
```

```
<212> TYPE: DNA
<213> ORGANISM: Artificial Sequence
<220> FEATURE:
<223> OTHER INFORMATION: TARGETING SEQUENCE

<400> SEQUENCE: 117
agaggaccgc tgaatatta                                               19

<210> SEQ ID NO 118
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 118
aggtccagaa gttcgatga                                               19

<210> SEQ ID NO 119
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 119
gttcgatgag aggctggta                                               19

<210> SEQ ID NO 120
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 120
ttcgatgaga ggctggtat                                               19

<210> SEQ ID NO 121
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 121
tcgatgagag gctggtata                                               19

<210> SEQ ID NO 122
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 122
tgtactgcgg caggactga                                               19

<210> SEQ ID NO 123
<211> LENGTH: 2156
<212> TYPE: DNA
<213> ORGANISM: Homo sapiens

<400> SEQUENCE: 123
cagcctgcgc cggggaacat cggccgcctc cagctcccgg cgcggccmgg cccggcccgg    60
```

-continued

```
ctcggccgcc tcagacgccg cctgccctgc agccatgagg cccccgcagt gtctgctgca      120
cacgccttcc ctggcttccc cactccttct cctcctcctc tggctcctgg gtggaggagt      180
gggggctgag ggccgggagg atgcagagct gctggtgacg gtgcgtgggg gccggctgcg      240
gggcattcgc ctgaagaccc ccgggggccc tgtctctgct ttcctgggca tccccttgc       300
ggagccaccc atgggacccc gtcgctttct gccaccggag cccaagcagc cttggtcagg      360
ggtggtagac gctacaacct tccagagtgt ctgctaccaa tatgtggaca ccctataccc      420
aggttttgag ggcaccgaga gtgtggaacc caaccgtgag ctgagcgagg actgcctgta      480
cctcaacgtg tggacaccat accccggcc tacatcccc acccctgtcc tcgtctggat       540
ctatggggt ggcttctaca gtggggcctc ctccttggac gtgtacgatg gccgcttctt       600
ggtacaggcc gagaggactg tgctggtgtc catgaactac cgggtgggag cctttggctt      660
cctggccctg ccggggagcc gagaggcccc gggcaatgtg gtctcctgg atcagaggct       720
ggccctgcag tgggtgcagg agaacgtggc agccttcggg ggtgacccga catcagtgac      780
gctgtttggg gagagcgcgg gagccgcctc ggtgggcatg cacctgctgt ccccgcccag      840
ccggggcctg ttccacaggg ccgtgctgca gagcggtgcc cccaatggac cctgggccac      900
ggtgggcatg ggagaggccc gtcgcagggc cacgcagctg gcccaccttg tgggctgtcc      960
tccaggcggc actggtggga atgacacaga gctggtagcc tgccttcgga cacgaccagc     1020
gcaggtcctg gtgaaccacg aatggcacgt gctgcctcaa gaaagcgtct ccggttctc      1080
cttcgtgcct gtggtagatg gagacttcct cagtgacacc ccagaggccc tcatcaacgc     1140
gggagacttc cacggcctgc aggtgctggt gggtgtggtg aaggatgagg gctcgtattt     1200
tctggtttac ggggcccag gcttcagcaa agacaacgag tctctcatca gccgggccga     1260
gttcctggcc ggggtgcggg tcggggttcc ccaggtaagt gacctggcag ccgaggctgt     1320
ggtcctgcat tacacagact ggctgcatcc cgaggacccg gcacgcctga gggaggccct     1380
gagcgatgtg gtgggcgacc acaatgtcgt gtgccccgtg gcccagctgg ctgggcgact     1440
ggctgcccag ggtgcccggg tctacgccta cgtctttgaa caccgtgctt ccacgctctc     1500
ctggcccctg tggatggggg tgccccacgg ctacgagatc gagttcatct ttgggatccc     1560
cctgaccccc tctcgaaact acacggcaga ggagaaaatc ttcgcccagc gactgatgcg     1620
atactgggcc aactttgccc gcacagggga tcccaatgag ccccgagacc ccaaggcccc     1680
acaatggccc ccgtacacgg cggggggctca gcagtacgtt agtctggacc tgcggccgct     1740
ggaggtgcgg cgggggctgc gcgcccaggc ctgcgccttc tggaaccgct tcctccccaa     1800
attgctcagc gccaccgaca cgctcgacga ggcggagcgc cagtggaagg ccgagttcca     1860
ccgctggagc tcctacatgg tgcactggaa gaaccagttc gaccactaca gcaagcagga     1920
tcgctgctca gacctgtgac cccgcgggga ccccatgtc ctccgctccg cccggccccc      1980
tagctgtata tactatttat ttcagggctg ggctataaca cagacgagcc ccagactctg     2040
cccatcccca ccccaccccg acgtcccccg gggctcccgg tcctctggca tgtcttcagg     2100
ctgagctcct ccccgcgtgc cttcgccctc tggctgcaaa taaactgtta caggcc         2156
```

<210> SEQ ID NO 124
<211> LENGTH: 3713
<212> TYPE: DNA
<213> ORGANISM: Homo sapiens

<400> SEQUENCE: 124

```
attttaggaa gtgaggagga ggcgcgggct ggagctgcgg cggggtctgg ggcgcagagc       60
```

```
agcggcggga ggaggcggac acgtggcaac agcggtagca gcccgggcgg cggcagcaac    120
agcggcggcg gcatcggccc gagccgccgg ccgccctccc accctcccgc cccgcggcag    180
ccctagctcc ctccacttgg ctcccctggt cccgctcgct cggccgggag ctgctctgtg    240
cttttctctc tgattctcca gcgacaggac ccggcgccgg gcactgagca ccgccaccat    300
ggggaagggg gttggacgtg ataagtatga gcctgcagct gtttcagaac aaggtgataa    360
aaagggcaaa aagggcaaaa agacaggga catggatgaa ctgaagaaag aagtttctat    420
ggatgatcat aaacttagcc ttgatgaact tcatcgtaaa tatggaacag acttgagccg    480
gggattaaca tctgctcgtg cagctgagat cctggcgcga gatggtccca acgccctcac    540 tcccctccc actactcctg aatggatcaa gttttgtcgg cagctctttg ggggttctc    600 aatgttactg tggattggag cgattctttg tttcttggct tatagcatcc aagctgctac    660
agaagaggaa cctcaaaacg ataatctgta cctgggtgtg gtgctatcag ccgttgtaat    720
cataactggt tgcttctcct actatcaaga agctaaaagt tcaaagatca tggaatcctt    780
caaaaacatg gtccctcagc aagcccttgt gattcgaaat ggtgagaaaa tgagcataaa    840
tgcggaggaa gttgtggttg gggatctggt ggaagtaaaa ggaggagacc gaattcctgc    900
tgacctcaga atcatatctg caaatggctg caaggtggaa aactcctcgc tcactggtga    960
atcagaaccc cagactaggt ctccagattt cacaaatgaa aaccccctgg agacgaggaa   1020
cattgccttc ttttcaacca attgtgttga aggcaccgca cgtggtattg ttgtctacac   1080
tggggatcgc actgtgatgg gaagaattgc cacacttgct tctgggctgg aaggaggcca   1140 gaccccatt gctgcagaaa ttgaacattt tatccacatc atcacgggtg tggctgtgtt   1200
cctgggtgtg tctttcttca tcctttctct catccttgag tacacctggc ttgaggctgt   1260
catcttcctc atcggtatca tcgtagccaa tgtgccggaa ggtttgctgg ccactgtcac   1320
ggtctgtctg acacttactg ccaaacgcat ggcaaggaaa aactgcttag tgaagaactt   1380
agaagctgtg gagaccttgg ggtccacgtc caccatctgc tctgataaaa ctggaactct   1440
gactcagaac cggatgacag tggcccacat gtggtttgac aatcaaatcc atgaagctga   1500
tacgacagag aatcagagtg gtgtctcttt tgacaagact tcagctacct ggcttgctct   1560
gtccagaatt gcaggtcttt gtaacagggc agtgtttcag gctaaccagg aaaacctacc   1620
tattcttaag cgggcagttg caggagatgc ctctgagtca gcactcttaa agtgcataga   1680
gctgtgctgt ggtccgtga aggagatgag agaaagatac gccaaaatcg tcgagatacc   1740
cttcaactcc accaacaagt accagttgtc tattcataag aaccccaaca catcggagcc   1800
ccaacacctg ttggtgatga agggcgcccc agaaaggatc ctagaccgtt gcagctctat   1860
cctcctccac ggcaaggagc agcccctgga tgaggagctg aaagacgcct tcagaacgc   1920 ctatttggag ctgggggcc tcggagaacg agtcctaggt ttctgccacc tctttctgcc   1980
agatgaacag tttcctgaag ggttccagtt tgacactgac gatgtgaatt tccctatcga   2040
taatctgtgc tttgttgggc tcatctccat gattgaccct ccacgggcgg ccgttcctga   2100
tgccgtgggc aaatgtcgaa gtgctggaat taaggtcatc atggtcacag agaccatcc   2160 aatcacagct aaagctattg ccaaggtgt gggcatcatc tcagaaggca atgagaccgt   2220
ggaagacatt gctgcccgcc tcaacatccc agtcagccag gtgaacccca gggatgccaa   2280
ggcctgcgta gtacacggca gtgatctaaa ggacatgacc tccgagcagc tggatgacat   2340
tttgaagtac cacactgaga tagtgtttgc caggaccctcc cctcagcaga agctcatcat   2400
```

-continued

```
tgtggaaggc tgccaaagac agggtgctat cgtggctgtg actggtgacg gtgtgaatga    2460
ctctccagct ttgaagaaag cagacattgg ggttgctatg gggattgctg gctcagatgt    2520
gtccaagcaa gctgctgaca tgattcttct ggatgacaac tttgcctcaa ttgtgactgg    2580
agtagaggaa ggtcgtctga tctttgataa cttgaagaaa tccattgctt ataccttaac    2640
cagtaacatt cccgagatca ccccgttcct gatatttatt attgcaaaca ttccactacc    2700 actgggact gtcaccatcc tctgcattga cttgggcact gacatggttc ctgccatctc     2760
cctggcttat gagcaggctg agagtgacat catgaagaga cagcccagaa atcccaaaac    2820
agacaaactt gtgaatgagc ggctgatcag catggcctat gggcagattg aatgatcca     2880 ggccctggga ggcttcttta cttactttgt gattctggct gagaacggct tcctcccaat    2940
tcacctgttg ggcctccgag tggactggga tgaccgctgg atcaacgatg tggaagacag    3000
ctacgggcag cagtggacct atgagcagag gaaaatcgtg gagttcacct gccacacagc    3060
cttcttcgtc agtatcgtgg tggtgcagtg ggccgacttg gtcatctgta agaccaggag    3120
gaattcggtc ttccagcagg ggatgaagaa caagatcttg atatttggcc tctttgaaga    3180
gacagccctg gctgctttcc tttcctactg ccctggaatg ggtgttgctc ttaggatgta    3240
tcccctcaaa cctacctggt ggttctgtgc cttccctac  tctcttctca tcttcgtata    3300
tgacgaagtc agaaaactca tcatcaggcg acgcccggc  ggctgggtgg agaaggaaac    3360
ctactattag ccccccgtcc tgcacgccgt ggagcatcag ccacacact  ctgcatccga    3420 cacccacccc ctctttgtgt acttcagtct tggagtttgg aactctaccc tggtaggaaa    3480
gcaccgcagc atgtggggaa gcaagacgtc ctggaatgaa gcatgtagct ctatgggggg    3540
aggggggagg gctgcctgaa aaccatccat ctgtggaaat gacagcgggg aaggttttta    3600 tgtgccttt  tgttttgta  aaaaggaac  acccggaaag actgaaagaa tacattttat    3660
atctggattt ttacaaataa agatggctat tataatggaa aaaaaaaaaa aaa           3713
```

<210> SEQ ID NO 125
<211> LENGTH: 2911
<212> TYPE: DNA
<213> ORGANISM: Homo sapiens

<400> SEQUENCE: 125

```
attttaggaa gtgaggagga ggcgcgggct ggagctgcgg cggggtctgg ggcgcagagc      60
agcggcggga ggaggcggac acgtggcaac agcggtagca gcccgggcgg cggcagcaac    120
agcggcggcg gcatcggccc gagccgccgg ccgcctccc  accctcccgc cccgcggcag    180
ccctagctcc ctccacttgg ctcccctggt cccgctcgct cggccgggag ctgctctgtg    240
cttttctctc tgattctcca gcgacaggac ccggcgccgg gcactgagca ccgccaccat    300
ggggaagggg gttggacgtg ataagtatga gcctgcagct gtttcagaac aaggtgataa    360
aaagggcaaa aagggcaaaa aagacaggga catggatgaa ctgaagaaag aagtttctat    420
ggatgatcat aaacttagcc ttgatgaact tcatcgtaaa tatggaacag acttgagccg    480
gggattaaca tctgctcgtg cagctgagat cctggcgcga gatggtccca acgccctcac    540 tcccctccc  actactcctg aatggatcaa gttttgtcgg cagctctttg ggggtgtctc    600
aatgttactg tggattggag cgattctttg tttcttggct tatagcatcc aagctgctac    660
agaagaggaa cctcaaaacg ataatctgta cctgggtgtg gtgctatcag ccgttgtaat    720
cataactggt tgcttctcct actatcaaga agctaaaagt tcaaagatca tggaatcctt    780
caaaaacatg gtccctcagc aagcccttgt gattcgaaat ggtgagaaaa tgagcataaa    840
```

```
tgcggaggaa gttgtggttg gggatctggt ggaagtaaaa ggaggagacc gaattcctgc    900
tgacctcaga atcatatctg caaatggctg caaggtggat aactcctcgc tcactggtga    960
atcagaaccc cagactaggt ctccagattt cacaaatgaa aaccccctgg agacgaggaa   1020
cattgccttc ttttcaacca attgtgttga aggcaccgca cgtggtattg ttgtctacac   1080
tgggatcgc actgtgatgg gaagaattgc cacacttgct tctgggctgg aaggaggcca    1140
gaccccatt gctgcagaaa ttgaacattt tatccacatc atcacgggtg tggctgtgtt    1200
cctgggtgtg tctttcttca tccttctct catccttgag tacacctggc ttgaggctgt    1260
catcttcctc atcggtatca tcgtagccaa tgtgccggaa ggtttgctgg ccactgtcac    1320
ggtctgtctg acacttactg ccaaacgcat ggcaaggaaa aactgcttag tgaagaactt    1380
agaagctgtg gagaccttgg ggtccacgtc caccatctgc tctgataaaa ctggaactct    1440
gactcagaac cggatgacag tggcccacat gtggtttgac aatcaaatcc atgaagctga    1500
tacgacagag aatcagagtg gtgtctcttt tgacaagact tcagctacct ggcttgctct    1560
gtccagaatt gcaggtcttt gtaacagggc agtgtttcag gctaaccagg aaaacctacc    1620
tattcttaag cgggcagttg caggagatgc ctctgagtca gcactcttaa agtgcataga    1680
gctgtgctgt ggttccgtga aggagatgag agaaagatac gccaaaatcg tcgagatacc    1740
cttcaactcc accaacaagt accagttgtc tattcataag aaccccaaca catcggagcc    1800
ccaacacctg ttggtgatga agggcgcccc agaaaggatc ctagaccgtt gcagctctat    1860
cctcctccac ggcaaggagc agcccctgga tgaggagctg aaagacgcct tcagaacgc    1920
ctatttggag ctgggggggcc tcggagaacg agtcctaggt ttctgccacc tctttctgcc    1980
agatgaacag tttcctgaag ggttccagtt tgacactgac gatgtgaatt ccctatcga    2040
taatctgtgc tttgttgggc tcatctccat gattgaccct ccacgggcgg ccgttcctga    2100
tgccgtgggc aaatgtcgaa gtgctggaat taaggtcatc atggtcacag agaccatcc    2160
aatcacagct aaagctattg ccaaaggtgt gggcatcatc tcagaaggca atggacctat    2220
gagcagagga aaatcgtgga gttcacctgc cacacagcct tcttcgtcag tatcgtggtg    2280
gtgcagtggg ccgacttggt catctgtaag accaggagga attcggtctt ccagcagggg    2340
atgaagaaca agatcttgat atttggcctc tttgaagaga cagccctggc tgctttcctt    2400
tcctactgcc ctggaatggg tgttgctctt aggatgtatc ccctcaaacc tacctggtgg    2460
ttctgtgcct tcccctactc tcttctcatc ttcgtatatg acgaagtcag aaaactcatc    2520
atcaggcgac gccctggcgg ctgggtggag aaggaaacct actattagcc ccccgtcctg    2580
cacgccgtgg agcatcaggc cacacactct gcatccgaca cccaccccct ctttgtgtac    2640
ttcagtcttg gagtttggaa ctctaccctg gtaggaaagc accgcagcat gtggggaagc    2700
aagacgtcct ggaatgaagc atgtagctct atgggggggag ggggggaggc tgcctgaaaa    2760
ccatccatct gtggaaatga cagcggggaa ggttttttatg tgccttttttg tttttgtaaa    2820
aaaggaacac ccgaaagac tgaaagaata catttttatat ctggatttttt acaaataaag    2880
atggctatta taatggaaaaa aaaaaaaaaa a                                   2911
```

<210> SEQ ID NO 126
<211> LENGTH: 3587
<212> TYPE: DNA
<213> ORGANISM: Homo sapiens

<400> SEQUENCE: 126

```
agcctctgtg cggtgggacc aacggacgga cggacggacg cgcgcaccta ccgaggcgcg      60
ggcgctgcag aggctcccag cccaagcctg agcctgagcc cgccccgagg tccccgcccc     120
gcccgcctgg ctctctcgcc gcggagccgc caagatgggg gacaagaaag atgacaagga     180
ctcacccaag aagaacaagg gcaaggagcg ccgggacctg gatgacctca agaaggaggt     240
ggctatgaca gagcacaaga tgtcagtgga agaggtctgc cggaaataca acacagactg     300
tgtgcagggt ttgaccccac agcaaagccca ggagatcctg gcccgggatg ggcctaacgc     360
actcacgcca ccgcctacca ccccagagtg ggtcaagttt tgccggcagc tcttcggggg     420
cttctccatc ctgctgtgga tcgggctat cctctgcttc ctggcctacg gtatccaggc     480
gggcaccgag gacgacccct ctggtgacaa cctgtacctg gcatcgtgc tggcggccgt     540 ggtgatcatc actggctgct ctcctacta ccaggaggcc aagagctcca agatcatgga     600
gtccttcaag aacatggtgc cccagcaagc cctggtgatc cgggaaggtg agaagatgca     660
ggtgaacgct gaggaggtgg tggtcgggga cctggtggag atcaagggtg agaccgagt     720 gccagctgac ctgcggatca tctcagccca cggctgcaag gtggacaact cctccctgac     780
tggcgaatcc gagccccaga ctcgctctcc cgactgcact cacgacaacc ccttggagac     840
tcggaacatc accttctttt ccaccaactg tgtggaaggc acggctcggg gcgtggtggt     900
ggccacgggc gaccgcactg tcatgggccg tatcgccacc ctggcatcag gctggaggt     960 gggcaagacg cccatcgcca tcgagattga gcacttcatc cagctcatca ccggcgtggc    1020
tgtcttcctg ggtgtctcct tcttcatcct ctccctcatt ctcggataca cctggcttga    1080
ggctgtcatc ttcctcatcg gcatcatcgt ggccaatgtc ccagagggtc tgctggccac    1140
tgtcactgtg tgtctgacgc tgaccgccaa gcgcatggcc cggaagaact gcctggtgaa    1200
gaacctggag gctgtagaaa ccctgggctc cacgtccacc atctgctcag ataagacagg    1260
gaccctcact cagaaccgca tgacagtcgc ccacatgtgg tttgacaacc agatccacga    1320
ggctgacacc actgaggacc agtcagggac ctcatttgac aagagttcgc acacctgggt    1380
ggccctgtct cacatcgctg gctctgcaa tcgcgctgtc ttcaagggtg gtcaggacaa    1440
catccctgtg ctcaagaggg atgtggctgg ggatgcgtct gagtctgccc tgctcaagtg    1500
catcgagctg tcctctggct ccgtgaagct gatgcgtgaa cgcaacaaga agtggctga    1560 gattcccttc aattccacca acaaatacca gctctccatc catgagaccg aggaccccaa    1620
cgacaaccga tacctgctgg tgatgaaggg tgcccccgag cgcatcctgg accgctgctc    1680
caccatcctg ctacagggca aggagcagcc tctggacgag gaaatgaagg aggccttcca    1740
gaatgcctac cttgagctcg gtggcctggg cgagcgcgtg cttggtttct gccattatta    1800
cctgcccgag gagcagttcc ccaagggctt tgccttcgac tgtgatgacg tgaacttcac    1860
cacggacaac ctctgctttg tgggcctcat gtccatgatc gacccacccc gggcagccgt    1920
ccctgacgcg gtgggcaagt gtcgcagcgc aggcatcaag gtcatcatgg tcaccggcga    1980 tcacccatc acggccaagg ccattgccaa gggtgtgggc atcatctctg agggcaacga    2040
gactgtggag gacatcgccg cccggctcaa cattcccgtc agccaggtta accccgggga    2100
tgccaaggcc tgcgtgatcc acggcaccga cctcaaggac ttcacctccg agcaaatcga    2160
cgagatcctg cagaatcaca ccgagatcgt cttcgcccgc acatcccccc agcagaagct    2220
catcattgtg gagggctgtc agagacaggg tgcaattgtg gctgtgaccg gggatggtgt    2280
gaacgactcc cccgctctga agaaggccga cattggggtg gccatgggca tcgctggctc    2340
tgacgtctcc aagcaggcag ctgacatgat cctgctggac gacaactttg cctccatcgt    2400
```

-continued

| | |
|---|---|
| cacaggggtg gaggagggcc gcctgatctt cgacaaccta agaagtcca ttgcctacac | 2460 |
| cctgaccagc aatatcccgg agatcacgcc cttcctgctg ttcatcatgg ccaacatccc | 2520 |
| gctgcccctg gcaccatca ccatcctctg catcgatctg gcactgaca tggtccctgc | 2580 |
| catctcactg gcgtacgagg ctgccgaaag cgacatcatg aagagacagc ccaggaaccc | 2640 |
| gcggacggac aaattggtca atgagagact catcagcatg gcctacgggc agattggaat | 2700 |
| gatccaggct ctcggtggct tcttctctta ctttgtgatc ctggcagaaa atggcttctt | 2760 |
| gcccggcaac ctggtgggca tccggctgaa ctgggatgac cgcaccgtca atgacctgga | 2820 |
| agacagttac gggcagcagt ggacatacga gcagaggaag gtggtggagt tcacctgcca | 2880 |
| cacggccttc tttgtgagca tcgttgtcgt ccagtgggcc gatctgatca tctgcaagac | 2940 |
| ccggaggaac tcggtcttcc agcagggcat gaagaacaag atcctgatct tcgggctgtt | 3000 |
| tgaggagacg gccctggctg ccttcctgtc ctactgcccc ggcatggacg tggccctgcg | 3060 |
| catgtaccct ctcaagccca gctggtggtt ctgtgccttc ccctacagtt tcctcatctt | 3120 |
| cgtctacgac gaaatccgca aactcatcct gcgcaggaac ccaggggtt gggtggagaa | 3180 |
| ggaaacctac tactgacctc agccccacca catcgcccat ctcttcccg tccccaggc | 3240 |
| ccaggaccgc ccctgtcagt cccccaatt ttgtattctg gggggaggag ccctctcttc | 3300 |
| ctgtggcccc accttggccc ccaccccctc cactatctcc tgccgccccc actctggctg | 3360 |
| gcttctctcc cctgcccaa acctctctcc tctctctttt ctgtgtcagt ttctctccct | 3420 |
| ctcctcaccc ctctatccat tcctcccgcc ccagccacct ccctgggctc tttttactc | 3480 |
| cccttcagcc ccccggctga tgccatctct ggttctggac aattatcaaa tatatcagtg | 3540 |
| gggagagaga aaaaaaaaa aaaaaaaaa aaaaaaaaa aaaaaaa | 3587 |

<210> SEQ ID NO 127
<211> LENGTH: 3873
<212> TYPE: DNA
<213> ORGANISM: Homo sapiens

<400> SEQUENCE: 127

| | |
|---|---|
| aaccacaggg cctgggactg gggggttccc agatccttga agctcactcc gcctcctcac | 60 |
| tctcactgca tttcccacct tcctgtgggc cttgcggcat cttcatcact gaggcacctg | 120 |
| gttacgcttc acctcttgtt tcctgccctc actgcattcc ctcacctcta ccttttatc | 180 |
| cttccaccct aggcttctct cctccctctt ccctcactcc tgactcttcc tcttcccagc | 240 |
| ggacggctgg aggaccgctc agtctctcct ctctcacttc ccttcctctc tctcaccttc | 300 |
| accacccaac acctccctcc ctgcctcttt cttctgctc cctcattctc tccccaccac | 360 |
| tctcttctcg tggccccctt gccgcgcgc cctcttccct tccccttgcc tcactctctc | 420 |
| agctttcttc ccacagttga gctcgggcag ctctttctgg ggatagctat ggggctttgg | 480 |
| gggaagaaag ggacagtggc tccccatgac cagagtccaa gacgaagacc taaaaaaggg | 540 |
| cttatcaaga aaaaaatggt gaagagggaa aacagaagc gcaatatgga ggaactgaag | 600 |
| aaggaagtgg tcatggatga tcacaaatta accttggaag agctgagcac caagtactcc | 660 |
| gtggacctga caagggcca tagccaccaa agggcaaagg aaatcctgac tcagatgga | 720 |
| cccaatactg ttaccccacc ccccaccact ccagaatggg tcaaattctg taagcaactg | 780 |
| ttcggaggct tctccctcct actatggact ggggccattc tctgctttgt ggcctacagc | 840 |
| atccagatat atttcaatga ggagcctacc aaagacaacc tctacctgag catcgtactg | 900 |

```
tccgtcgtgg tcatcgtcac tggctgcttc tcctattatc aggaggccaa gagctccaag    960
atcatggagt cttttaagaa catggtgcct cagcaagctc tggtaattcg aggaggagag   1020
aagatgcaaa ttaatgtaca agaggtggtg ttgggagacc tggtggaaat caagggtgga   1080
gaccgagtcc ctgctgacct ccggcttatc tctgcacaag gatgtaaggt ggacaactca   1140
tccttgactg gggagtcaga accccagagc cgctcccctg acttcaccca tgagaaccct   1200
ctggagaccc gaaacatctg cttctttcc accaactgtg tggaaggaac cgcccggggt   1260
attgtgattg ctacgggaga ctccacagtg atgggcagaa ttgcctccct gacgtcaggc   1320
ctggcggttg ccagacacc tatcgctgct gagatcgaac acttcatcca tctgatcact   1380
gtggtggccg tcttccttgg tgtcactttt tttgcgctct cacttctctt gggctatggt   1440
tggctggagg ctatcatttt tctcattggc atcattgtgg ccaatgtgcc tgaggggctg   1500
ttggccacag tcactgtgtg cctgaccctc acagccaagc gcatggcgcg aagaactgc    1560 ctggtgaaga acctggaggc ggtggagacg ctgggctcca cgtccaccat ctgctcagac   1620
aagacgggca ccctcaccca gaaccgcatg accgtcgccc acatgtggtt tgatatgacc   1680
gtgtatgagg ccgacaccac tgaagaacag actggaaaaa catttaccaa gagctctgat   1740
acctggttta tgctggcccg aatcgctggc ctctgcaacc gggctgactt taaggctaat   1800
caggagatcc tgcccattgc taagagggcc acaacaggtg atgcttccga gtcagccctc   1860
ctcaagttca tcgagcagtc ttacagctct gtggcggaga tgagagagaa aaaccccaag   1920
gtggcagaga ttccctttaa ttctaccaac aagtaccaga tgtccatcca ccttcgggag   1980
gacagctccc agacccacgt actgatgatg aagggtgctc cggagaggat cttggagttt   2040
tgttctacct ttcttctgaa tgggcaggag tactcaatga acgatgaaat gaaggaagcc   2100
ttccaaaatg cctatttaga actgggaggt ctggggaac gtgtgctagg cttctgcttc   2160
ttgaatctgc ctagcagctt ctccaaggga ttcccattta atacagatga aataaatttc   2220
cccatggaca acctttgttt tgtgggcctc atatccatga ttgaccctcc ccgagctgca   2280
gtgcctgatg ctgtgagcaa gtgtcgcagt gcaggaatta aggtgatcat ggtaacagga   2340
gatcatccca ttacagctaa ggccattgcc aagggtgtgg gcatcatctc agaaggcact   2400
gagacggcag aggaagtcgc tgcccggctt aagatcccta tcagcaaggt cgatgccagt   2460
gctgccaaag ccattgtggt gcatggtgca gaactgaagg acatacagtc caagcagctt   2520
gatcagatcc tccagaacca ccctgagatc gtgtttgctc ggacctcccc tcagcagaag   2580
ctcatcattg tcgagggatg tcagaggctg ggagccgttg tggccgtgac aggtgacggg   2640
gtgaacgact cccctgcgct gaagaaggct gacattggca ttgccatggg catctctggc   2700
tctgacgtct ctaagcaggc agccgacatg atcctgctgg atgacaactt tgcctccatc   2760
gtcacggggg tggaggaggg ccgcctgatc tttgacaacc tgaagaaatc catcatgtac   2820
accctgacca gcaacatccc cgagatcacg cccttcctga tgttcatcat cctcggtata   2880
cccctgcctc tgggaaccat aaccatcctc tgcattgatc tcggcactga catggtccct   2940
gccatctcct ggcttatga gtcagctgaa agcgacatca tgaagaggct tccaaggaac   3000
ccaaagacgg ataatctggt gaaccaccgt ctcattggca tggcctatgg acagattggg   3060
atgatccagg ctctggctgg attctttacc tactttgtaa tcctggctga gaatggtttt   3120
aggcctgttg atctgctggg catccgcctc cactgggaag ataaatactt gaatgacctg   3180
gaggacagct acggacagca gtggaccat gagcaacgaa aagttgtgga gttcacatgc   3240
caaacggcct ttttgtcac catcgtggtt gtgcagtggg cggatctcat catctccaag   3300
```

-continued

| | |
|---|---|
| actcgccgca actcactttt ccagcagggc atgagaaaca aagtcttaat atttgggatc | 3360 |
| ctggaggaga cactcttggc tgcatttctg tcctacactc caggcatgga cgtggccctg | 3420 |
| cgaatgtacc cactcaagat aacctggtgg ctctgtgcca ttccctacag tattctcatc | 3480 |
| ttcgtctatg atgaaatcag aaaactcctc atccgtcagc acccggatgg ctgggtggaa | 3540 |
| agggagacgt actactaaac tcagcagatg aagagcttca tgtgcacag gggtgttgtg | 3600 |
| agagctggga tggggccaga gattataagt ttgacacaac atctgagaca ctaggatgaa | 3660 |
| ttatcttgga tgagaaagat gggcaatcct gggctggctt gagggaatca tgggcagagg | 3720 |
| atgaggtggg ctgaagggaa gcccagcctg catctagctg gagccccgca gggaggggca | 3780 |
| tggtcctgct gaatcccgta gccagtctag acagtaaatg tctggaaaag ccaaaaaaaa | 3840 |
| aaaaaaaaa aaaaaaaaaa aaaaaaaaaa aaa | 3873 |

<210> SEQ ID NO 128
<211> LENGTH: 951
<212> TYPE: DNA
<213> ORGANISM: Homo sapiens

<400> SEQUENCE: 128

| | |
|---|---|
| caccagccca gccagaagca agtcccagcc ccctggccta ccttttgggg | 60 |
| cccttctctg aaccaggctc ccctgtcctg caactctgtc attcacaggg atgatccagg | 120 |
| ctctggctgg attctttacc tactttgtaa tcctggctga gaatggtttt aggcctgttg | 180 |
| atctgctggg catccgcctc cactgggaag ataaatactt gaatgacctg gaggacagct | 240 |
| acggacagca gtggacctat gagcaacgaa aagttgtgga gttcacatgc caaacggcct | 300 |
| tttttgtcac catcgtggtt gtgcagtggg cggatctcat catctccaag actcgccgca | 360 |
| actcactttt ccagcagggc atgagaaaca aagtcttaat atttgggatc ctggaggaga | 420 |
| cactcttggc tgcatttctg tcctacactc caggcatgga cgtggccctg cgaatgtacc | 480 |
| cactcaagat aacctggtgg ctctgtgcca ttccctacag tattctcatc ttcgtctatg | 540 |
| atgaaatcag aaaactcctc atccgtcagc acccggatgg ctgggtggaa agggagacgt | 600 |
| actactaaac tcagcagatg aagagcttca tgtgcacag gggtgttgtg agagctggga | 660 |
| tggggccaga gattataagt ttgacacaac atctgagaca ctaggatgaa ttatcttgga | 720 |
| tgagaaagat gggcaatcct gggctggctt gagggaatca tgggcagagg atgaggtggg | 780 |
| ctgaagggaa gcccagcctg catctagctg gagccccgca gggaggggca tggtcctgct | 840 |
| gaatcccgta gccagtctag acagtaaatg tctggaaaag ccctcaaaaa aaaaaaaaa | 900 |
| aaaaaaaaa aaaaaaaaaa aaaaaaaaa aaaaaaaaa aaaaaaaaaa a | 951 |

<210> SEQ ID NO 129
<211> LENGTH: 2212
<212> TYPE: DNA
<213> ORGANISM: Homo sapiens

<400> SEQUENCE: 129

| | |
|---|---|
| cagcggcgcg tcctgcctgc agagagccag gccggagaag ccgagcggcg cagaggacgc | 60 |
| cagggcgcgc gccgcagcca cccaccctcc ggaccgcggc agctgctgac ccgccatcgc | 120 |
| catgccccgc gggaaagcca aggaggaggg cagctggaag aaattcatct ggaactcaga | 180 |
| gaagaaggag tttctgggca ggaccggtgg cagttggttt aagatccttc tattctacgt | 240 |
| aatattttat ggctgcctgg ctggcatctt catcggaacc atccaagtga tgctgctcac | 300 |

| | | |
|---|---|---|
| catcagtgaa tttaagccca catatcagga ccgagtggcc ccgccaggat aacacagat | | 360 |
| tcctcagatc cagaagactg aaatttcctt tcgtcctaat gatcccaaga gctatgaggc | | 420 |
| atatgtactg aacatagtta ggttcctgga aaagtacaaa gattcagccc agagggatga | | 480 |
| catgattttt gaagattgtg gcgatgtgcc cagtgaaccg aaagaacgag gagacttaa | | 540 |
| tcatgaacga ggagagcgaa aggtctgcag attcaagctt gaatggctgg gaaattgctc | | 600 |
| tggattaaat gatgaaactt atggctacaa agagggcaaa ccgtgcatta ttataaagct | | 660 |
| caaccgagtt ctaggcttca aacctaagcc tcccaagaat gagtccttgg agacttaccc | | 720 |
| agtgatgaag tataacccaa atgtccttcc cgttcagtgc actggcaagc gagatgaaga | | 780 |
| taaggataaa gttggaaatg tggagtattt tggactgggc aactcccctg gttttcctct | | 840 |
| gcagtattat ccgtactatg gcaaactcct gcagcccaaa tacctgcagc ccctgctggc | | 900 |
| cgtacagttc accaatctta ccatggacac tgaaattcgc atagagtgta aggcgtacgg | | 960 |
| tgagaacatt gggtacagtg agaaagaccg ttttcaggga cgttttgatg taaaaattga | | 1020 |
| agttaagagc tgatcacaag cacaaatctt tcccactagc catttaataa gttaaaaaaa | | 1080 |
| gatacaaaaa caaaaaccta ctagtcttga acaaactgtc atacgtatgg gacctacact | | 1140 |
| taatctatat gctttacact agctttctgc atttaatagg ttagaatgta aattaaagtg | | 1200 |
| tagcaatagc aacaaaatat ttattctact gtaaatgaca aaagaaaaag aaaaattgag | | 1260 |
| ccttgggacg tgcccatttt tactgtaaat tatgattccg taactgactt gtagtaagca | | 1320 |
| gtgtttctgg cccctaagta ttgctgcctt gtgtatttta tttagtgtac agtactacag | | 1380 |
| gtgcatactc tggtcatttt tcaagccatg ttttattgta tctgttttct actttatgtg | | 1440 |
| agcaaggttt gctgtccaag gtgtaaatat tcaacgggaa taaaactggc atggtaattt | | 1500 |
| tttttttttt ttttttttg ttttttggct ctttcaaagg taatggccca tcgatgagca | | 1560 |
| ttttaacat actccatagt cttttcctgt ggtgttaggt ctttatttt atttttttcc | | 1620 |
| tgggggctgg ggtgggggtt tgtcatgggg gaactgccct ttaaatttta agtgacacta | | 1680 |
| cagaaaaaca caaaaggtg atgggttgtg ttatgcttgt attgaatgct gtcttgacat | | 1740 |
| ctcttgcctt gtcctccggt atgttctaaa gctgtgtctg agatctggat ctgcccatca | | 1800 |
| ctttggctag tgacagggct aattaatttg ctttatacat tttcttttac tttccttttt | | 1860 |
| tccttctgg aggcatcaca tgctggtgct gtgtctttat gaatgtttta accattttca | | 1920 |
| tggtggaaga attttatatt tatgcagttg tacaatttta ttttttttctg caagaaaaag | | 1980 |
| tgtaatgtat gaaataaacc aaagtcactt gtttgaaaat aaatctttat tttgaacttt | | 2040 |
| ataaaaagca atgcagtacc ccatagactg gtgttaaatg ttgtctacag tgcaaaatcc | | 2100 |
| atgttctaac atatgtaata attgccagga gtacagtgct cttgttgatc ttgtattcag | | 2160 |
| tcaggttaaa acaacggaca ataaaagaat gaacacattc aaaaaaaaaa aa | | 2212 |

<210> SEQ ID NO 130
<211> LENGTH: 1568
<212> TYPE: DNA
<213> ORGANISM: Homo sapiens

<400> SEQUENCE: 130

| | | |
|---|---|---|
| cagcggcgcg tcctgcctgc agagagccag gccggagaag ccgagcggcg cagaggacgc | | 60 |
| cagggcgcgc gccgcagcca cccaccctcc ggaccgcggc agctgctgac ccgccatcgc | | 120 |
| catggccccgc gggaaagcca aggaggaggg cagctggaag aaattcatct ggaactcaga | | 180 |
| gaagaaggag tttctgggca ggaccggtgg cagttggttt aagatccttc tattctacgt | | 240 |

```
aatattttat ggctgcctgg ctggcatctt catcggaacc atccaagtga tgctgctcac      300
catcagtgaa tttaagccca catatcagga ccgagtggcc ccgccaggat taacacagat      360
tcctcagatc cagaagactg aaatttcctt tcgtcctaat gatcccaaga gctatgaggc      420
atatgtactg aacatagtta ggttcctgga aaagtacaaa gattcagccc agagggatga      480
catgattttt gaagattgtg gcgatgtgcc cagtgaaccg aaagaacgag agactttaa       540 tcatgaacga ggagagcgaa aggtctgcag attcaagctt gaatggctgg gaaattgctc      600
tggattaaat gatgaaactt atggctacaa agagggcaaa ccgtgcatta ttataaagct      660
caaccgagtt ctaggcttca aacctaagcc tcccaagaat gagtccttgg agacttaccc      720
agtgatgaag tataacccaa atgtccttcc cgttcagtgc actggcaagc gagatgaaga      780
taaggataaa gttggaaatg tggagtattt tggactgggc aactcccctg gttttcctct      840
gcagtattat ccgtactatg gcaaactcct gcagcccaaa tacctgcagc ccctgctggc      900
cgtacagttc accaatctta ccatggacac tgaaattcgc atagagtgta aggcgtacgg      960
tgagaacatt gggtacagtg agaaagaccg tttttcaggga cgttttgatg taaaaattaa     1020 atttaagtg acactacaga aaaacacaaa aaggtgatgg gttgtgttat gcttgtattg      1080
aatgctgtct tgacatctct tgccttgtcc tccggtatgt tctaaagctg tgtctgagat      1140
ctggatctgc ccatcacttt ggctagtgac agggctaatt aatttgcttt atacattttc      1200 ttttacttc cttttttcct ttctggaggc atcacatgct ggtgctgtgt ctttatgaat      1260
gttttaacca ttttcatggt ggaagaattt tatatttatg cagttgtaca attttatttt      1320
tttctgcaag aaaagtgta atgtatgaaa taaaccaaag tcacttgttt gaaaataaat       1380
ctttattttg aactttataa aaagcaatgc agtaccccat agactggtgt taaatgttgt      1440
ctacagtgca aaatccatgt tctaacatat gtaataattg ccaggagtac agtgctcttg     1500
ttgatcttgt attcagtcag gttaaaacaa cggacaataa agaatgaac acattcaaaa       1560 aaaaaaaa                                                              1568

<210> SEQ ID NO 131
<211> LENGTH: 3350
<212> TYPE: DNA
<213> ORGANISM: Homo sapiens

<400> SEQUENCE: 131
ggagcggagc ctccgcctgg ggggcccccc atccctggct gtccccagc tgcgcgtccc        60 cgccccaccc ccgcggctga gccaccaccg gtgcagtggt ctccgcttgg cggagcgagc     120
cttgagcttc gttccacagc ttctttgcat cttggatttc ggggcggccc cctccccac      180 ctctctctgc ctttttgtac cccgcttttt ttctgcgttc tgctcggttt ttgtagccgt     240 ctgttttgc accccatttc gttttgtttc tagacggttt ggtggggggt gaagctgcat      300 tcataccct tcctcttgtt attctcccct gctctgacag cacccctttt catcgcagtt      360 gggggccta ggatcggtgc atcttccgcc gcgctgccag caccccgcag cgcgtggtcg      420 tgcacccgg aatctgcagc agctgcatat ctgagggggg tctcctttgc ccgcgccgcc     480
ttcgctcccc gtgcttttgg gtgtgtggag ggcttcagcg cgcggcgccc ccgcttctcc     540 gcaaccccc gccccgcgcc cggactcgcc ccgcgccacc aagatggtca tccagaaaga     600
gaagaagagc tgcgggcagg tggttgagga gtggaaggag ttcgtgtgga acccgaggac     660
gcaccagttt atgggccgca ccgggaccag ctgggccttt atcctcctct tctacctcgt     720
```

```
tttttatggg ttcctcaccg ccatgttcac cctcaccatg tgggtgatgc tgcagactgt    780
ctccgaccat accccaagt accaggaccg actggccaca ccgggcttga tgattcgccc    840
caagactgag aaccttgatg tcattgtcaa tgtcagtgac actgaaagct gggaccagca    900
tgttcagaag ctcaacaagt tcttggagcc ttacaacgac tctatccaag cccaaaagaa    960
tgatgtctgc cgccctgggc gctattacga acagccagat aatggagtcc tcaactaccc   1020
caaacgtgcc tgccaattca accggaccca gctgggcaac tgctccggca ttggggactc   1080
cacccactat ggttacagca ctgggcagcc ctgtgtcttc atcaagatga accgggtcat   1140
caacttctat gcaggagcaa accagagcat gaatgttacc tgtgctggga agcgagatga   1200
agatgctgag aatctcggca acttcgtcat gttccccgcc aacggcaaca tcgacctcat   1260
gtacttcccc tactatggca aaagttcca cgtgaactac acacagcccc tggtggctgt   1320
gaagttcctg aatgtgaccc ccaacgtgga ggtgaatgta aatgtcgca tcaacgccgc    1380
caacatcgcc acagacgatg agcgagacaa gttcgccggc cgcgtggcct tcaaactccg   1440
catcaacaaa acctgaggcc ccttcctccc acccatctc tctcctgtgg atgctcctgg    1500
aatgtccctg accctgcctg atccctccct cacccacccc aaaggtattt ttgataacag   1560
agctatgact tgtctgagcc tcacatcctt ttccttgact tctcaaccca gcctgaagtc   1620
cattgcggtt ccgtcactcg cctttcccac caacttctcc caacctcaga tcagtcagac   1680
agggagctgg gctaagatgg ccacggagga gttaggagcc tttctagttc tggtttagct   1740
gtgagagcta tccactctcc tgcctgcata tcccctgaga gttataggaa gtgcccactg   1800
acccacccac ccacctacac cccccgccac acacacacac aaacgtgcac acgcgtctca   1860
tttgacccct ttgcttccag agatgaatgt ggcactccct ccttccattc ctaagctcta   1920
gccaccgtcc cttgatctct catactttct ccctgtctac acagtcgcca tcttggtgac   1980
tttgaatta tctggctcct gggcaggtct tctcctcctc tccatccta ttccctcctc    2040
tgaaatgcac cccttgtaa ttgaggacaa ggtggttctg tggccttttc cctctttgct   2100
ggcacgttct gcttctcacc ctctggtgac tctgtgagct gggaaatgag ggactggaag   2160
tgaggcctgt gttgacccct cctgaaaatc ctctagcagc ccccgacttc agcagtttct   2220
ttctttgttt ttttgagatg gagtttcgct cttgttgccc aggctggagt gcaatggtgc   2280
aatctcagct cactgcaact tccgcatccc aggttcaagc gattctcccg cctcaggttc   2340
ccgagtagct gggactacag gcatgtgcca ccatgcccgg ctaatttctt tctttctttt   2400
ttttttttt tgcatttttt agtagagatg ggggtttctc cttgttggtc aggctggtct   2460
cgaactcccg acctcaggtg atccacctgc ctcggcctcc caaagtgttg ggattacagg   2520
cgtgagccac cgcgcccggc cttcagtttc ttcctaggcc gttctgtcac ccaaatagct   2580
gctacccaga ggggcgggt tgacctaggc tgaatatcca ctttgttttt atggatggct   2640
cccttccccc attcgccttc ccagaatatc cttcaagttc cacttcccag ggagctctgg   2700
gggaggggcg gccattctgg ctccgtcccc agtggccacc ttggaaacat cggctggctt   2760
tgggactatt ccacctcctt cccctgagcc cagatctgcc cccaccatcc tttctctggc   2820
ttcttttagc aagttatcaa ctaatcacta actccttcct tttcctctgc atgccagcct   2880
gaaaattcca aatctagcct ctgaatgtct tggctccatc tcttcagacc cctttgcctt   2940
taaaaaaaaa acaaaaacaa aaacaaaaaa acccataatg cccacagaat gtcaaatgag   3000
gggcctcctg cctcctgctc tgaatattct gtagctgtag aggcatttta acccttttgtc   3060
ctccagcatc ccttcacttc ctcatcctct ctaacctcct ttttcttttt ttaatgctgc   3120
```

```
agcctccaca ctccacccac aggtggaccc ttcccttttt ctctagctgg atctgtgttt    3180
cttcccttcg ggccccatg ttttcctgca cccgccctac catggtctct ctctgcagtt    3240
atttaatgcc tgtgtcagat ctactgtaaa aagaggatta agtaaaataa aatgagagca    3300
attatatata taaatatata tcatacacag agaaaaaaaa aaaaaaaaa                3350

<210> SEQ ID NO 132
<211> LENGTH: 1853
<212> TYPE: DNA
<213> ORGANISM: Homo sapiens

<400> SEQUENCE: 132
ggcgcggcgc ggcgcagtcg gctcgagtac tccccgtaac gaggaggtgt tctcggccgt      60
cccacccttc actgccgtct ccgggctgcg ccgccggagc cgggacgcgc ctccgcagcc     120
ctcgccgcct ccatcccgc ggccgcagct cctctcgccg tccgcgcgca caccatgacg     180
aagaacgaga agaagtccct caaccagagc ctggccgagt ggaagctctt catctacaac     240
ccgaccaccg gagaattcct ggggcgcacc gccaagagct gggggtttgat cttgctcttc     300 tacctagttt tttatgggtt cctggctgca ctcttctcat tcacgatgtg ggttatgctt     360
cagactctca acgatgaggt tccaaaatac cgtgaccaga ttcctagccc aggactcatg     420 gttttttccaa aaccagtgac cgcattggaa tatacattca gtaggtctga tccaacttcg     480
tatgcagggt acattgaaga ccttaagaag tttctaaaac catatacttt agaagaacag     540
aagaacctca cagtctgtcc tgatggagca ctttttgaac agaagggtcc agtttatgtt     600
gcatgtcagt ttcctatttc attacttcaa gcatgcagtg gtatgaatga tcctgatttt     660
ggctattctc aaggaaaccc ttgtattctt gtgaaaatga acagaataat tggattaaag     720
cctgaaggag tgccaaggat agattgtgtt tcaagaatg aagatatacc aaatgtagca     780
gtttatcctc ataatggaat gatagactta aaatatttcc catattatgg gaaaaaactg     840
catgttgggt atctacagcc attggttgct gttcaggtca gctttgctcc taacaacact     900
gggaaagaag taacagttga gtgcaagatt gatggatcag ccaacctaaa aagtcaggat     960
gatcgtgaca agttttggg acgagttatg ttcaaaatca cagcacgtgc atagtatgag    1020
taggatatct ccacagagta aatgttgtgt tgtctgtctt cattttgtaa cagctggacc    1080
ttccattcta gaattatgag accaccttgg agaaaggtgt gtggtacatg acattgggtt    1140
acatcataac gtgcttccag atcatagtgt tcagtgtcct ctgaagtaac tgccgttgc    1200 ctctgctgcc ctttgaacca gtgtacagtc gccagatagg gaccggtgaa cacctgattc    1260
caaacatgta ggatgggggt cttgtcctct ttttatgtgg tttaattgcc aagtgtctaa    1320
agcttaatat gccgtgctat gtaaatattt tatggatata acaactgtca tattttgatg    1380
tcaacagagt tttagggata aaatggtacc cggccaacat caagtgactt tatagctgca    1440
agaaatgtgg tatgtggaga agttctgtat gtgaggaagg aaaaaaagaa aataaaagtg    1500
tgtttgaaaa atattatctt gggttctttg taaaatttat ttttttacatg ctgaattagc    1560 ctcgatcttt ttgattaaga gcacaaactt tttttgtaa aacatgtaaa aaaaaaaact    1620
gggattaatt tttagtgttg gaactgcctc ttatttagg ctgtagataa aatagcattt    1680
ttaggttagc cagtgtgact atgcacctaa ttttttatga gattaaattc ataagactta    1740
atttgtacaa tagtttgtga aatatcttgt tactgctttt atttagcaga ctgtggactg    1800
taataaagta tataaattgt gaaatataaa aacttggaac ttattcaaag ctt           1853
```

<210> SEQ ID NO 133
<211> LENGTH: 6891
<212> TYPE: DNA
<213> ORGANISM: Homo sapiens

<400> SEQUENCE: 133

| | | | | | |
|---|---|---|---|---|---|
| ggtggcctct | gtggccgtcc | aggctagcgg | cggcccgcag | gcggcgggga | gaaagactct | 60 |
| ctcacctggt | cttgcggctg | tgccaccgc | cggccagggg | tgtggagggc | gtgctgccgg | 120 |
| agacgtccgc | cgggctctgc | agttccgccg | ggggtcgggc | agctatggag | ccgcggccca | 180 |
| cggcgccctc | ctccggcgcc | ccgggactgg | ccggggtcgg | ggagacgccg | tcagccgctg | 240 |
| cgctggccgc | agccagggtg | gaactgcccg | gcacggctgt | gccctcggtg | ccggaggatg | 300 |
| ctgcgcccgc | gagccgggac | ggcggcgggg | tccgcgatga | gggccccgcg | gcggccgggg | 360 |
| acgggctggg | cagacccttg | ggcccaccc | cgagccagag | ccgtttccag | gtggacctgg | 420 |
| tttccgagaa | cgccgggcgg | gccgctgctg | cggcggcggc | ggcggcgcg | gcagcggcgg | 480 |
| cggctggtgc | tggggcgggg | gccaagcaga | ccccccgcgga | cggggaagcc | agcggcgaga | 540 |
| gcgagccggc | taaaggcagc | gaggaagcca | agggccgctt | ccgcgtgaac | ttcgtggacc | 600 |
| cagctgcctc | ctcgtcggct | gaagacagcc | tgtcagatgc | tgccggggtc | ggagtcgacg | 660 |
| ggcccaacgt | gagcttccag | aacggcgggg | acacggtgct | gagcgagggc | agcagcctgc | 720 |
| actccggcgg | cggcggcggc | agtgggcacc | accagcacta | ctattatgat | acccacacca | 780 |
| acacctacta | cctgcgcacc | ttcggccaca | acaccatgga | cgctgtgccc | aggatcgatc | 840 |
| actaccggca | cacagccgcg | cagctgggcg | agaagctgct | ccggcctagc | ctggcggagc | 900 |
| tccacgacga | gctggaaaag | gaacctttg | aggatggctt | tgcaaatggg | gaagaaagta | 960 |
| ctccaaccag | agatgctgtg | gtcacgtata | ctgcagaaag | taaaggagtc | gtgaagtttg | 1020 |
| gctggatcaa | gggtgtatta | gtacgttgta | tgttaaacat | ttggggtgtg | atgcttttca | 1080 |
| ttagattgtc | atggattgtg | ggtcaagctg | gaataggtct | atcagtcctt | gtaataatga | 1140 |
| tggccactgt | tgtgacaact | atcacaggat | tgtctacttc | agcaatagca | actaatggat | 1200 |
| ttgtaagagg | aggaggagca | tattatttaa | tatctagaag | tctagggcca | gaatttggtg | 1260 |
| gtgcaattgg | tctaatcttc | gccttttgcca | acgctgttgc | agttgctatg | tatgtggttg | 1320 |
| gatttgcaga | aaccgtggtg | gagttgctta | aggaacattc | catacttatg | atagatgaaa | 1380 |
| tcaatgatat | ccgaattatt | ggagccatta | cagtcgtgat | tcttttaggt | atctcagtag | 1440 |
| ctggaatgga | gtgggaagca | aaagctcaga | ttgttctttt | ggtgatccta | cttcttgcta | 1500 |
| ttggtgattt | cgtcatagga | acatttatcc | cactggagag | caagaagcca | aaagggtttt | 1560 |
| ttggttataa | atctgaaata | tttaatgaga | actttgggcc | cgattttcga | gaggaagaga | 1620 |
| ctttcttttc | tgtatttgcc | atctttttc | ctgctgcaac | tggtattctg | gctggagcaa | 1680 |
| atatctcagg | tgatcttgca | gatcctcagt | cagccatacc | caaggaaca | ctcctagcca | 1740 |
| ttttaattac | tacattggtt | tacgtaggaa | ttgcagtatc | tgtaggttct | tgtgttgttc | 1800 |
| gagatgccac | tggaaacgtt | aatgacacta | tcgtaacaga | gctaacaaac | tgtacttctg | 1860 |
| cagcctgcaa | attaaacttt | gatttttcat | cttgtgaaag | cagtccttgt | tcctatggcc | 1920 |
| taatgaacaa | cttccaggta | atgagtatgg | tgtcaggatt | acaccacta | atttctgcag | 1980 |
| gtatattttc | agccactctt | tcttcagcat | tagcatccct | agtgagtgct | cccaaaatat | 2040 |
| ttcaggctct | atgtaaggac | aacatctacc | cagcttccca | gatgtttgct | aaaggttatg | 2100 |
| ggaaaaataa | tgaacctctt | cgtggctaca | tcttaacatt | cttaattgca | cttggattca | 2160 |

-continued

```
tcttaattgc tgaactgaat gttattgcac caattatctc aaacttcttc cttgcatcat    2220
atgcattgat caattttca gtattccatg catcacttgc aaaatctcca ggatggcgtc     2280
ctgcattcaa atactacaac atgtggatat cacttcttgg agcaattctt tgttgcatag    2340
taatgttcgt cattaactgg tgggctgcat tgctaacata tgtgatagtc cttgggctgt    2400
atatttatgt tacctacaaa aaaccagatg tgaattgggg atcctctaca caagccctga    2460
cttacctgaa tgcactgcag cattcaattc gtctttctgg agtggaagac cacgtgaaaa    2520
actttaggcc acagtgtctt gttatgacag gtgctccaaa ctcacgtcca gctttacttc    2580
atcttgttca tgatttcaca aaaaatgttg gtttgatgat ctgtggccat gtacatatgg    2640
gtcctcgaag acaagccatg aaagagatgt ccatcgatca agccaaatat cagcgatggc    2700
ttattaagaa caaaatgaag gcattttatg ctccagtaca tgcagatgac ttgagagaag    2760
gtgcacagta tttgatgcag gctgctggtc ttggtcgtat gaagccaaac acacttgtcc    2820
ttggatttaa gaaagattgg ttgcaagcag atatgaggga tgtggatatg tatataaact    2880
tatttcatga tgcttttgac atacaatatg gagtagtggt tattcgccta aaagaaggtc    2940
tggatatatc tcatcttcaa ggacaagaag aattattgtc atcacaagag aaatctcctg    3000
gcaccaagga tgtggtagta agtgtggaat atagtaaaaa gtccgattta gatacttcca    3060
aaccactcag tgaaaaacca attacacaca agttgagga agaggatggc aagactgcaa     3120
ctcaaccact gttgaaaaaa gaatccaaag gccctattgt gcctttaaat gtagctgacc    3180
aaaagcttct tgaagctagt acacagtttc agaaaaaaca aggaaagaat actattgatg    3240
tctggtggct ttttgatgat ggaggtttga ccttattgat accttacctt ctgacgacca    3300
agaaaaaatg gaaagactgt aagatcagag tattcattgg tggaaagata aacagaaatag   3360 accatgaccg gagagcgatg gctactttgc ttagcaagtt ccggatagac ttttctgata    3420
tcatggttct aggagatatc aataccaaac caaagaaaga aaatattata gcttttgagg    3480
aaatcattga gccatacaga cttcatgaag atgataaaga gcaagatatt gcagataaaa    3540
tgaaagaaga tgaaccatgg cgaataacag ataatgagct tgaactttat aagaccaaga    3600
cataccggca gatcaggtta aatgagttat taaaggaaca ttcaagcaca gctaatatta    3660
ttgtcatgag tctcccagtt gcacgaaaag gtgctgtgtc tagtgctctc tacatggcat    3720
ggttagaagc tctatctaag gacctaccac caatcctcct agttcgtggg aatcatcaga    3780
gtgtccttac cttctattca taaatgttct atacagtgga cagccctcca gaatggtact    3840
tcagtgccta gtgtagtaac tgaaatcttc aatgacacat taacatcaca atggcgaatg    3900 gtgactttc tttcacgatt tcattaattt gaaagcacac aggaaagttg ctccattgat    3960
aacgtgtatg gagacttcgg ttttagtcaa ttccatatct caatcttaat ggtgattctt    4020
ctctgttgaa ctgaagtttg tgagagtagt tttcctttgc tacttgaata gcaataaaag    4080
cgtgttaact ttttgattga tgaaagaagt acaaaaagcc tttagccttg aggtgccttc    4140
tgaaattaac caaatttcat ccatatatcc tcttttataa acttatagaa tgtcaaactt    4200
tgccttcaac tgttttattt tctagtctct tccactttaa aacaaaatga acactgcttg    4260
tcttcttcca ttgaccattt agtgttgagt actgtatgtg ttttgttaat tctataaagg    4320
tatctgttag atattaaagg tgagaattag ggcaggttaa tcaaaaatgg ggaaggggaa    4380
atggtaacca aaaagtaacc ccatggtaag gtttatatga gtatatgtga atatagagct    4440
aggaaaaaaa gccccccccaa ataccttttt aacccctctg attggctatt attactatat    4500
```

```
ttattattat ttattgaaac cttagggaag attgaagatt catcccatac ttctatatac    4560
catgcttaaa aatcacgtca ttctttaaac aaaaatactc aagatcattt atatttattt    4620
ggagagaaaa ctgtcctaat ttagaatttc cctcaaatct gagggacttt taagaaatgc    4680
taacagattt ttctggagga aatttagaca aaacaatgtc atttagtaga atatttcagt    4740
atttaagtgg aatttcagta tactgtacta tcctttataa gtcattaaaa taatgtttca    4800
tcaaatggtt aaatggacca ctggtttctt agagaaatgt ttttaggctt aattcattca    4860
attgtcaagt acacttagtc ttaatacact caggtttgaa cagattattc tgaatattaa    4920
aatttaatcc attcttaata ttttaaaact tttgttaaga aaaactgcca gtttgtgctt    4980
ttgaaatgtc tgttttgaca tcatagtcta gtaaaatttt gacagtgcat atgtactgtt    5040
actaaaagct ttatatgaaa ttattaatgt gaagttttc atttataatt caaggaagga    5100
tttcctgaaa acatttcaag ggatttatgt ctacatattt gtgtgtgtgt gtgtatatat    5160
atgtaatatg catacacaga tgcatatgtg tatatataat gaaatttatg ttgctggtat    5220
tttgcatttt aaagtgatca agattcatta ggcaaacttt ggtttaagta aacatatgtt    5280
caaaatcaga ttaacagata caggtttcat agagaacaaa ggtgatcatt tgaagggcat    5340
gctgtaattt cacacaattt tccagttcaa aaatggagaa tacttcgcct aaaatactgt    5400 taagtggggtt aattgataca agtttctgtg gtggaaaatt tatgcaggtt ttcacgaatc    5460 ctttttttttt tttttttttt tttttgagac ggagtcttgc tctgttgcca cgctggaatg    5520
cagtaacgtg atcttggctc actgcgacct ccacctcccc agttcaagcg attctcctgc    5580
ctcagcctcc ctagtagctg ggactacggg tgcacgccac catgcccagc taattttttgt    5640 attttgagta gagacagggt ttcaccgtgt tggctaggat ggtgtctatc tcttgacctt    5700
gtgatccacc cgcctcagcc tcccagagtg ctgggattac aggtgcgagc cactgcgcct    5760
ggctggtttt catgaatctt gatagacatc tataacgtta ttattttcag tggtgtgcag    5820 cattttttgct tcatgagtat gacctaggta tagagatctg ataacttgaa ttcagaatat    5880
taagaaaatg aagtaactga ttttctaaaa aaaaaaaaa aaaaaatttc tacattataa    5940
ctcacagcat tgttccattg caggttttgc aatgtttggg ggtaaagaca gtagaaatat    6000
tattcagtaa acaataatgt gtgaactttt aagatggata atagggcatg gactgagtgc    6060
tgctatcttg aaatgtgcac aggtacactt acctttttttt ttttttttttt taagttttttc    6120 ccattcagga aaacaacatt gtgatctgta ctacaggaac caaatgtcat gcgtcataca    6180
tgtgggtata aagtacataa aatatatcta actattcata atgtggggtg ggtaatactg    6240
tctgtgaaat aatgtaagaa gcttttcact taaaaaaaat gcattacttt cacttaacac    6300
tagacaccag gtcgaaaatt ttcaaggtta tagtacttat ttcaacaatt cttagagatg    6360
ctagctagtg ttgaagctaa aaatagcttt atttatgctg aattgtgatt ttttttatgcc    6420 aaattttttt tagttctaat cattgatgat agcttggaaa taaataatta tgccatggca    6480
tttgacagtt cattattcct ataagaatta aattgagttt agagagaatg gtggtgttga    6540
gctgattatt aacagttact gaaatcaaat atttatttgt tacattattc catttgtatt    6600
ttaggtttcc ttttacattc ttttttatatg cattctgaca ttacatattt tttaagacta    6660
tggaaataat ttaaagattt aagctctggt ggatgattat ctgctaagta agtctgaaaa    6720 tgtaatatt tgataatact gtaatatacc tgtcacacaa atgcttttct aatgttttaa    6780
ccttgagtat tgcagttgct gctttgtaca gaggttactg caataaagga agtggattca    6840
ttaaacctat ttaatgtcca aaaaaaaaaa aaaaaaaaa aaaaaaaaa a                6891
```

<210> SEQ ID NO 134
<211> LENGTH: 3959
<212> TYPE: DNA
<213> ORGANISM: Homo sapiens

<400> SEQUENCE: 134

```
ataaaagctg cccggggaag ccaggagagc gaagggcgga cgtactcgcc acggcaccca      60
ggctgcgcgc acgcggtccc ggtgtgcagc tggagagcga gcggccaccg ggagcccccg     120
gcacagcccg cgcccgcccc gcaggagccc gcgaagatgc cccggcgcag cctgcacgcg     180
gcggccgtgc tcctgctggt gatcttaaag gaacagcctt ccagcccggc cccagtgaac     240
ggttccaagt ggacttattt tggtcctgat ggggagaata gctggtccaa gaagtacccg     300
tcgtgtgggg gcctgctgca gtcccccata gacctgcaca gtgacatcct ccagtatgac     360
gccagcctca cgcccctcga gttccaaggc tacaatctgt ctgccaacaa gcagtttctc     420
ctgaccaaca atggccattc agtgaagctg aacctgccct cggacatgca catccagggc     480
ctccagtctc gctacagtgc cacgcagctg cacctgcact gggggaaccc gaatgacccg     540
cacggctctg agcacaccgt cagcggacag cacttcgccg ccgagctgca cattgtccat     600
tataactcag acctttatcc tgacgccagc actgccagca caagtcaga aggcctcgct     660
gtcctggctg ttctcattga gatgggctcc ttcaatccgt cctatgacaa gatcttcagt     720
cacattcaac atgtaaagta caaaggccag gaagcattcg tcccgggatt caacattgaa     780
gagctgcttc cggagaggac cgctgaatat taccgctacc ggggtccct gaccacaccc     840
ccttgcaacc ccactgtgct ctggacagtt ttccgaaacc ccgtgcaaat ttcccaggag     900
cagctgctgg ctttggagac agccctgtac tgcacacaca tggacgaccc tttccccaga     960
gaaatgatca acaacttccg gcaggtccag aagttcgatg agaggctggt atacacctcc    1020
ttctcccaag gcatcatcct ctcactggcc ctggctggca ttcttggcat ctgtattgtg    1080
gtggtggtgt ccatttggct tttcagaagg aagagtatca aaaaggtga taacaaggga    1140
gtcatttaca agccagccac caagatggag actgaggccc acgcttgagg tccccggagc    1200
tcccgggcac atccaggaag gaccttgctt tggaccctac acacttcggc tctctggaca    1260
cttgcgacac ctcaaggtgt tctctgtagc tcaatctgca aacatgccag gcctcaggga    1320
tcctctgctg ggtgcctcct tgccttggga ccatggccac cccagagcca tccgatcgat    1380
ggatgggatg cactctcaga ccaagcagca ggaattcaaa gctgcttgct gtaactgtgt    1440
gagattgtga agtggtctga attctggaat cacaaaccaa gccatgctgg tgggccatta    1500
atggttggaa aacactttca tccggggctt tgccagagcg tgctttcaag tgtcctggaa    1560
attctgctgc ttctccaagc tttcagacaa gaatgtgcac tctctgctta ggttttgctt    1620
gggaaactca acttctttcc tctggagacg gggcatctcc ctctgatttc cttctgctat    1680
gacaaaacct ttaatctgca ccttacaact cggggacaaa tggggacagg aaggatcaag    1740
ttgtagagag aaaaagaaaa caagagatat acattgtgat atattaggga cactttcaca    1800
gtcctgtcct ctggatcaca gacactgcac agaccttagg gaatggcagg ttcaagttcc    1860
acttcttggt ggggatgaga agggagagag agctagaggg acaaagagaa tgagaagaca    1920
tggatgatct gggagagtct cactttggaa tcagaattgg aatcacattc tgtttatcaa    1980
gccataatgt aaggacagaa taatacaata ttaagtccaa atccaacctc ctgtcagtgg    2040
agcagttatg ttttatactc tacagatttt acaaataatg aggctgttcc ttgaaaatgt    2100
```

```
gttgttgctg tgtcctggag gagacatgag ttccgagatg acccaatctg cctttgaatc    2160
tggaggaaat aggcagaaac aaaatgactg tagaacttat tctctgtagg ccaaatttca    2220
tttcagccac ttctgcagga tccctactgc caacctggaa tggagacttt tatctacttc    2280
tctctctctg aagatgtcaa atcgtggttt agatcaaata tatttcaagc tataaaagca    2340
ggaggttatc tgtgcagggg gctggcatca tgtatttagg ggcaagtaat aatggaatgc    2400
tactaagata ctccatattc ttccccgaat cacacagaca gtttctgaca ggcgcaactc    2460
ctccattttc ctcccgcagg tgagaaccct gtggagatga gtcagtgcca tgactgagaa    2520
ggaaccgacc cctagttgag agcaccttgc agttccccga gaactttctg attcacagtc    2580
tcattttgac agcatgaaat gtcctcttga agcatagctt tttaaatatc ttttccttc    2640 tactcctccc tctgactcta agaattctct cttctggaat cgcttgaacc caggaggcgg    2700
aggttgcagt aagccaaggt catgccactg cactctagcc tgggtgacag agcgagactc    2760
catctcaaaa aaaaaaaaa aaaaattatt ctgtaccatc acaactttc acaacgatgg    2820 caagccttat gtcttgggag cctgttttgc taggcaaagt tacaagtgac ctaatgggag    2880
ctcaaatgtg tgtgtgtctc tctgtgtgtt tgtgtgtgtg tgtgcactca agacctctaa    2940
cagcctcgaa gcctggggtg gcatcccggc cttgccatta gcatgcctca tgcatcatca    3000
gatgacaagg acaaccctca tgacgaagca acatgaatta gggggcctct tggccttggt    3060
ccaaaattgt caatcagaaa tgaacataaa ggactccaga gcagtgggac tgtctgtcaa    3120
aagactctgt atatcttttg tggatgagtt ttgtgagaga acagagagac cattgtacct    3180
ggcacaaggg ctgttcatga aaagggagac ttactgggag gtgcaagaca gtggcatttc    3240
tcctctcctc ttgctgctca gcacagcccc ggattgcagc cccgaggctg agaccagaca    3300
aagcccggga ggcagaaaga tgctccaaga accaacacta tcaatgtctt tgcaaatcct    3360
cacaggattc ctgtgggtcc agcttttgaa ctgggaaacc tttcttcgga tccgcactca    3420
ttccactgat gccagctgcc cctgaaggat gccagtactg tggtgtgtga gtctcagcag    3480
ccgcccacac gctcctaact ctgctgcatg gcagatgcct aggtggaaat agcaaaaaca    3540
aggcccaggc tggggccagg gccagagggg aaggccctgg attctcactc atgtgagatc    3600
ttgaatctct ttcttttgttc tgtttgtttta gttagtatca tctggtaaaa tagttaaaaa    3660
acaacaaaaa actctgtatc tgtttctagc atgtgctgca ttgactctat taatcacatt    3720
tcaaattcac cctacattcc tctcctcttc actagcctct ctgaaggtgt cctggccagc    3780
cctggagaag cactggtgtc tgcagcaccc ctcagttcct gtgcctcagc ccacaggcca    3840
ctgtgataat ggtctgttta gcacttctgt atttattgta agaatgatta taatgaagat    3900
acacactgta actacaagaa attataaatg tttttcacat caaaaaaaaa aaaaaaaaa    3959
```

<210> SEQ ID NO 135
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 135

```
gacctgagca ctggcataa                                                   19
```

<210> SEQ ID NO 136
<211> LENGTH: 19
<212> TYPE: DNA
<213> ORGANISM: Artificial Sequence -continued

```
<220> FEATURE:
<223> OTHER INFORMATION: TARGETING SEQUENCE

<400> SEQUENCE: 136
tgacatcgac actcataca                                                19

<210> SEQ ID NO 137
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 137
acactcatac agccaagta                                                19

<210> SEQ ID NO 138
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 138
acaatggtca tgctttcaa                                                19

<210> SEQ ID NO 139
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 139
aggacaaagc agtgctcaa                                                19

<210> SEQ ID NO 140
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 140
gatggcactt acagattga                                                19

<210> SEQ ID NO 141
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 141
gcacttacag attgattca                                                19

<210> SEQ ID NO 142
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 142
acagattgat tcagtttca                                                19
```

```
<210> SEQ ID NO 143
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 143
acaaggttca gagcatact                                               19

<210> SEQ ID NO 144
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 144
cagaacttca cttggttca                                               19

<210> SEQ ID NO 145
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 145
actggccgtt ctaggtatt                                               19

<210> SEQ ID NO 146
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 146
ttgaaggttg gcagcgcta                                               19

<210> SEQ ID NO 147
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 147
tgaaggttgg cagcgctaa                                               19

<210> SEQ ID NO 148
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 148
ttgttgatgt gctggattc                                               19

<210> SEQ ID NO 149
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 149
gaaattccgt aaacttaac                                                    19

<210> SEQ ID NO 150
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 150
ccgaagaact gatggtgga                                                    19

<210> SEQ ID NO 151
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 151
gaactgatgg tggacaact                                                    19

<210> SEQ ID NO 152
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 152
tgaagaacag gcaaatcaa                                                    19

<210> SEQ ID NO 153
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 153
cttacttgat agacttact                                                    19

<210> SEQ ID NO 154
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 154
tgtgaagact agaccaatt                                                    19

<210> SEQ ID NO 155
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 155
ttgagctagt taaggcaaa                                                    19

<210> SEQ ID NO 156
```

-continued

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 156
acactggtgc tacgaggtt                                                      19

<210> SEQ ID NO 157
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 157
ctggtgctac gaggttcaa                                                      19

<210> SEQ ID NO 158
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 158
gttcaagccg agtcctcca                                                      19

<210> SEQ ID NO 159
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 159
ttcaagccga gtcctccaa                                                      19

<210> SEQ ID NO 160
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 160
cctgcttggt gccagtcaa                                                      19

<210> SEQ ID NO 161
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 161
tctctggcta cgataagaa                                                      19

<210> SEQ ID NO 162
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 162
```

```
tggctacgat aagaagcaa                                                      19

<210> SEQ ID NO 163
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 163
gcaaacgtgg actgtccaa                                                      19

<210> SEQ ID NO 164
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 164
tggtccgact tgccatata                                                      19

<210> SEQ ID NO 165
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 165
ccatggagat gcacatagt                                                      19

<210> SEQ ID NO 166
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 166
agatgcacat agtacatga                                                      19

<210> SEQ ID NO 167
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 167
tgcacatagt acatgagaa                                                      19

<210> SEQ ID NO 168
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 168
atagtacatg agaaagaga                                                      19

<210> SEQ ID NO 169
<211> LENGTH: 19
<212> TYPE: DNA
```

```
<213> ORGANISM: Artificial Sequence
<220> FEATURE:
<223> OTHER INFORMATION: TARGETING SEQUENCE

<400> SEQUENCE: 169
catcgaggaa tgtgaaaga                                                19

<210> SEQ ID NO 170
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 170
ttgcggtgct ggcctttct                                                19

<210> SEQ ID NO 171
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 171
gaacagatcc tggcattct                                                19

<210> SEQ ID NO 172
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 172
tctctcagaa gctgtacta                                                19

<210> SEQ ID NO 173
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 173
aggaacagac agtgagcat                                                19

<210> SEQ ID NO 174
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 174
gaacagacag tgagcatga                                                19

<210> SEQ ID NO 175
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 175
ggcagcgcac ggtgataaa                                                19
```

```
<210> SEQ ID NO 176
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 176
cagcctctct gttgcctca                                                19

<210> SEQ ID NO 177
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 177
tgttgcctca gctctccaa                                                19

<210> SEQ ID NO 178
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 178
ttcaatccgt cctatgaca                                                19

<210> SEQ ID NO 179
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 179
agagcgtgct ttcaagtgt                                                19

<210> SEQ ID NO 180
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 180
gatgtcaaat cgtggttta                                                19

<210> SEQ ID NO 181
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 181
aaatcgtggt ttagatcaa                                                19

<210> SEQ ID NO 182
<211> LENGTH: 19
<212> TYPE: DNA
<213> ORGANISM: Artificial Sequence
<220> FEATURE:
```

```
<223> OTHER INFORMATION: TARGETING SEQUENCE

<400> SEQUENCE: 182
atggaatgct actaagata                                                19

<210> SEQ ID NO 183
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 183
ctactaagat actccatat                                                19

<210> SEQ ID NO 184
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 184
acaacgatgg caagcctta                                                19

<210> SEQ ID NO 185
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 185
caacgatggc aagccttat                                                19

<210> SEQ ID NO 186
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 186
ttgctaggca aagttacaa                                                19

<210> SEQ ID NO 187
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 187
taggcaaagt tacaagtga                                                19

<210> SEQ ID NO 188
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 188
agttacaagt gacctaatg                                                19
```

```
<210> SEQ ID NO 189
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 189
tgtgcactca agacctcta                                                  19

<210> SEQ ID NO 190
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 190
gtgcactcaa gacctctaa                                                  19

<210> SEQ ID NO 191
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 191
tgcactcaag acctctaac                                                  19

<210> SEQ ID NO 192
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 192
gcactcaaga cctctaaca                                                  19

<210> SEQ ID NO 193
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 193
agacctctaa cagcctcga                                                  19

<210> SEQ ID NO 194
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 194
gacctctaac agcctcgaa                                                  19

<210> SEQ ID NO 195
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 195
tgccattagc atgcctcat                                          19

<210> SEQ ID NO 196
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 196
gccattagca tgcctcatg                                          19

<210> SEQ ID NO 197
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 197
tagcatgcct catgcatca                                          19

<210> SEQ ID NO 198
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 198
catcatcaga tgacaagga                                          19

<210> SEQ ID NO 199
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 199
ctccttcaat ccgtcctat                                          19

<210> SEQ ID NO 200
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 200
agagcgtgct ttcaagtgt                                          19

<210> SEQ ID NO 201
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 201
gatgtcaaat cgtggttta                                          19

<210> SEQ ID NO 202
<211> LENGTH: 19
```

```
<212> TYPE: DNA
<213> ORGANISM: Artificial Sequence
<220> FEATURE:
<223> OTHER INFORMATION: TARGETING SEQUENCE

<400> SEQUENCE: 202
aaatcgtggt ttagatcaa                                                19

<210> SEQ ID NO 203
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 203
atggaatgct actaagata                                                19

<210> SEQ ID NO 204
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 204
ctactaagat actccatat                                                19

<210> SEQ ID NO 205
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 205
acaacgatgg caagcctta                                                19

<210> SEQ ID NO 206
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 206
caacgatggc aagccttat                                                19

<210> SEQ ID NO 207
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 207
ttgctaggca aagttacaa                                                19

<210> SEQ ID NO 208
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 208
```

| | |
|---|---|
| taggcaaagt tacaagtga | 19 |

<210> SEQ ID NO 209
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 209

| | |
|---|---|
| agttacaagt gacctaatg | 19 |

<210> SEQ ID NO 210
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 210

| | |
|---|---|
| tgtgcactca agacctcta | 19 |

<210> SEQ ID NO 211
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 211

| | |
|---|---|
| gtgcactcaa gacctctaa | 19 |

<210> SEQ ID NO 212
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 212

| | |
|---|---|
| tgcactcaag acctctaac | 19 |

<210> SEQ ID NO 213
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 213

| | |
|---|---|
| gcactcaaga cctctaaca | 19 |

<210> SEQ ID NO 214
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 214

| | |
|---|---|
| agacctctaa cagcctcga | 19 |

<210> SEQ ID NO 215
<211> LENGTH: 19
<212> TYPE: DNA
<213> ORGANISM: Artificial Sequence

```
<220> FEATURE:
<223> OTHER INFORMATION: TARGETING SEQUENCE

<400> SEQUENCE: 215
gacctctaac agcctcgaa                                                    19

<210> SEQ ID NO 216
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 216
tgccattagc atgcctcat                                                    19

<210> SEQ ID NO 217
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 217
gccattagca tgcctcatg                                                    19

<210> SEQ ID NO 218
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 218
tagcatgcct catgcatca                                                    19

<210> SEQ ID NO 219
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 219
catcatcaga tgacaagga                                                    19

<210> SEQ ID NO 220
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 220
gcaatgtgct ggtgatcgt                                                    19

<210> SEQ ID NO 221
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 221
tgatcgtggc catcgccaa                                                    19
```

```
<210> SEQ ID NO 222
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 222
aagtgctgcg acttcgtca                                           19

<210> SEQ ID NO 223
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 223
cgtccgtagt ctccttcta                                           19

<210> SEQ ID NO 224
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 224
ccgtagtctc cttctacgt                                           19

<210> SEQ ID NO 225
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 225
atcatggcct tcgtgtacc                                           19

<210> SEQ ID NO 226
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 226
tcatggcctt cgtgtacct                                           19

<210> SEQ ID NO 227
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 227
cctcggaatc caaggtgta                                           19

<210> SEQ ID NO 228
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 228
tgtgtttact taagaccga                                                  19

<210> SEQ ID NO 229
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 229
gtgtttactt aagaccgat                                                  19

<210> SEQ ID NO 230
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 230
gtttacttaa gaccgatag                                                  19

<210> SEQ ID NO 231
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 231
tttacttaag accgatagc                                                  19

<210> SEQ ID NO 232
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 232
ttacttaaga ccgatagca                                                  19

<210> SEQ ID NO 233
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 233
taagaccgat agcaggtga                                                  19

<210> SEQ ID NO 234
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 234
accgatagca ggtgaactc                                                  19

<210> SEQ ID NO 235
```

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 235
cgatagcagg tgaactcga                                                   19

<210> SEQ ID NO 236
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 236
atagcaggtg aactcgaag                                                   19

<210> SEQ ID NO 237
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 237
cacaatcctc gtctgaatc                                                   19

<210> SEQ ID NO 238
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 238
acaatcctcg tctgaatca                                                   19

<210> SEQ ID NO 239
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 239
tcatccgagg caaagagaa                                                   19

<210> SEQ ID NO 240
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 240
catccgaggc aaagagaaa                                                   19

<210> SEQ ID NO 241
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 241
```
ccacggaccg ttgcacaaa                                         19

<210> SEQ ID NO 242
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 242
cacgacgtca cgcagcaaa                                         19

<210> SEQ ID NO 243
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 243
gatcgctact ttgccatta                                         19

<210> SEQ ID NO 244
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 244
atcgctactt tgccattac                                         19

<210> SEQ ID NO 245
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 245
tcgctacttt gccattact                                         19

<210> SEQ ID NO 246
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 246
gccattactt cacctttca                                         19

<210> SEQ ID NO 247
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 247
ttacttcacc tttcaagta                                         19

<210> SEQ ID NO 248
<211> LENGTH: 19
<212> TYPE: DNA

-continued

```
<213> ORGANISM: Artificial Sequence
<220> FEATURE:
<223> OTHER INFORMATION: TARGETING SEQUENCE

<400> SEQUENCE: 248
ccattcagat gcactggta                                              19

<210> SEQ ID NO 249
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 249
tgatcatggt cttcgtcta                                              19

<210> SEQ ID NO 250
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 250
agacgttagg catcatcat                                              19

<210> SEQ ID NO 251
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 251
tcgttaacat tgtgcatgt                                              19

<210> SEQ ID NO 252
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 252
aggataacct catccgtaa                                              19

<210> SEQ ID NO 253
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 253
tcatccgtaa ggaagttta                                              19

<210> SEQ ID NO 254
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 254
aagtttacat cctcctaaa                                              19
```

```
<210> SEQ ID NO 255
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 255
agtttacatc ctcctaaat                                                  19

<210> SEQ ID NO 256
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 256
taaattggat aggctatgt                                                  19

<210> SEQ ID NO 257
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 257
ctatgtcaat tctggtttc                                                  19

<210> SEQ ID NO 258
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 258
ggtactgtgc ctagcgata                                                  19

<210> SEQ ID NO 259
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 259
gtactgtgcc tagcgataa                                                  19

<210> SEQ ID NO 260
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 260
tactgtgcct agcgataac                                                  19

<210> SEQ ID NO 261
<211> LENGTH: 19
<212> TYPE: DNA
<213> ORGANISM: Artificial Sequence
<220> FEATURE:
```

```
<223> OTHER INFORMATION: TARGETING SEQUENCE

<400> SEQUENCE: 261
gcgataacat tgattcaca                                                19

<210> SEQ ID NO 262
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 262
cgataacatt gattcacaa                                                19

<210> SEQ ID NO 263
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 263
ggaggaattg tagtacaaa                                                19

<210> SEQ ID NO 264
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 264
gaggaattgt agtacaaat                                                19

<210> SEQ ID NO 265
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 265
aggaattgta gtacaaatg                                                19

<210> SEQ ID NO 266
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 266
caaatgactc actgctgta                                                19

<210> SEQ ID NO 267
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 267
gacctgagtc tgctatatt                                                19
```

```
<210> SEQ ID NO 268
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 268
acctgagtct gctatattt                                                      19

<210> SEQ ID NO 269
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 269
ccatgtatct acctcacta                                                      19

<210> SEQ ID NO 270
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 270
catgtatcta cctcactat                                                      19

<210> SEQ ID NO 271
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 271
atgtatctac ctcactatt                                                      19

<210> SEQ ID NO 272
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 272
cctcactatt caagtatta                                                      19

<210> SEQ ID NO 273
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 273
taatatattg ctgctggta                                                      19

<210> SEQ ID NO 274
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 274
aatatattgc tgctggtaa                                              19

<210> SEQ ID NO 275
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 275
atatattgct gctggtaat                                              19

<210> SEQ ID NO 276
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 276
tatattgctg ctggtaatt                                              19

<210> SEQ ID NO 277
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 277
ctggtaattt gtatctgaa                                              19

<210> SEQ ID NO 278
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 278
gagtatctcg gacctttca                                              19

<210> SEQ ID NO 279
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 279
cggacctttc agctgtgaa                                              19

<210> SEQ ID NO 280
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 280
cgagcaaagg tctaaagtt                                              19

<210> SEQ ID NO 281
<211> LENGTH: 19
```

```
<212> TYPE: DNA
<213> ORGANISM: Artificial Sequence
<220> FEATURE:
<223> OTHER INFORMATION: TARGETING SEQUENCE

<400> SEQUENCE: 281
gagcaaaggt ctaaagttt                                                    19

<210> SEQ ID NO 282
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 282
ggtctaaagt ttacagtaa                                                    19

<210> SEQ ID NO 283
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 283
agtgtctgct accaatatg                                                    19

<210> SEQ ID NO 284
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 284
agacaacgag tctctcatc                                                    19

<210> SEQ ID NO 285
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 285
ggctgtggtc ctgcattac                                                    19

<210> SEQ ID NO 286
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 286
cttcctcctc aaaccgaga                                                    19

<210> SEQ ID NO 287
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 287
```

-continued

| | |
|---|---|
| tcctcctcaa accgagaga | 19 |

<210> SEQ ID NO 288
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 288

| | |
|---|---|
| cctcaaaccg agagactca | 19 |

<210> SEQ ID NO 289
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 289

| | |
|---|---|
| tcaaaccgag agactcaca | 19 |

<210> SEQ ID NO 290
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 290

| | |
|---|---|
| aaaccgagag actcacact | 19 |

<210> SEQ ID NO 291
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 291

| | |
|---|---|
| ccacgccttt gttgtttga | 19 |

<210> SEQ ID NO 292
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 292

| | |
|---|---|
| cacgcctttg ttgtttgaa | 19 |

<210> SEQ ID NO 293
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 293

| | |
|---|---|
| acgcctttgt tgtttgaat | 19 |

<210> SEQ ID NO 294
<211> LENGTH: 19
<212> TYPE: DNA
<213> ORGANISM: Artificial Sequence

```
<220> FEATURE:
<223> OTHER INFORMATION: TARGETING SEQUENCE

<400> SEQUENCE: 294
ggctataacg gtcaaccat                                                    19

<210> SEQ ID NO 295
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 295
tataacggtc aaccatttc                                                    19

<210> SEQ ID NO 296
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 296
cggtcaacca tttctgtct                                                    19

<210> SEQ ID NO 297
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 297
gtcaaccatt tctgtctct                                                    19

<210> SEQ ID NO 298
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 298
ccgtcttccg gtcattctt                                                    19

<210> SEQ ID NO 299
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 299
cctctcgtct ttcgcacat                                                    19

<210> SEQ ID NO 300
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 300
tctcgtcttt cgcacattc                                                    19
```

<210> SEQ ID NO 301
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 301
tttcgcacat tctcctgat                                              19

<210> SEQ ID NO 302
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 302
ttcgcacatt ctcctgatc                                              19

<210> SEQ ID NO 303
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 303
agaaccagtt cgaccacta                                              19

<210> SEQ ID NO 304
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 304
aaccagttcg accactaca                                              19

<210> SEQ ID NO 305
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 305
ctgcaaataa actgttaca                                              19

<210> SEQ ID NO 306
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 306
tagacgctac aaccttcca                                              19

<210> SEQ ID NO 307
<211> LENGTH: 19
<212> TYPE: DNA
<213> ORGANISM: Artificial Sequence
<220> FEATURE:
<223> OTHER INFORMATION: TARGETING SEQUENCE -continued

```
<400> SEQUENCE: 307
cgctacaacc ttccagagt                                                19

<210> SEQ ID NO 308
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 308
agagtgtctg ctaccaata                                                19

<210> SEQ ID NO 309
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 309
gagtgtctgc taccaatat                                                19

<210> SEQ ID NO 310
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 310
ctgtcctcgt ctggatcta                                                19

<210> SEQ ID NO 311
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 311
atggccgctt cttggtaca                                                19

<210> SEQ ID NO 312
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 312
cgacatcagt gacgctgtt                                                19

<210> SEQ ID NO 313
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 313
gcacgtgctg cctcaagaa                                                19

<210> SEQ ID NO 314
```

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 314
cacgtgctgc ctcaagaaa                                                    19

<210> SEQ ID NO 315
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 315
gaaagcgtct tccggttct                                                    19

<210> SEQ ID NO 316
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 316
tgtggtagat ggagacttc                                                    19

<210> SEQ ID NO 317
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 317
gacaacgagt ctctcatca                                                    19

<210> SEQ ID NO 318
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 318
aggctgtggt cctgcatta                                                    19

<210> SEQ ID NO 319
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 319
gctgtggtcc tgcattaca                                                    19

<210> SEQ ID NO 320
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 320
```

-continued gtctacgcct acgtctttg                                                19

<210> SEQ ID NO 321
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 321
tctacgccta cgtctttga                                                19

<210> SEQ ID NO 322
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 322
ctacgcctac gtctttgaa                                                19

<210> SEQ ID NO 323
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 323
cggctacgag atcgagttc                                                19

<210> SEQ ID NO 324
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 324
cagcgactga tgcgatact                                                19

<210> SEQ ID NO 325
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 325
ggctcagcag tacgttagt                                                19

<210> SEQ ID NO 326
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 326
agtacgttag tctggacct                                                19

<210> SEQ ID NO 327
<211> LENGTH: 19
<212> TYPE: DNA

-continued

```
<213> ORGANISM: Artificial Sequence
<220> FEATURE:
<223> OTHER INFORMATION: TARGETING SEQUENCE

<400> SEQUENCE: 327
acatggtgca ctggaagaa                                                19

<210> SEQ ID NO 328
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 328
agaaccagtt cgaccacta                                                19

<210> SEQ ID NO 329
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 329
gaaccagttc gaccactac                                                19

<210> SEQ ID NO 330
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 330
ggctataaca cagacgagc                                                19

<210> SEQ ID NO 331
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 331
gctataacac agacgagcc                                                19

<210> SEQ ID NO 332
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 332
gctgcaaata aactgttac                                                19

<210> SEQ ID NO 333
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 333
ctgcaaataa actgttaca                                                19
```

```
<210> SEQ ID NO 334
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 334
gcaatgagac cgtggaaga                                               19

<210> SEQ ID NO 335
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 335
tgccaaggcc tgcgtagta                                               19

<210> SEQ ID NO 336
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 336
taaaggacat gacctccga                                               19

<210> SEQ ID NO 337
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 337
agcaagctgc tgacatgat                                               19

<210> SEQ ID NO 338
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 338
acatgattct tctggatga                                               19

<210> SEQ ID NO 339
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 339
gtcgtctgat ctttgataa                                               19

<210> SEQ ID NO 340
<211> LENGTH: 19
<212> TYPE: DNA
<213> ORGANISM: Artificial Sequence
<220> FEATURE:
```

<223> OTHER INFORMATION: TARGETING SEQUENCE

<400> SEQUENCE: 340
cttatacctt aaccagtaa                                                    19

<210> SEQ ID NO 341
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 341
ggatcaacga tgtggaaga                                                    19

<210> SEQ ID NO 342
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 342
acgatgtgga agacagcta                                                    19

<210> SEQ ID NO 343
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 343
ccgacttggt catctgtaa                                                    19

<210> SEQ ID NO 344
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 344
taggaaagca ccgcagcat                                                    19

<210> SEQ ID NO 345
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 345
agacgtcctg gaatgaagc                                                    19

<210> SEQ ID NO 346
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 346
gacgtcctgg aatgaagca                                                    19

```
<210> SEQ ID NO 347
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 347
acgtcctgga atgaagcat                                                   19

<210> SEQ ID NO 348
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 348
gaagcatgta gctctatgg                                                   19

<210> SEQ ID NO 349
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 349
ttcagaacaa ggtgataaa                                                   19

<210> SEQ ID NO 350
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 350
tgatgaactt catcgtaaa                                                   19

<210> SEQ ID NO 351
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 351
ggtgctatca gccgttgta                                                   19

<210> SEQ ID NO 352
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 352
tcagccgttg taatcataa                                                   19

<210> SEQ ID NO 353
<211> LENGTH: 19
<212> TYPE: DNA
<213> ORGANISM: Artificial Sequence
<220> FEATURE:
<223> OTHER INFORMATION: TARGETING SEQUENCE
```

-continued

<400> SEQUENCE: 353
gattcgaaat ggtgagaaa					19

<210> SEQ ID NO 354
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 354
cagaatcata tctgcaaat					19

<210> SEQ ID NO 355
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 355
cacgtggtat tgttgtcta					19

<210> SEQ ID NO 356
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 356
ctgcttagtg aagaactta					19

<210> SEQ ID NO 357
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 357
gtttcaggct aaccaggaa					19

<210> SEQ ID NO 358
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 358
cactcttaaa gtgcataga					19

<210> SEQ ID NO 359
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 359
agtaccagtt gtctattca					19

<210> SEQ ID NO 360
<211> LENGTH: 19

```
<212> TYPE: DNA
<213> ORGANISM: Artificial Sequence
<220> FEATURE:
<223> OTHER INFORMATION: TARGETING SEQUENCE

<400> SEQUENCE: 360
taccagttgt ctattcata                                                  19

<210> SEQ ID NO 361
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 361
agctgaaaga cgcctttca                                                  19

<210> SEQ ID NO 362
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 362
tcgataatct gtgctttgt                                                  19

<210> SEQ ID NO 363
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 363
acaggagacc atccaatca                                                  19

<210> SEQ ID NO 364
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 364
tagccttgat gaacttcat                                                  19

<210> SEQ ID NO 365
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 365
ttgatgaact tcatcgtaa                                                  19

<210> SEQ ID NO 366
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 366
```

-continued

| | |
|---|---|
| gatgaacttc atcgtaaat | 19 |

<210> SEQ ID NO 367
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 367

| | |
|---|---|
| ctactcctga atggatcaa | 19 |

<210> SEQ ID NO 368
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 368

| | |
|---|---|
| ggagcgattc tttgtttct | 19 |

<210> SEQ ID NO 369
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 369

| | |
|---|---|
| gtgctatcag ccgttgtaa | 19 |

<210> SEQ ID NO 370
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 370

| | |
|---|---|
| tgctatcagc cgttgtaat | 19 |

<210> SEQ ID NO 371
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 371

| | |
|---|---|
| gagcataaat gcggaggaa | 19 |

<210> SEQ ID NO 372
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 372

| | |
|---|---|
| gaaggcaatg gacctatga | 19 |

<210> SEQ ID NO 373
<211> LENGTH: 19
<212> TYPE: DNA
<213> ORGANISM: Artificial Sequence

```
<220> FEATURE:
<223> OTHER INFORMATION: TARGETING SEQUENCE

<400> SEQUENCE: 373
ccgacttggt catctgtaa                                                    19

<210> SEQ ID NO 374
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 374
tatatgacga agtcagaaa                                                    19

<210> SEQ ID NO 375
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 375
tggcaatgga tgaccacaa                                                    19

<210> SEQ ID NO 376
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 376
tgaaccatcc aacgacaat                                                    19

<210> SEQ ID NO 377
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 377
accatccaac gacaatcta                                                    19

<210> SEQ ID NO 378
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 378
catccaacga caatctata                                                    19

<210> SEQ ID NO 379
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 379
atccaacgac aatctatat                                                    19
```

-continued

<210> SEQ ID NO 380
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 380
gcagatcaac gcagaggaa                                          19

<210> SEQ ID NO 381
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 381
tgtttcttct ccaccaact                                          19

<210> SEQ ID NO 382
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 382
ccatagcaat ggagattga                                          19

<210> SEQ ID NO 383
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 383
agatgcaaga tgcctttca                                          19

<210> SEQ ID NO 384
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 384
ctgaatctgc catctggaa                                          19

<210> SEQ ID NO 385
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 385
tgaatctgcc atctggaaa                                          19

<210> SEQ ID NO 386
<211> LENGTH: 19
<212> TYPE: DNA
<213> ORGANISM: Artificial Sequence
<220> FEATURE:
<223> OTHER INFORMATION: TARGETING SEQUENCE

```
<400> SEQUENCE: 386
atcgtctttg ctcgaacgt                                                  19

<210> SEQ ID NO 387
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 387
ctgcattgaa gaaggctga                                                  19

<210> SEQ ID NO 388
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 388
atgaagcggc agccacgaa                                                  19

<210> SEQ ID NO 389
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 389
tgaagcggca gccacgaaa                                                  19

<210> SEQ ID NO 390
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 390
ggatgaccgg accatgaat                                                  19

<210> SEQ ID NO 391
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 391
gctgcctttc tctcttact                                                  19

<210> SEQ ID NO 392
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 392
tctatgatga ggtccgaaa                                                  19

<210> SEQ ID NO 393
```

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 393
gtggagaagg agacatact                                                  19

<210> SEQ ID NO 394
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 394
tggagaagga gacatacta                                                  19

<210> SEQ ID NO 395
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 395
tagacctaac tgtgaacaa                                                  19

<210> SEQ ID NO 396
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 396
agacctaact gtgaacaat                                                  19

<210> SEQ ID NO 397
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 397
tccactatgt tgtctattt                                                  19

<210> SEQ ID NO 398
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 398
tgagtgcaag agcctgaga                                                  19

<210> SEQ ID NO 399
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 399
```
tgacatgagt ctccagata                                              19

<210> SEQ ID NO 400
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 400
gtcgtggact ccagctcta                                              19

<210> SEQ ID NO 401
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 401
tgtcactcat gtacttaat                                              19

<210> SEQ ID NO 402
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 402
gtcactcatg tacttaata                                              19

<210> SEQ ID NO 403
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 403
cacttcacct tctgtaata                                              19

<210> SEQ ID NO 404
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 404
gtagagagag acctagata                                              19

<210> SEQ ID NO 405
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 405
ctagataggt catgcaagt                                              19

<210> SEQ ID NO 406
<211> LENGTH: 19
<212> TYPE: DNA

```
<213> ORGANISM: Artificial Sequence
<220> FEATURE:
<223> OTHER INFORMATION: TARGETING SEQUENCE

<400> SEQUENCE: 406
aggtcatgca agtgagaaa                                                      19

<210> SEQ ID NO 407
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 407
tatcagaagc aaggaagta                                                      19

<210> SEQ ID NO 408
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 408
tccgattaat tggagatta                                                      19

<210> SEQ ID NO 409
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 409
ccgattaatt ggagattac                                                      19

<210> SEQ ID NO 410
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 410
gattactaac tgtggacaa                                                      19

<210> SEQ ID NO 411
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 411
attactaact gtggacaaa                                                      19

<210> SEQ ID NO 412
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 412
tcaggcactt tagaaatat                                                      19
```

<210> SEQ ID NO 413
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 413
ggctaattat catcaatct                                               19

<210> SEQ ID NO 414
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 414
agtttgaggt actacctat                                               19

<210> SEQ ID NO 415
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 415
tactacctat gtacttgaa                                               19

<210> SEQ ID NO 416
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 416
actacctatg tacttgaaa                                               19

<210> SEQ ID NO 417
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 417
tggctatgac agagcacaa                                               19

<210> SEQ ID NO 418
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 418
gaggtctgcc ggaaataca                                               19

<210> SEQ ID NO 419
<211> LENGTH: 19
<212> TYPE: DNA
<213> ORGANISM: Artificial Sequence
<220> FEATURE:

```
<223> OTHER INFORMATION: TARGETING SEQUENCE

<400> SEQUENCE: 419
ctcacgccac cgcctacca                                                19

<210> SEQ ID NO 420
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 420
tcgactgtga tgacgtgaa                                                19

<210> SEQ ID NO 421
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 421
tgaacttcac cacggacaa                                                19

<210> SEQ ID NO 422
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 422
ccaaggcctg cgtgatcca                                                19

<210> SEQ ID NO 423
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 423
ggacttcacc tccgagcaa                                                19

<210> SEQ ID NO 424
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 424
gacttcacct ccgagcaaa                                                19

<210> SEQ ID NO 425
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 425
acttcacctc cgagcaaat                                                19
```

```
<210> SEQ ID NO 426
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 426
tcgacgagat cctgcagaa                                                  19

<210> SEQ ID NO 427
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 427
cgacgagatc ctgcagaat                                                  19

<210> SEQ ID NO 428
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 428
acgagatcct gcagaatca                                                  19

<210> SEQ ID NO 429
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 429
gatcttcgac aacctaaag                                                  19

<210> SEQ ID NO 430
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 430
ccatctcact ggcgtacga                                                  19

<210> SEQ ID NO 431
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 431
ctgccgaaag cgacatcat                                                  19

<210> SEQ ID NO 432
<211> LENGTH: 19
<212> TYPE: DNA
<213> ORGANISM: Artificial Sequence
<220> FEATURE:
<223> OTHER INFORMATION: TARGETING SEQUENCE
```

-continued

<400> SEQUENCE: 432
cggacaaatt ggtcaatga                                              19

<210> SEQ ID NO 433
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 433
caaattggtc aatgagaga                                              19

<210> SEQ ID NO 434
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 434
ggatgaccgc accgtcaat                                              19

<210> SEQ ID NO 435
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 435
caccgtcaat gacctggaa                                              19

<210> SEQ ID NO 436
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 436
atcttcgtct acgacgaaa                                              19

<210> SEQ ID NO 437
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 437
ctacgacgaa atccgcaaa                                              19

<210> SEQ ID NO 438
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 438
acgacgaaat ccgcaaact                                              19

<210> SEQ ID NO 439
<211> LENGTH: 19

```
<212> TYPE: DNA
<213> ORGANISM: Artificial Sequence
<220> FEATURE:
<223> OTHER INFORMATION: TARGETING SEQUENCE

<400> SEQUENCE: 439
acgaaatccg caaactcat                                                19

<210> SEQ ID NO 440
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 440
ccaaacctct ctcctctct                                                19

<210> SEQ ID NO 441
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 441
ggcacctggt tacgcttca                                                19

<210> SEQ ID NO 442
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 442
catggatgat cacaaatta                                                19

<210> SEQ ID NO 443
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 443
aatcctgact cgagatgga                                                19

<210> SEQ ID NO 444
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 444
cctacagcat ccagatata                                                19

<210> SEQ ID NO 445
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 445
```

```
ccggcttatc tctgcacaa                                            19

<210> SEQ ID NO 446
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 446
agctctgata cctggttta                                            19

<210> SEQ ID NO 447
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 447
gctctgatac ctggtttat                                            19

<210> SEQ ID NO 448
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 448
aggtgatgct tccgagtca                                            19

<210> SEQ ID NO 449
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 449
gtactcaatg aacgatgaa                                            19

<210> SEQ ID NO 450
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 450
tactcaatga acgatgaaa                                            19

<210> SEQ ID NO 451
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 451
gtgctaggct tctgcttct                                            19

<210> SEQ ID NO 452
<211> LENGTH: 19
<212> TYPE: DNA
<213> ORGANISM: Artificial Sequence
```

```
<220> FEATURE:
<223> OTHER INFORMATION: TARGETING SEQUENCE

<400> SEQUENCE: 452
catggtaaca ggagatcat                                                19

<210> SEQ ID NO 453
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 453
tgtggtgcat ggtgcagaa                                                19

<210> SEQ ID NO 454
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 454
tgttcatcat cctcggtat                                                19

<210> SEQ ID NO 455
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 455
gttcatcatc ctcggtata                                                19

<210> SEQ ID NO 456
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 456
ggcttatgag tcagctgaa                                                19

<210> SEQ ID NO 457
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 457
ggacctatga gcaacgaaa                                                19

<210> SEQ ID NO 458
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 458
cggatctcat catctccaa                                                19
```

```
<210> SEQ ID NO 459
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 459
tggctgcatt tctgtccta                                          19

<210> SEQ ID NO 460
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 460
gctgcatttc tgtcctaca                                          19

<210> SEQ ID NO 461
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 461
gtattctcat cttcgtcta                                          19

<210> SEQ ID NO 462
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 462
tattctcatc ttcgtctat                                          19

<210> SEQ ID NO 463
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 463
actaaactca gcagatgaa                                          19

<210> SEQ ID NO 464
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 464
ggccagagat tataagttt                                          19

<210> SEQ ID NO 465
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 465
gccagagatt ataagtttg                                              19

<210> SEQ ID NO 466
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 466
ccagagatta taagtttga                                              19

<210> SEQ ID NO 467
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 467
cagagattat aagtttgac                                              19

<210> SEQ ID NO 468
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 468
ataagtttga cacaacatc                                              19

<210> SEQ ID NO 469
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 469
taagtttgac acaacatct                                              19

<210> SEQ ID NO 470
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 470
tctgagacac taggatgaa                                              19

<210> SEQ ID NO 471
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 471
agacactagg atgaattat                                              19

<210> SEQ ID NO 472
```

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 472
gacactagga tgaattatc                                                  19

<210> SEQ ID NO 473
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 473
aggatgaatt atcttggat                                                  19

<210> SEQ ID NO 474
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 474
gatgaattat cttggatga                                                  19

<210> SEQ ID NO 475
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 475
cgtagccagt ctagacagt                                                  19

<210> SEQ ID NO 476
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 476
gccagtctag acagtaaat                                                  19

<210> SEQ ID NO 477
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 477
cagtctagac agtaaatgt                                                  19

<210> SEQ ID NO 478
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 478
```

```
agacagtaaa tgtctggaa                                                  19

<210> SEQ ID NO 479
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 479
gacagtaaat gtctggaaa                                                  19

<210> SEQ ID NO 480
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 480
gctggattct ttacctact                                                  19

<210> SEQ ID NO 481
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 481
gtggacctat gagcaacga                                                  19

<210> SEQ ID NO 482
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 482
tggacctatg agcaacgaa                                                  19

<210> SEQ ID NO 483
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 483
ggacctatga gcaacgaaa                                                  19

<210> SEQ ID NO 484
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 484
cggatctcat catctccaa                                                  19

<210> SEQ ID NO 485
<211> LENGTH: 19
<212> TYPE: DNA
```

```
<213> ORGANISM: Artificial Sequence
<220> FEATURE:
<223> OTHER INFORMATION: TARGETING SEQUENCE

<400> SEQUENCE: 485
tggctgcatt tctgtccta                                               19

<210> SEQ ID NO 486
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 486
gctgcatttc tgtcctaca                                               19

<210> SEQ ID NO 487
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 487
gtattctcat cttcgtcta                                               19

<210> SEQ ID NO 488
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 488
tattctcatc ttcgtctat                                               19

<210> SEQ ID NO 489
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 489
cttcgtctat gatgaaatc                                               19

<210> SEQ ID NO 490
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 490
actactaaac tcagcagat                                               19

<210> SEQ ID NO 491
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 491
ctactaaact cagcagatg                                               19
```

<210> SEQ ID NO 492
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 492
tactaaactc agcagatga                                           19

<210> SEQ ID NO 493
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 493
actaaactca gcagatgaa                                           19

<210> SEQ ID NO 494
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 494
ggccagagat tataagttt                                           19

<210> SEQ ID NO 495
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 495
gccagagatt ataagtttg                                           19

<210> SEQ ID NO 496
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 496
ccagagatta taagtttga                                           19

<210> SEQ ID NO 497
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 497
cagagattat aagtttgac                                           19

<210> SEQ ID NO 498
<211> LENGTH: 19
<212> TYPE: DNA
<213> ORGANISM: Artificial Sequence
<220> FEATURE:

```
<223> OTHER INFORMATION: TARGETING SEQUENCE

<400> SEQUENCE: 498
ataagtttga cacaacatc                                                19

<210> SEQ ID NO 499
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 499
taagtttgac acaacatct                                                19

<210> SEQ ID NO 500
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 500
tctgagacac taggatgaa                                                19

<210> SEQ ID NO 501
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 501
agacactagg atgaattat                                                19

<210> SEQ ID NO 502
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 502
gacactagga tgaattatc                                                19

<210> SEQ ID NO 503
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 503
taggatgaat tatcttgga                                                19

<210> SEQ ID NO 504
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 504
aggatgaatt atcttggat                                                19
```

```
<210> SEQ ID NO 505
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 505
gatgaattat cttggatga                                               19

<210> SEQ ID NO 506
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 506
tgaattatct tggatgaga                                               19

<210> SEQ ID NO 507
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 507
cgtagccagt ctagacagt                                               19

<210> SEQ ID NO 508
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 508
gccagtctag acagtaaat                                               19

<210> SEQ ID NO 509
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 509
cagtctagac agtaaatgt                                               19

<210> SEQ ID NO 510
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 510
agacagtaaa tgtctggaa                                               19

<210> SEQ ID NO 511
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 511
gacagtaaat gtctggaaa                                                19

<210> SEQ ID NO 512
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 512
acctactagt cttgaacaa                                                19

<210> SEQ ID NO 513
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 513
tactagtctt gaacaaact                                                19

<210> SEQ ID NO 514
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 514
ggacctacac ttaatctat                                                19

<210> SEQ ID NO 515
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 515
gacctacact taatctata                                                19

<210> SEQ ID NO 516
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 516
ctgcatttaa taggttaga                                                19

<210> SEQ ID NO 517
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 517
cgtaactgac ttgtagtaa                                                19

<210> SEQ ID NO 518
<211> LENGTH: 19
```

```
<212> TYPE: DNA
<213> ORGANISM: Artificial Sequence
<220> FEATURE:
<223> OTHER INFORMATION: TARGETING SEQUENCE

<400> SEQUENCE: 518
agcaaggttt gctgtccaa                                                19

<210> SEQ ID NO 519
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 519
tgctgtccaa ggtgtaaat                                                19

<210> SEQ ID NO 520
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 520
gctgtccaag gtgtaaata                                                19

<210> SEQ ID NO 521
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 521
ctgtccaagg tgtaaatat                                                19

<210> SEQ ID NO 522
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 522
ttaacatact ccatagtct                                                19

<210> SEQ ID NO 523
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 523
gccttgtcct ccggtatgt                                                19

<210> SEQ ID NO 524
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 524
```

-continued tgtcctccgg tatgttcta					19

<210> SEQ ID NO 525
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 525
gtcctccggt atgttctaa					19

<210> SEQ ID NO 526
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 526
tcctccggta tgttctaaa					19

<210> SEQ ID NO 527
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 527
ccatcacttt ggctagtga					19

<210> SEQ ID NO 528
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 528
accggtggca gttggttta					19

<210> SEQ ID NO 529
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 529
ccggtggcag ttggtttaa					19

<210> SEQ ID NO 530
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 530
ttggtttaag atccttcta					19

<210> SEQ ID NO 531
<211> LENGTH: 19
<212> TYPE: DNA
<213> ORGANISM: Artificial Sequence

```
<220> FEATURE:
<223> OTHER INFORMATION: TARGETING SEQUENCE

<400> SEQUENCE: 531
agatccttct attctacgt                                                19

<210> SEQ ID NO 532
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 532
atccttctat tctacgtaa                                                19

<210> SEQ ID NO 533
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 533
tccttctatt ctacgtaat                                                19

<210> SEQ ID NO 534
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 534
ccttctattc tacgtaata                                                19

<210> SEQ ID NO 535
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 535
gaaatttcct ttcgtccta                                                19

<210> SEQ ID NO 536
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 536
aacgaggaga ctttaatca                                                19

<210> SEQ ID NO 537
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 537
gaaattgctc tggattaaa                                                19
```

```
<210> SEQ ID NO 538
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 538
atgaaactta tggctacaa                                                   19

<210> SEQ ID NO 539
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 539
tgaaacttat ggctacaaa                                                   19

<210> SEQ ID NO 540
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 540
aaacttatgg ctacaaaga                                                   19

<210> SEQ ID NO 541
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 541
ggcaaaccgt gcattatta                                                   19

<210> SEQ ID NO 542
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 542
gcaaaccgtg cattattat                                                   19

<210> SEQ ID NO 543
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 543
accgagttct aggcttcaa                                                   19

<210> SEQ ID NO 544
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 544
ccgagttcta ggcttcaaa                                            19

<210> SEQ ID NO 545
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 545
ttctaggctt caaacctaa                                            19

<210> SEQ ID NO 546
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 546
atgagtcctt ggagactta                                            19

<210> SEQ ID NO 547
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 547
gcaagcgaga tgaagataa                                            19

<210> SEQ ID NO 548
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 548
agttggaaat gtggagtat                                            19

<210> SEQ ID NO 549
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 549
ctgcagtatt atccgtact                                            19

<210> SEQ ID NO 550
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 550
tgcagtatta tccgtacta                                            19

<210> SEQ ID NO 551
```

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 551
gcagtattat ccgtactat                                            19

<210> SEQ ID NO 552
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 552
ccgtacagtt caccaatct                                            19

<210> SEQ ID NO 553
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 553
tcaccaatct taccatgga                                            19

<210> SEQ ID NO 554
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 554
aaattcgcat agagtgtaa                                            19

<210> SEQ ID NO 555
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 555
tgtaaggcgt acggtgaga                                            19

<210> SEQ ID NO 556
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 556
tgtgttatgc ttgtattga                                            19

<210> SEQ ID NO 557
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 557
```

```
gccttgtcct ccggtatgt                                                    19

<210> SEQ ID NO 558
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 558
tgtcctccgg tatgttcta                                                    19

<210> SEQ ID NO 559
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 559
gtcctccggt atgttctaa                                                    19

<210> SEQ ID NO 560
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 560
tcctccggta tgttctaaa                                                    19

<210> SEQ ID NO 561
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 561
cctccggtat gttctaaag                                                    19

<210> SEQ ID NO 562
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 562
tccggtatgt tctaaagct                                                    19

<210> SEQ ID NO 563
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 563
ccatcacttt ggctagtga                                                    19

<210> SEQ ID NO 564
<211> LENGTH: 19
<212> TYPE: DNA
```

```
<213> ORGANISM: Artificial Sequence
<220> FEATURE:
<223> OTHER INFORMATION: TARGETING SEQUENCE

<400> SEQUENCE: 564
ccgaggacgc accagttta                                              19

<210> SEQ ID NO 565
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 565
cgaggacgca ccagtttat                                              19

<210> SEQ ID NO 566
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 566
tgcagactgt ctccgacca                                              19

<210> SEQ ID NO 567
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 567
cagactgtct ccgaccata                                              19

<210> SEQ ID NO 568
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 568
caagactgag aaccttgat                                              19

<210> SEQ ID NO 569
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 569
agaaccttga tgtcattgt                                              19

<210> SEQ ID NO 570
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 570
ccttgatgtc attgtcaat                                              19
```

-continued

<210> SEQ ID NO 571
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 571
aagttcttgg agccttaca                                                    19

<210> SEQ ID NO 572
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 572
agttcttgga gccttacaa                                                    19

<210> SEQ ID NO 573
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 573
gagccttaca acgactcta                                                    19

<210> SEQ ID NO 574
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 574
agccttacaa cgactctat                                                    19

<210> SEQ ID NO 575
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 575
ttacaacgac tctatccaa                                                    19

<210> SEQ ID NO 576
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 576
gctattacga acagccaga                                                    19

<210> SEQ ID NO 577
<211> LENGTH: 19
<212> TYPE: DNA
<213> ORGANISM: Artificial Sequence
<220> FEATURE:

-continued

<223> OTHER INFORMATION: TARGETING SEQUENCE

<400> SEQUENCE: 577
tattacgaac agccagata                    19

<210> SEQ ID NO 578
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 578
attacgaaca gccagataa                    19

<210> SEQ ID NO 579
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 579
cagataatgg agtcctcaa                    19

<210> SEQ ID NO 580
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 580
gataatggag tcctcaact                    19

<210> SEQ ID NO 581
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 581
aaacgtgcct gccaattca                    19

<210> SEQ ID NO 582
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 582
aacgtgcctg ccaattcaa                    19

<210> SEQ ID NO 583
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 583
aaccagagca tgaatgtta                    19

```
<210> SEQ ID NO 584
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 584
ctcggcaact tcgtcatgt                                                19

<210> SEQ ID NO 585
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 585
aatgtagaat gtcgcatca                                                19

<210> SEQ ID NO 586
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 586
atgtagaatg tcgcatcaa                                                19

<210> SEQ ID NO 587
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 587
caacatcgcc acagacgat                                                19

<210> SEQ ID NO 588
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 588
gacgatgagc gagacaagt                                                19

<210> SEQ ID NO 589
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 589
tggccttcaa actccgcat                                                19

<210> SEQ ID NO 590
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 590
ccatctctct cctgtggat                                                  19

<210> SEQ ID NO 591
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 591
tttgataaca gagctatga                                                  19

<210> SEQ ID NO 592
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 592
ccattgcggt tccgtcact                                                  19

<210> SEQ ID NO 593
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 593
aggagttagg agcctttct                                                  19

<210> SEQ ID NO 594
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 594
tgtgagagct atccactct                                                  19

<210> SEQ ID NO 595
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 595
cactctcctg cctgcatat                                                  19

<210> SEQ ID NO 596
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 596
cgccacacac acacacaaa                                                  19

<210> SEQ ID NO 597
<211> LENGTH: 19
```

```
<212> TYPE: DNA
<213> ORGANISM: Artificial Sequence
<220> FEATURE:
<223> OTHER INFORMATION: TARGETING SEQUENCE

<400> SEQUENCE: 597
tctacacagt cgccatctt                                                        19

<210> SEQ ID NO 598
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 598
tcgccatctt ggtgactttt                                                       19

<210> SEQ ID NO 599
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 599
ggttgaccta ggctgaata                                                        19

<210> SEQ ID NO 600
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 600
gttgacctag gctgaatat                                                        19

<210> SEQ ID NO 601
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 601
ggctgaatat ccactttgt                                                        19

<210> SEQ ID NO 602
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 602
agcaagttat caactaatc                                                        19

<210> SEQ ID NO 603
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 603
```

-continued

| | |
|---|---|
| gcaagttatc aactaatca | 19 |

<210> SEQ ID NO 604
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 604

| | |
|---|---|
| ccaaatctag cctctgaat | 19 |

<210> SEQ ID NO 605
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 605

| | |
|---|---|
| ctcctgctct gaatattct | 19 |

<210> SEQ ID NO 606
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 606

| | |
|---|---|
| tgtgtcagat ctactgtaa | 19 |

<210> SEQ ID NO 607
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 607

| | |
|---|---|
| ttgctcttct acctagttt | 19 |

<210> SEQ ID NO 608
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 608

| | |
|---|---|
| cagtgaccgc attggaata | 19 |

<210> SEQ ID NO 609
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 609

| | |
|---|---|
| gaccgcattg gaatataca | 19 |

<210> SEQ ID NO 610
<211> LENGTH: 19
<212> TYPE: DNA
<213> ORGANISM: Artificial Sequence

```
<220> FEATURE:
<223> OTHER INFORMATION: TARGETING SEQUENCE

<400> SEQUENCE: 610
ttcagtaggt ctgatccaa                                                      19

<210> SEQ ID NO 611
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 611
cagtaggtct gatccaact                                                      19

<210> SEQ ID NO 612
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 612
ggtacattga agaccttaa                                                      19

<210> SEQ ID NO 613
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 613
tacattgaag accttaaga                                                      19

<210> SEQ ID NO 614
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 614
agaccttaag aagtttcta                                                      19

<210> SEQ ID NO 615
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 615
gaccttaaga agtttctaa                                                      19

<210> SEQ ID NO 616
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 616
gtttatgttg catgtcagt                                                      19
```

```
<210> SEQ ID NO 617
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 617
tggtatgaat gatcctgat                                               19

<210> SEQ ID NO 618
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 618
tgaaggagtg ccaaggata                                               19

<210> SEQ ID NO 619
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 619
tgtagcagtt tatcctcat                                               19

<210> SEQ ID NO 620
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 620
gtagcagttt atcctcata                                               19

<210> SEQ ID NO 621
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 621
ctcataatgg aatgataga                                               19

<210> SEQ ID NO 622
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 622
agccattggt tgctgttca                                               19

<210> SEQ ID NO 623
<211> LENGTH: 19
<212> TYPE: DNA
<213> ORGANISM: Artificial Sequence
<220> FEATURE:
<223> OTHER INFORMATION: TARGETING SEQUENCE
```

<400> SEQUENCE: 623
gccattggtt gctgttcag                                           19

<210> SEQ ID NO 624
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 624
gtaacagttg agtgcaaga                                           19

<210> SEQ ID NO 625
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 625
taacagttga gtgcaagat                                           19

<210> SEQ ID NO 626
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 626
tgatggatca gccaaccta                                           19

<210> SEQ ID NO 627
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 627
gatggatcag ccaacctaa                                           19

<210> SEQ ID NO 628
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 628
atggatcagc caacctaaa                                           19

<210> SEQ ID NO 629
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 629
gcatagtatg agtaggata                                           19

<210> SEQ ID NO 630

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 630
catagtatga gtaggatat                                                19

<210> SEQ ID NO 631
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 631
ggatatctcc acagagtaa                                                19

<210> SEQ ID NO 632
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 632
gatatctcca cagagtaaa                                                19

<210> SEQ ID NO 633
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 633
agaaaggtgt gtggtacat                                                19

<210> SEQ ID NO 634
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 634
ataacgtgct tccagatca                                                19

<210> SEQ ID NO 635
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 635
taacgtgctt ccagatcat                                                19

<210> SEQ ID NO 636
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 636
```
agtgtacagt cgccagata                                              19

<210> SEQ ID NO 637
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 637
gtgaacacct gattccaaa                                              19

<210> SEQ ID NO 638
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 638
agcttaatat gccgtgcta                                              19

<210> SEQ ID NO 639
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 639
taatatgccg tgctatgta                                              19

<210> SEQ ID NO 640
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 640
aatatgccgt gctatgtaa                                              19

<210> SEQ ID NO 641
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 641
atatgccgtg ctatgtaaa                                              19

<210> SEQ ID NO 642
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 642
gccgtgctat gtaaatatt                                              19

<210> SEQ ID NO 643
<211> LENGTH: 19
<212> TYPE: DNA

```
<213> ORGANISM: Artificial Sequence
<220> FEATURE:
<223> OTHER INFORMATION: TARGETING SEQUENCE

<400> SEQUENCE: 643
tgcaagaaat gtggtatgt                                                    19

<210> SEQ ID NO 644
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 644
atgctgaatt agcctcgat                                                    19

<210> SEQ ID NO 645
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 645
ttgattaaga gcacaaact                                                    19

<210> SEQ ID NO 646
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 646
agcagactgt ggactgtaa                                                    19

<210> SEQ ID NO 647
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 647
gcagactgtg gactgtaat                                                    19

<210> SEQ ID NO 648
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 648
cagactgtgg actgtaata                                                    19

<210> SEQ ID NO 649
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 649
taataccaat cgctttcaa                                                    19
```

```
<210> SEQ ID NO 650
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 650
accaatcgct ttcaagtta                                                 19

<210> SEQ ID NO 651
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 651
caatcgcttt caagttagt                                                 19

<210> SEQ ID NO 652
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 652
atagagtact atcgtaaca                                                 19

<210> SEQ ID NO 653
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 653
ccagcctgct tgagattca                                                 19

<210> SEQ ID NO 654
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 654
ctgtagtaga tctacttaa                                                 19

<210> SEQ ID NO 655
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 655
accaatgaca tccggatta                                                 19

<210> SEQ ID NO 656
<211> LENGTH: 19
<212> TYPE: DNA
<213> ORGANISM: Artificial Sequence
<220> FEATURE:
```

<223> OTHER INFORMATION: TARGETING SEQUENCE

<400> SEQUENCE: 656
ccaatgacat ccggattat                                                19

<210> SEQ ID NO 657
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 657
caatgacatc cggattata                                                19

<210> SEQ ID NO 658
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 658
ggctatgact tctcaagat                                                19

<210> SEQ ID NO 659
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 659
gcctcatatg cacttatta                                                19

<210> SEQ ID NO 660
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 660
agacctgcgt atggaattt                                                19

<210> SEQ ID NO 661
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 661
acgtctatgt gacttgtaa                                                19

<210> SEQ ID NO 662
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 662
gtctatgtga cttgtaaga                                                19

```
<210> SEQ ID NO 663
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 663
ttcctacgtg agtgcttta                                                19

<210> SEQ ID NO 664
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 664
gacaatgctc tggaattaa                                                19

<210> SEQ ID NO 665
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 665
ctctggtgat tggatataa                                                19

<210> SEQ ID NO 666
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 666
tgacagagat tgagaacta                                                19

<210> SEQ ID NO 667
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 667
tgagattggc gtggttata                                                19

<210> SEQ ID NO 668
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 668
gcatccgagg cttgtttaa                                                19

<210> SEQ ID NO 669
<211> LENGTH: 19
<212> TYPE: DNA
<213> ORGANISM: Artificial Sequence
<220> FEATURE:
<223> OTHER INFORMATION: TARGETING SEQUENCE
```

```
<400> SEQUENCE: 669
accatatcgt ctccatgaa                                              19

<210> SEQ ID NO 670
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 670
ccatatcgtc tccatgaaa                                              19

<210> SEQ ID NO 671
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 671
tgaaagctgc aaagattta                                              19

<210> SEQ ID NO 672
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 672
tcgactgaat gaactctta                                              19

<210> SEQ ID NO 673
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 673
ccatatcgga tttgttgta                                              19

<210> SEQ ID NO 674
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 674
ggttggaaat cctcacaaa                                              19

<210> SEQ ID NO 675
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 675
cttactagtt agaggaaat                                              19

<210> SEQ ID NO 676
<211> LENGTH: 19
```

```
<212> TYPE: DNA
<213> ORGANISM: Artificial Sequence
<220> FEATURE:
<223> OTHER INFORMATION: TARGETING SEQUENCE

<400> SEQUENCE: 676
accaccagca ctactatta                                                19

<210> SEQ ID NO 677
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 677
ccaccagcac tactattat                                                19

<210> SEQ ID NO 678
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 678
cagcactact attatgata                                                19

<210> SEQ ID NO 679
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 679
ctatcagtcc ttgtaataa                                                19

<210> SEQ ID NO 680
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 680
attgtctact tcagcaata                                                19

<210> SEQ ID NO 681
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 681
tattggtgat ttcgtcata                                                19

<210> SEQ ID NO 682
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 682
```
ttcgtcatag gaacattta 19

<210> SEQ ID NO 683
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 683
taatgacact atcgtaaca 19

<210> SEQ ID NO 684
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 684
gatgtttgct aaaggttat 19

<210> SEQ ID NO 685
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 685
cttcgtggct acatcttaa 19

<210> SEQ ID NO 686
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 686
tgcacttgga ttcatctta 19

<210> SEQ ID NO 687
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 687
gatgatctgt ggccatgta 19

<210> SEQ ID NO 688
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 688
ctcgaagaca agccatgaa 19

<210> SEQ ID NO 689
<211> LENGTH: 19
<212> TYPE: DNA
<213> ORGANISM: Artificial Sequence

```
<220> FEATURE:
<223> OTHER INFORMATION: TARGETING SEQUENCE

<400> SEQUENCE: 689
tgaaagagat gtccatcga                                               19

<210> SEQ ID NO 690
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 690
agagatgtcc atcgatcaa                                               19

<210> SEQ ID NO 691
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 691
ccatcgatca agccaaata                                               19

<210> SEQ ID NO 692
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 692
catcgatcaa gccaaatat                                               19

<210> SEQ ID NO 693
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 693
ggtcgtatga agccaaaca                                               19

<210> SEQ ID NO 694
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 694
cacttgtcct tggatttaa                                               19

<210> SEQ ID NO 695
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 695
tagtggttat tcgcctaaa                                               19
```

<210> SEQ ID NO 696
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 696
atctcatctt caaggacaa                                            19

<210> SEQ ID NO 697
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 697
cgatttagat acttccaaa                                            19

<210> SEQ ID NO 698
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 698
tcattggtgg aaagataaa                                            19

<210> SEQ ID NO 699
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 699
ttagcaagtt ccggataga                                            19

<210> SEQ ID NO 700
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 700
gaaatcattg agccataca                                            19

<210> SEQ ID NO 701
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 701
agcaagatat tgcagataa                                            19

<210> SEQ ID NO 702
<211> LENGTH: 19
<212> TYPE: DNA
<213> ORGANISM: Artificial Sequence
<220> FEATURE:
<223> OTHER INFORMATION: TARGETING SEQUENCE

```
<400> SEQUENCE: 702
gatgaaccat ggcgaataa                                              19

<210> SEQ ID NO 703
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 703
cattcaagca cagctaata                                              19

<210> SEQ ID NO 704
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 704
ttcagtgcct agtgtagta                                              19

<210> SEQ ID NO 705
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 705
aggaaagttg ctccattga                                              19

<210> SEQ ID NO 706
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 706
aaagttgctc cattgataa                                              19

<210> SEQ ID NO 707
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 707
caatcttaat ggtgattct                                              19

<210> SEQ ID NO 708
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 708
ttgacatcat agtctagta                                              19

<210> SEQ ID NO 709
```

```
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 709
gacatcatag tctagtaaa                                               19

<210> SEQ ID NO 710
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 710
gtgtgtgtgt gtgtatata                                               19

<210> SEQ ID NO 711
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 711
gtgtgtgtgt gtatatata                                               19

<210> SEQ ID NO 712
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 712
taggcaaact ttggtttaa                                               19

<210> SEQ ID NO 713
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 713
ggagaatact tcgcctaaa                                               19

<210> SEQ ID NO 714
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 714
tgagtatgac ctaggtata                                               19

<210> SEQ ID NO 715
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 715
```

```
agagatctga taacttgaa                                              19

<210> SEQ ID NO 716
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 716
ggtaaagaca gtagaaata                                              19

<210> SEQ ID NO 717
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 717
tttaagctct ggtggatga                                              19

<210> SEQ ID NO 718
<211> LENGTH: 25
<212> TYPE: RNA
<213> ORGANISM: Artificial Sequence
<220> FEATURE:
<223> OTHER INFORMATION: SENSE STRAND

<400> SEQUENCE: 718
cccugaggau ccucaacaau gguca                                       25

<210> SEQ ID NO 719
<211> LENGTH: 27
<212> TYPE: RNA
<213> ORGANISM: Artificial Sequence
<220> FEATURE:
<223> OTHER INFORMATION: ANTISENSE STRAND

<400> SEQUENCE: 719
ugaccauugu ugaggauccu caggguu                                     27

<210> SEQ ID NO 720
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 720
ggatggcact tacagattg                                              19

<210> SEQ ID NO 721
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 721
gaaatatgct gcagaactt                                              19

<210> SEQ ID NO 722
<211> LENGTH: 19
<212> TYPE: RNA
```

-continued

```
<213> ORGANISM: Artificial Sequence
<220> FEATURE:
<223> OTHER INFORMATION: SENSE STRAND

<400> SEQUENCE: 722
cccugaggau ccucaacaa                                            19

<210> SEQ ID NO 723
<211> LENGTH: 19
<212> TYPE: RNA
<213> ORGANISM: Artificial Sequence
<220> FEATURE:
<223> OTHER INFORMATION: ANTISENSE STRAND

<400> SEQUENCE: 723
uuguugagga uccucaggg                                            19

<210> SEQ ID NO 724
<211> LENGTH: 25
<212> TYPE: DNA
<213> ORGANISM: Artificial Sequence
<220> FEATURE:
<223> OTHER INFORMATION: TARGETING SEQUENCE

<400> SEQUENCE: 724
ccctgaggat cctcaacaat ggtca                                     25
```

RNAI-MEDIATED INHIBITION OF OCULAR TARGETS

The present application claims the benefit of co-pending U.S. Provisional Patent Applications having Ser. Nos. 60/648,926 filed Feb. 1, 2005, and 60/753,364 filed Dec. 22, 2005, the texts of which are specifically incorporated by reference herein.

FIELD OF THE INVENTION

The present invention relates to the field of interfering RNA compositions for inhibition of expression of ocular hypertension targets in glaucoma, particularly for primary open angle glaucoma.

BACKGROUND OF THE INVENTION

Glaucoma is a heterogeneous group of optic neuropathies that share certain clinical features. The loss of vision in glaucoma is due to the selective death of retinal ganglion cells in the neural retina that is clinically diagnosed by characteristic changes in the visual field, nerve fiber layer defects, and a progressive cupping of the optic nerve head (ONH). One of the main risk factors for the development of glaucoma is the presence of ocular hypertension (elevated intraocular pressure, IOP). An adequate intraocular pressure is needed to maintain the shape of the eye and to provide a pressure gradient to allow for the flow of aqueous humor to the avascular cornea and lens. IOP levels may also be involved in the pathogenesis of normal tension glaucoma (NTG), as evidenced by patients benefiting from IOP lowering medications. Once adjustments for central corneal thickness are made to IOP readings in NTG patients, many of these patients may be found to be ocular hypertensive.

The elevated IOP associated with glaucoma is due to elevated aqueous humor outflow resistance in the trabecular meshwork (TM), a small specialized tissue located in the iris-corneal angle of the ocular anterior chamber. Glaucomatous changes to the TM include a loss in TM cells and the deposition and accumulation of extracellular debris including proteinaceous plaque-like material. In addition, there are also changes that occur in the glaucomatous ONH. In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

Primary glaucomas result from disturbances in the flow of intraocular fluid that has an anatomical or physiological basis. Secondary glaucomas occur as a result of injury or trauma to the eye or a preexisting disease. Primary open angle glaucoma (POAG), also known as chronic or simple glaucoma, represents ninety percent of all primary glaucomas. POAG is characterized by the degeneration of the trabecular meshwork, resulting in abnormally high resistance to fluid drainage from the eye. A consequence of such resistance is an increase in the IOP that is required to drive the fluid normally produced by the eye across the increased resistance.

Current anti-glaucoma therapies include lowering IOP by the use of suppressants of aqueous humor formation or agents that enhance uveoscleral outflow, laser trabeculoplasty, or trabeculectomy, which is a filtration surgery to improve drainage. Pharmaceutical anti-glaucoma approaches have exhibited various undesirable side effects. For example, miotics such as pilocarpine can cause blurring of vision and other negative visual side effects. Systemically administered carbonic anhydrase inhibitors (CAIs) can also cause nausea, dyspepsia, fatigue, and metabolic acidosis. Further, certain beta-blockers have increasingly become associated with serious pulmonary side effects attributable to their effects on beta-2 receptors in pulmonary tissue. Sympathomimetics cause tachycardia, arrhythmia and hypertension. Such negative side effects may lead to decreased patient compliance or to termination of therapy. In addition, the efficacy of current IOP lowering therapies is relatively short-lived requiring repeated dosing during each day and, in some cases, the efficacy decreases with time.

In view of the importance of ocular hypertension in glaucoma, and the inadequacies of prior methods of treatment, it would be desirable to have an improved method of treating ocular hypertension that would address the underlying causes of its progression.

SUMMARY OF THE INVENTION

The present invention is directed to interfering RNAs that silence ocular hypertension target mRNA expression, thus lowering intraocular pressure in patients with open-angle glaucoma or ocular hypertension. Ocular hypertension targets include carbonic anhydrase II, IV, and XII; $\beta1$- and $\beta2$ adrenergic receptors; acetylcholinesterase; $Na^+/K^+$-ATPase; and Na—K-2Cl cotransporter. The interfering RNAs of the invention are useful for treating patients with open-angle glaucoma or ocular hypertension.

An embodiment of the present invention provides a method of attenuating expression of an ocular hypertension target mRNA such as carbonic anhydrase II, IV, or XII; $\beta1$- or $\beta2$ adrenergic receptors; acetylcholinesterase; $Na^+/K^+$-ATPase; or Na—K-2Cl cotransporter mRNA in a subject. The method comprises administering to the subject a composition comprising an effective amount of interfering RNA having a length of 19 to 49 nucleotides and a pharmaceutically acceptable carrier. Administration is to the eye of the subject for attenuating expression of an ocular hypertension target in a human.

In one embodiment of the invention, the interfering RNA comprises a sense nucleotide strand, an antisense nucleotide strand and a region of at least near-perfect contiguous complementarity of at least 19 nucleotides. Further, the antisense strand hybridizes under physiological conditions to a portion of an mRNA corresponding to SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134 which are sense cDNA sequences encoding carbonic anhydrase II and IV; $\beta1$- and $\beta2$ adrenergic receptors; acetylcholinesterase (ACHE) variant E4-E5; $Na^+/K^+$-ATPase $\alpha2$ polypeptide; Na—K-2Cl cotransporter NKCC2 (SLC12A1), carbonic anhydrase XII variant 1, acetylcholinesterase variant E4-E6, $Na^+/K^+$-ATPase $\alpha1$ polypeptide variant 1 and variant 2, $Na^+/K^+$-ATPase $\alpha3$ polypeptide, $Na^+/K^+$-ATPase $\alpha4$ polypeptide variant 1 and variant 2, $Na^+/K^+$-ATPase $\beta1$ polypeptide variant 1 and 2, $Na^+/K^+$-ATPase $\beta2$ polypeptide, $Na^+/K^+$-ATPase $\beta3$ polypeptide, Na—K-2Cl cotransporter NKCC1 (SLC12A2), and carbonic anhydrase XII variant 2, respectively. The antisense strand has a region of at least near-perfect contiguous complementarity of at least 19 nucleotides with the hybridizing portion of mRNA corresponding to SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, respectively. The administration of such a composition attenuates the expression of an ocular hypertension target mRNA of the subject.

In one embodiment, the ocular hypertension target mRNA encodes carbonic anhydrase II, IV or XII, and the antisense strand hybridizes under physiological conditions to a portion of mRNA corresponding to SEQ ID NO:1, SEQ ID NO:2, SEQ ID NO:101, or SEQ ID NO:134 and has a region of at least near-perfect contiguous complementarity of at least 19 nucleotides with the hybridizing portion of mRNA corresponding to SEQ ID NO:1, SEQ ID NO:2, SEQ ID NO:101, or SEQ ID NO:134, respectively.

In another embodiment, the ocular hypertension target mRNA encodes a β1- or β2-adrenergic receptor, and the antisense strand hybridizes under physiological conditions to a portion of mRNA corresponding to SEQ ID NO:3 or SEQ ID NO:4 and has a region of at least near-perfect contiguous complementarity of at least 19 nucleotides with the hybridizing portion of mRNA corresponding to SEQ ID NO:3 or SEQ ID NO:4, respectively.

In a further embodiment, the ocular hypertension target mRNA encodes an acetylcholinesterase, and the antisense strand hybridizes under physiological conditions to a portion of mRNA corresponding to SEQ ID NO:5 or SEQ ID NO:123 and has a region of at least near-perfect contiguous complementarity of at least 19 nucleotides with the hybridizing portion of mRNA corresponding to SEQ ID NO:5 or SEQ ID NO:123, respectively.

In yet another embodiment, the ocular hypertension target mRNA encodes a subunit of Na$^+$/K$^+$-ATPase, and the antisense strand hybridizes under physiological conditions to a portion of mRNA corresponding to SEQ ID NO:6, SEQ ID NO:124, SEQ ID NO:125, SEQ ID NO:126, SEQ ID NO:127, SEQ ID NO:128, SEQ ID NO:129, SEQ ID NO:130, SEQ ID NO:131, or SEQ ID NO:132 and has a region of at least near-perfect contiguous complementarity of at least 19 nucleotides with the hybridizing portion of mRNA corresponding to SEQ ID NO:6, SEQ ID NO:124, SEQ ID NO:125, SEQ ID NO:126, SEQ ID NO:127, SEQ ID NO:128, SEQ ID NO:129, SEQ ID NO:130, SEQ ID NO:131, or SEQ ID NO:132, respectively.

In a further embodiment, the ocular hypertension target mRNA encodes a Na—K-2Cl cotransporter, and the antisense strand hybridizes under physiological conditions to a portion of mRNA corresponding to SEQ ID NO:7 or SEQ ID NO:133 and has a region of at least near-perfect contiguous complementarity of at least 19 nucleotides with the hybridizing portion of mRNA corresponding to SEQ ID NO:7 or SEQ ID NO:133, respectively.

In one embodiment of the invention, an interfering RNA is designed to target an mRNA corresponding to SEQ ID NO:1 comprising nucleotide 232, 527, 721, 728, 809, 810, 855, 856, 921, 1139, 506, 547, 548, 740, 911, 1009, 1140, 1149, 1150, 1151, 1188, 1194, 1195, 1223, 1239, 1456, 1457, 1458, 100, 158, 166, 247, 286, 318, 322, 328, 371, 412, 482, 504, 505, 541, 734, 772, 777, 814, 972, 998, 1232, 317, or 401.

In another embodiment of the invention, an interfering RNA is designed to target an mRNA corresponding to SEQ ID NO:2 comprising nucleotide 213, 252, 258, 266, 399, 457, 463, 490, 595, 1064, 109, 112, 125, 126, 150, 261, 265, 280, 398, 453, 459, 462, 467, 492, 534, 785, 801, 825, 827, 876, 1003, or 1012.

In a further embodiment of the invention, an interfering RNA is designed to target an mRNA corresponding to SEQ ID NO:101 comprising nucleotide 191, 239, 274, 275, 341, 389, 412, 413, 423, 687, 689, 695, 710, 791, 792, 794, 983, 993, 994, 995, 691, 1039, 1568, 2326, 2332, 2425, 2433, 2844, 2845, 2880, 2884, 2891, 2954, 2955, 2956, 2957, 2964, 2965, 3006, 3007, 3012, or 3026.

In another embodiment, an interfering RNA is designed to target an mRNA corresponding to SEQ ID NO:134 comprising nucleotide 687, 1535, 2293, 2299, 2392, 2400, 2811, 2812, 2847, 2851, 2858, 2921, 2922, 2923, 2924, 2931, 2932, 2973, 2974, 2979, or 2993.

Another embodiment of the invention provides an interfering RNA designed to target an mRNA corresponding to SEQ ID NO:3 comprising nucleotide 468, 523, 799, 1563, 1565, 1569, 1593, 1613, 1614, 1626, 310, 322, 726, 769, 772, 801, 802, 1501, 1576, 1577, 1579, 1580, 1581, 1586, 1590, 1592, 1594, 1615, 1616, 1632, 1633, or 1654.

A further embodiment of the invention provides an interfering RNA designed to target an mRNA corresponding to SEQ ID NO:4 comprising nucleotide 329, 375, 1031, 1046, 1149, 1163, 1371, 1401, 1426, 1880, 283, 607, 608, 609, 619, 623, 722, 857, 1037, 1091, 1115, 1124, 1136, 1137, 1151, 1164, 1393, 1394, 1395, 1406, 1407, 1427, 1428, 1429, 1442, 1725, 1726, 1756, 1757, 1758, 1767, 1790, 1791, 1792, 1793, 1803, 1861, 1869, 1971, 1972, or 1979.

In another method of the invention, an interfering RNA is designed to target an mRNA corresponding to SEQ ID NO:123 comprising nucleotide 1875, 1890, 1891, 2011, 2012, 2133, or 2134.

Another embodiment of the invention provides an interfering RNA designed to target an mRNA corresponding to SEQ ID NO:5 comprising nucleotide 366, 370, 384, 385, 525, 588, 768, 1045, 1046, 1061, 1090, 1232, 1314, 1316, 1460, 1461, 1462, 1528, 1607, 1705, 1713, 382, 393, 397, 622, 1131, 1459, 1530, 2251, 2885, 2886, 386, 1231, 1315, 2047, 2049, 2053, 2055, 2057, 2125, 2126, 2127, 2250, 2253, 2258, 2260, 2318, 2395, 2397, 2404, 2405, 2643, 2645, or 2887.

In a further embodiment, an interfering RNA is designed to target an mRNA corresponding to SEQ ID NO:124 comprising nucleotide 2208, 2275, 2307, 2526, 2538, 2592, 2628, 2979, 2985, 3093, 3474, 3504, 3505, 3506, 3518, 343, 442, 700, 707, 811, 907, 1059, 1363, 1594, 1662, 1758, 1760, 1896, 2037, or 2147.

In yet another embodiment, an interfering RNA is designed to target an mRNA corresponding to SEQ ID NO:125 comprising nucleotide 436, 441, 443, 552, 617, 701, 702, 832, 2204, 2291, or 2495.

A further embodiment of the present invention provides an interfering RNA designed to target an mRNA corresponding to SEQ ID NO:6 comprising nucleotide 471, 1990, 3080, 3797, 4037, 4093, 4225, 4323, 5213, 5285, 214, 467, 470, 472, 473, 632, 825, 946, 1693, 1767, 1768, 2157, 2263, 2589, 2590, 2765, 2988, 3094, 3144, 3145, 3344, 3345, 3418, 3666, 3828, 3850, 4040, 4041, 4061, 4882, 4894, 4900, 5040, 5114, 5115, 5128, 5129, 5253, 5296, 5375, 5384, or 5385.

In another embodiment of the invention, an interfering RNA is designed to target an mRNA corresponding to SEQ ID NO:126 comprising nucleotide 240, 272, 362, 1836, 1851, 2103, 2137, 2138, 2139, 2157, 2158, 2160, 2425, 2580, 2601, 2646, 2650, 2794, 2803, 3116, 3124, 3126, 3129, or 3377.

In yet another embodiment of the invention, an interfering RNA is designed to target an mRNA corresponding to SEQ ID NO:127 comprising nucleotide 113, 612, 702, 833, 1101, 1732, 1733, 1836, 2070, 2071, 2143, 2328, 2475, 2861, 2862, 2952, 3203, 3281, 3377, 3379, 3470, 3471, 3554, 3614, 3615, 3616, 3617, 3625, 3626, 3642, 3646, 3647, 3653, 3655, 3797, 3801, 3803, 3809 or 3810.

In another embodiment, an interfering RNA is designed to target an mRNA corresponding to SEQ ID NO:128 comprising nucleotide 126, 251, 252, 253, 331, 427, 429, 520, 521, 530, 601, 602, 603, 604, 664, 665, 666, 667, 675, 676, 692, 696, 697, 702, 703, 705, 707, 847, 851, 853, 859, or 860.

In yet another embodiment, an interfering RNA is designed to target an mRNA corresponding to SEQ ID NO:129 comprising nucleotide 1096, 1099, 1130, 1131, 1167, 1299, 1441, 1450, 1451, 1452, 1564, 1746, 1750, 1751, 1752, 1795, 203, 204, 214, 222, 224, 225, 226, 380, 525, 591, 612, 613, 615, 635, 636, 663, 664, 669, 699, 765, 790, 839, 840, 841, 900, 909, 933, or 947.

In another embodiment, an interfering RNA is designed to target an mRNA corresponding to SEQ ID NO:130 comprising nucleotide 1063, 1102, 1106, 1107, 1108, 1109, 1111, or 1151.

In another embodiment, an interfering RNA is designed to target an mRNA corresponding to SEQ ID NO:131 comprising nucleotide 653, 654, 771, 773, 841, 849, 853, 917, 918, 926, 927, 931, 981, 983, 984, 996, 998, 1022, 1023, 1160, 1214, 1355, 1356, 1381, 1394, 1425, 1474, 1550, 1620, 1707, 1740, 1753, 1825, 1956, 1965, 2598, 2599, 2608, 2828, 2829, 2888, 3012, or 3251.

In another embodiment of the invention, an interfering RNA is designed to target an mRNA corresponding to SEQ ID NO:132 comprising nucleotide 292, 434, 438, 457, 459, 488, 490, 498, 499, 592, 639, 723, 774, 775, 788, 857, 858, 910, 911, 930, 931, 932, 1009, 1010, 1023, 1024, 1111, 1146, 1147, 1220, 1246, 1321, 1325, 1326, 1327, 1331, 1437, 1548, 1571, 1785, 1786, or 1787.

Another embodiment of the present invention provides an interfering RNA designed to target an mRNA corresponding to SEQ ID NO:7 comprising nucleotide 675, 974, 1373, 1780, 2102, 2151, 2315, 2542, 2609, 3197, 67, 71, 73, 353, 405, 864, 911, 912, 913, 1409, 1748, 1811, 1935, 1937, 1993, 2012, 2346, 2388, 2437, 2586, 3007, 3008, 3022, 3130, 3210, 3237, or 3271.

Another embodiment of the present invention provides an interfering RNA designed to target an mRNA corresponding to SEQ ID NO:133 comprising nucleotide 748, 749, 753, 1119, 1169, 1499, 1509, 1820, 2081, 2118, 2147, 2615, 2644, 2659, 2663, 2671, 2672, 2793, 2812, 2914, 2948, 3044, 3334, 3391, 3480, 3520, 3549, 3639, 3840, 3941, 3944, 4001, 4995, 4997, 5141, 5143, 5249, 5375, 5834, 5852, 5981, or 6678.

The present invention further provides for administering a second interfering RNA to a subject in addition to a first interfering RNA. The method comprises administering to the subject a second interfering RNA having a length of 19 to 49 nucleotides and comprising a sense nucleotide strand, an antisense nucleotide strand, and a region of at least near-perfect complementarity of at least 19 nucleotides; wherein the antisense strand of the second interfering RNA hybridizes under physiological conditions to a second portion of mRNA corresponding to SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, and the antisense strand has a region of at least near-perfect contiguous complementarity of at least 19 nucleotides with the second hybridizing portion of mRNA corresponding to SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, respectively. The second interfering RNA may target the same mRNA as the first interfering RNA or may target a different mRNA. Further, a third, fourth, or fifth, etc. interfering RNA may be administered in a similar manner.

A further embodiment of the invention is a method of treating ocular hypertension in a subject in need thereof. The method comprises administering to the eye of the subject a composition comprising an effective amount of interfering RNA having a length of 19 to 49 nucleotides and a pharmaceutically acceptable carrier, the interfering RNA comprising a sense nucleotide strand, an antisense nucleotide strand, and a region of at least near-perfect contiguous complementarity of at least 19 nucleotides. The antisense strand hybridizes under physiological conditions to a portion of mRNA corresponding to SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134 and has a region of at least near-perfect contiguous complementarity of at least 19 nucleotides with the hybridizing portion of mRNA corresponding to SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, respectively. The ocular hypertension is treated thereby.

Another embodiment of the invention is a method of attenuating expression of an ocular hypertension target mRNA in a subject comprising administering to the subject a composition comprising an effective amount of single-stranded interfering RNA having a length of 19 to 49 nucleotides and a pharmaceutically acceptable carrier. For attenuating expression of an ocular hypertension target, the single-stranded interfering RNA hybridizes under physiological conditions to a portion of mRNA corresponding to the sequence identifiers and nucleotide positions cited supra for antisense strands.

Another embodiment of the invention is a method of attenuating expression of an ocular hypertension target mRNA in a subject, comprising administering to the subject a composition comprising an effective amount of interfering RNA having a length of 19 to 49 nucleotides and a pharmaceutically acceptable carrier, where the interfering RNA comprises a region of at least 13 contiguous nucleotides having at least 90% sequence complementarity to, or at least 90% sequence identity with, the penultimate 13 nucleotides of the 3' end of any one of SEQ ID NO:8, SEQ ID NO:14-SEQ ID NO:100, SEQ ID NO:102-SEQ ID NO:122, SEQ ID NO:135-SEQ ID NO:717, SEQ ID NO:720, and SEQ ID NO:721, as follows.

When the ocular hypertension target mRNA encodes carbonic anhydrase mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:8, SEQ ID NO:14-SEQ ID NO:32, SEQ ID NO:83-SEQ ID NO:100, SEQ ID NO:102-SEQ ID NO:122, SEQ ID NO:135-SEQ ID NO:219, SEQ ID NO:720, and SEQ ID NO:721.

When the ocular hypertension target mRNA encodes a β-adrenergic receptor mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:33-SEQ ID NO:52, and SEQ ID NO:220-SEQ ID NO:282.

When the ocular hypertension target mRNA encodes ACHE mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:53-SEQ ID NO:62 and SEQ ID NO:283-333.

When the ocular hypertension target mRNA encodes ATP1A1 mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:334-SEQ ID NO:374.

When the ocular hypertension target mRNA encodes ATP1A2 mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:63-SEQ ID NO:72 and SEQ ID NO:375-SEQ ID NO:416.

When the ocular hypertension target mRNA encodes ATP1A3 mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:417-SEQ ID NO:440.

When the ocular hypertension target mRNA encodes ATP1A4 mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:441-SEQ ID NO:511.

When the ocular hypertension target mRNA encodes ATP1B1 mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:512-SEQ ID NO:563.

When the ocular hypertension target mRNA encodes ATP1B2 mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:564-SEQ ID NO:606.

When the ocular hypertension target mRNA encodes ATP1B3 mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:607-SEQ ID NO:648.

When the ocular hypertension target mRNA encodes SLC12A1 mRNA, the interfering RNA comprises a region of at least 13 contiguous nucleotides having at least 90% sequence complementarity to, or at least 90% sequence identity with, the penultimate 13 nucleotides of the 3' end of any one of SEQ ID NO:73-SEQ ID NO:82 and SEQ ID NO:649-SEQ ID NO:675.

When the ocular hypertension target mRNA encodes SLC12A2 mRNA, the interfering RNA comprises a region of at least 13 contiguous nucleotides having at least 90% sequence complementarity to, or at least 90% sequence iden-tity with, the penultimate 13 nucleotides of the 3' end of any one of SEQ ID NO:676-SEQ ID NO:717.

In a further embodiment of the present invention, the region of contiguous nucleotides is a region of at least 14 contiguous nucleotides having at least 85% sequence complementarity to, or at least 85% sequence identity with, the penultimate 14 nucleotides of the 3' end of the sequence of the sequence identifier. In yet another embodiment of the invention, the region of contiguous nucleotides is a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of the sequence of the sequence identifier.

A composition comprising interfering RNA having a length of 19 to 49 nucleotides and having a nucleotide sequence of any one of SEQ ID NO's: 8, SEQ ID NO:14-SEQ ID NO:100, SEQ ID NO:102-SEQ ID NO:122, SEQ ID NO:135-SEQ ID NO:717, SEQ ID NO:720, and SEQ ID NO:721, or a complement thereof, and a pharmaceutically acceptable carrier is an embodiment of the present invention. In one embodiment, the interfering RNA is isolated. The term "isolated" means that the interfering RNA is free of its total natural mileau.

Another embodiment of the invention is a method of treating ocular hypertension in a subject in need thereof, the method comprising administering to an eye of the subject a composition comprising an effective amount of interfering RNA having a length of 19 to 49 nucleotides and a pharmaceutically acceptable carrier, the interfering RNA comprising a region of at least 13 contiguous nucleotides having at least 90% sequence complementarity to, or at least 90% sequence identity with, the penultimate 13 nucleotides of the 3' end of any one of SEQ ID NO:8, SEQ ID NO:14-SEQ ID NO:100, SEQ ID NO:102-SEQ ID NO:122, SEQ ID NO:135-SEQ ID NO:717, SEQ ID NO:720, and SEQ ID NO:721, wherein the ocular hypertension is treated thereby.

A method of attenuating expression of an ocular hypertension target mRNA first variant without attenuating expression of an ocular hypertension target mRNA second variant in a subject is a further embodiment of the invention. The method comprises administering to the subject a composition comprising an effective amount of interfering RNA having a length of 19 to 49 nucleotides and a pharmaceutically acceptable carrier, the interfering RNA comprising a region of at least 13 contiguous nucleotides having at least 90% sequence complementarity to, or at least 90% sequence identity with, the penultimate 13 nucleotides of the 3' end of the first variant, wherein the expression of the first variant mRNA is attenuated without attenuating expression of the second variant mRNA, and wherein the first variant target mRNA is SEQ ID NO:101, SEQ ID NO:5, SEQ ID NO:124, SEQ ID NO:127, or SEQ ID NO:129, and the second variant target mRNA is SEQ ID NO:134, SEQ ID NO:123, SEQ ID NO:125, SEQ ID NO:128, or SEQ ID NO:130, respectively.

In a further embodiment of the above-cited method, the first variant target mRNA is SEQ ID NO:134, SEQ ID NO:123, SEQ ID NO:125, SEQ ID NO:128, or SEQ ID NO:130, and the second variant target mRNA is SEQ ID NO:101, SEQ ID NO:5, SEQ ID NO:124, SEQ ID NO:127, or SEQ ID NO:129, respectively.

Use of any of the embodiments as described herein in the preparation of a medicament for attenuating expression of an ocular hypertension mRNA is also an embodiment of the present invention.

DETAILED DESCRIPTION OF THE INVENTION

Figure 1:
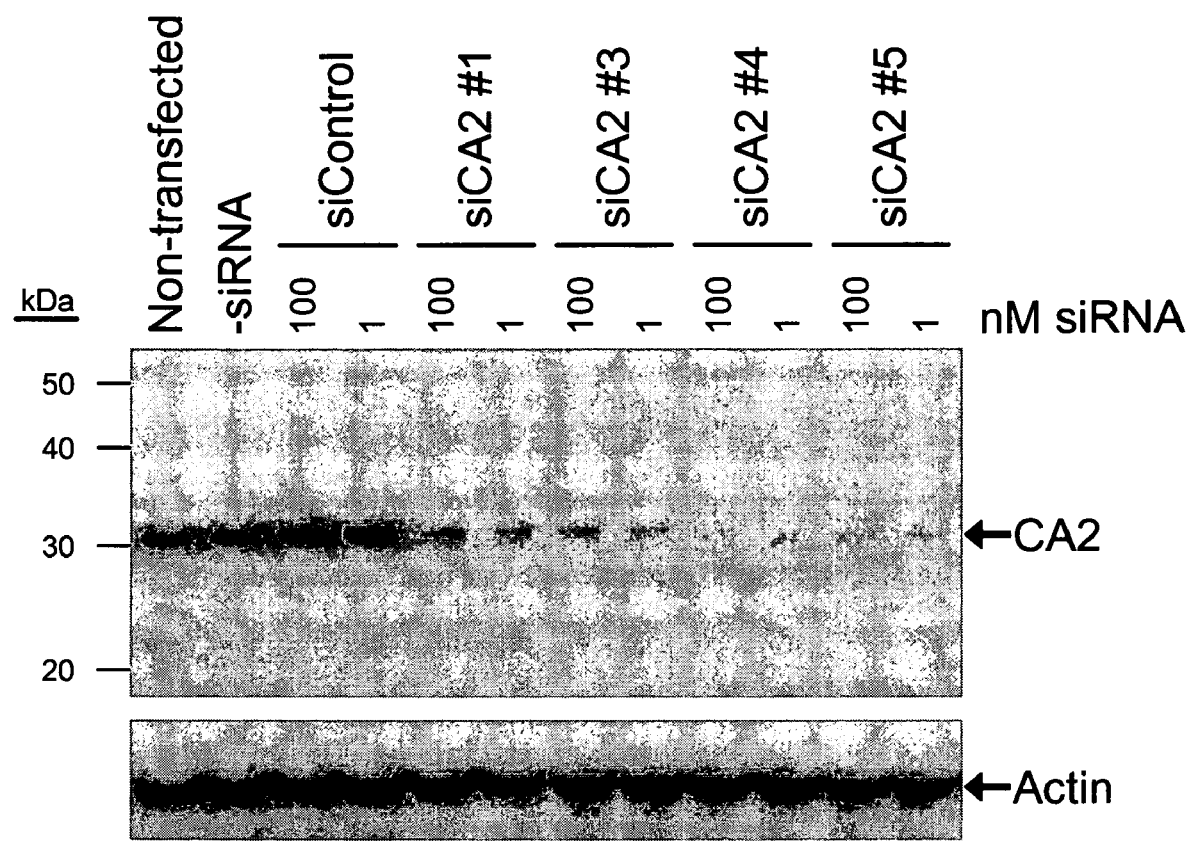
FIG. 1 provides a western blot, probed with antibodies against CA2 and actin, of HeLa cells transfected with CA2 siRNAs #1, #3, #4, and #5; a non-targeting control siRNA; and a buffer control (-siRNA). The siRNAs were at a concentration of 100 nM or 1 nM. The arrows indicate the positions of the ~30-kDa CA2 protein and 42-kDa actin protein bands.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include short hairpin RNAs (shRNAs), single-stranded siRNAs, microRNAs (mRNAs), and dicer-substrate 27-mer duplexes. The term "siRNA" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodiester linkages. For purposes of the present discussion, all RNA or RNA-like molecules that can interact with RISC and participate in RISC-mediated changes in gene expression will be referred to as "interfering RNAs." SiRNAs, shRNAs, mRNAs, and dicer-substrate 27-mer duplexes are, therefore, subsets of "interfering RNAs."

Interfering RNA of embodiments of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

The present invention relates to the use of interfering RNA to inhibit the expression of ocular hypertension target mRNA, thus lowering intraocular pressure in patients with open-angle glaucoma or ocular hypertension. Ocular hypertension targets include carbonic anhydrase II, IV, and XII; β1- and β2 adrenergic receptors; acetylcholinesterase; $Na^+/K^+$-ATPase subunits; and Na—K-2Cl cotransporter. According to the present invention, interfering RNAs provided exogenously or expressed endogenously effect silencing of ocular hypertension target mRNA in ocular tissue(s).

Carbonic anhydrase catalyzes reversible hydration of carbon dioxide and appears to play a role in the regulation of aqueous humor formation. Carbonic anhydrase inhibitors lower pressure in the eye by reducing the amount of fluid produced. Carbonic anhydrase inhibitors are available as eye-drops (dorzolamide, brinzolamide) or tablets/capsules (acetazolamide, methazolamide). The eyedrops are associated with fewer side effects than the tablets or capsules and are better tolerated by many patients. AZOPT® (brinzolamide) ophthalmic suspension 1% is a topical carbonic anhydrase inhibitor (Alcon Laboratories, Inc., Fort Worth, Tex.).

Ophthalmic β-blockers lower pressure in the eye by reducing the amount of fluid produced in the eye. These drugs are divided into two classes: the nonselective beta-blockers (timolol, levobunolol, metipranolol, carteolol) and the β-1 selective blockers (betaxolol). The usual dosage is one drop in each eye once or twice a day, depending on the drug used. An example of this product is BETOPTIC S® (betaxolol HCl) ophthalmic suspension 0.25% (Alcon Laboratories, Inc., Fort Worth, Tex.).

Inhibitors of acetylcholinesterase preserve acetylcholine at the receptor site by blocking the enzyme responsible for its hydrolysis, acetylcholinesterase. Acetylcholine accumulates at the receptor, producing a reduction in intraocular pressure by contraction of the ciliary muscle, similar to the action of direct-acting cholinergic agonists.

$Na^+/K^+$-ATPase inhibitors such as ouabain, nitric oxide donors, and endothelin decrease the activity of $Na^+/K^+$-ATPase, the driving force for aqueous humour formation by the ciliary process.

Chloride transport inhibitors such as ethacrynic acid alter trabecular meshwork cell volume to increase outflow facility.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

An mRNA sequence is readily deduced from the sequence of the corresponding DNA sequence. For example, SEQ ID NO:1 provides the sense strand sequence of DNA corresponding to the mRNA for carbonic anhydrase II. The mRNA sequence is identical to the DNA sense strand sequence with the "T" bases replaced with "U" bases.

Therefore, the mRNA sequence of carbonic anhydrase II is known from SEQ ID NO:1, the mRNA sequence of carbonic anhydrase IV is known from SEQ ID NO:2, the mRNA sequence of β1-adrenergic receptor is known from SEQ ID NO:3, the mRNA sequence of β2-adrenergic receptor is known from SEQ ID NO:4, the mRNA sequence of acetylcholinesterase splice variant E4-E5 is known from SEQ ID NO:5, the mRNA sequence of Na$^+$/K$^+$-ATPase α2 is known from SEQ ID NO:6, the mRNA sequence of Na—K-2Cl cotransporter A1 is known from SEQ ID NO:7, the mRNA sequence of carbonic anhydrase XII, variant 1 is known from SEQ ID NO:101, the mRNA sequence of acetylcholinesterase splice variant E4-E6 is known from SEQ ID NO:123, the mRNA sequence of Na$^+$/K$^+$-ATPase α1, variant 1, is known from SEQ ID NO:124, the mRNA sequence of Na$^+$/K$^+$-ATPase α1, variant 2, is known from SEQ ID NO:125, the mRNA sequence of Na$^+$/K$^+$-ATPase α3 is known from SEQ ID NO:126, the mRNA sequence of Na$^+$/K$^+$-ATPase α4, variant 1, is known from SEQ ID NO:127, the mRNA sequence of Na$^+$/K$^+$-ATPase α4, variant 2, is known from SEQ ID NO:128, the mRNA sequence of Na$^+$/K$^+$-ATPase β1, variant 1, is known from SEQ ID NO:129, the mRNA sequence of Na$^+$/K$^+$-ATPase β1, variant 2, is known from SEQ ID NO:130, the mRNA sequence of Na$^+$/K$^+$-ATPase β2, is known from SEQ ID NO:131, the mRNA sequence of Na$^+$/K$^+$-ATPase β3 is known from SEQ ID NO:132, the mRNA sequence of Na—K-2Cl cotransporter A2 is known from SEQ ID NO:133, and the mRNA sequence of carbonic anhydrase XII, variant 2, is known from SEQ ID NO:134.

Carbonic anhydrases II, IV, and XII mRNA (CA2, CA4, and CA12): Carbonic anhydrases (CAs) II, IV and XII are members of a large family of zinc metalloenzymes that catalyze the reversible hydration of carbon dioxide as described by the GenBank database of the National Center for Biotechnology Information at ncbi.nlm.nih.gov. Carbonic anhydrases are involved in crucial physiological processes such as respiration and transport of $CO_2$/bicarbonate between metabolizing tissues and the lungs, pH and $CO_2$ homeostasis, electrolyte secretion in a variety of tissues and organs, biosynthetic reactions (such as gluconeogenesis, lipogenesis and ureagenesis), bone resorption, calcification, and tumorigenicity.

Fourteen different carbonic anhydrase isozymes have been identified with different subcellular localizations and tissue distributions. Carbonic anhydrase II is a cytosolic isozyme, whereas carbonic anhydrases IV and XII are membrane-bound. Two transcript variants encoding different isoforms have been identified for the CA-XII gene; variant 1 encodes the longer isoform while variant 2 is lacking one of the internal coding exons compared to transcript variant 1 thereby missing an 11 amino acid segment compared to isoform 1. Systemic carbonic anhydrase inhibitors (CAIs) are useful in reducing the elevated intraocular pressure (IOP) that is characteristic of glaucoma. Inhibition of the isozymes present in the ciliary process (the sulfonamide susceptible isozymes CA II and CA IV) reduces the rate of bicarbonate and aqueous humor secretion, which leads to a 25-30% decrease in IOP. However, inhibition of various CA isozymes present in extraocular tissues leads to side effects including numbness and tingling of extremities, metallic taste, depression, fatigue, malaise, weight loss, decreased libido, gastrointestinal irritation, metabolic acidosis, renal calculi, and transient myopia.

The GenBank database provides the DNA sequence for CA2 as accession no. NM_000067, provided in the "Sequence Listing" as SEQ ID NO:1. SEQ ID NO:1 provides the sense strand sequence of DNA that corresponds to the mRNA encoding CAII (with the exception of "T" bases for "U" bases). The coding sequence for CAII is from nucleotides 66-848.

Equivalents of the above cited CA2 mRNA sequence are alternative splice forms, allelic forms, isozymes, or a cognate thereof. A cognate is a CA2 mRNA from another mammalian species that is homologous to SEQ ID NO:1 (i.e., an ortholog). CA2 nucleic acid sequences related to SEQ ID NO:1 include those having GenBank accession numbers M77181, X03251, BC011949, BC035424, CR536526, CR541875, J03037, M36532, S69526, and Y00339.

The GenBank database provides the DNA sequence for CA4 as accession no. NM_000717, provided in the "Sequence Listing" as SEQ ID NO:2. SEQ ID NO:2 provides the sense strand sequence of DNA that corresponds to the mRNA encoding CAIV (with the exception of "T" bases for "U" bases). The coding sequence for CAIV is from nucleotides 47-985.

Equivalents of the above cited CA4 mRNA sequence are alternative splice forms, allelic forms, isozymes, or a cognate thereof. A cognate is a CA4 mRNA from another mammalian species that is homologous to SEQ ID NO:2 (i.e., an ortholog). CA4 nucleic acid sequences related to SEQ ID NO:2 include those having GenBank accession numbers L10955, BC057792, BC069649, BC074768, CR541766, and M83670.

The GenBank database provides the DNA sequence for CA12, variant 1, as accession no. NM_001218, provided in the "Sequence Listing" as SEQ ID NO:101. SEQ ID NO:101 provides the sense strand sequence of DNA that corresponds to the mRNA encoding CAXII, variant 1 (with the exception of "T" bases for "U" bases). The coding sequence for CAXII, variant 1, is from nucleotides 157-1221.

Equivalents of the above cited CA12, variant 1 mRNA sequence are alternative splice forms, allelic forms, isozymes, or a cognate thereof. A cognate is a CA12 mRNA from another mammalian species that is homologous to SEQ ID NO:101 (i.e., an ortholog).

The GenBank database provides the DNA sequence for CA12, variant 2, as accession no. NM_206925, provided in the "Sequence Listing" as SEQ ID NO:134. SEQ ID NO:134 provides the sense strand sequence of DNA that corresponds to the mRNA encoding CAXII, variant 2 (with the exception of "T" bases for "U" bases). The coding sequence for CAXII, variant 2, is from nucleotides 157-1188. Variant 2 lacks an internal coding exon compared to variant 1.

Equivalents of the above cited CA12, variant 2 mRNA sequence are alternative splice forms, allelic forms, isozymes, or a cognate thereof. A cognate is a CA12 mRNA from another mammalian species that is homologous to SEQ ID NO:134 (i.e., an ortholog).

Adrenergic Receptors-β1 and -β2 mRNA (ADRB1 and ADRB2): The adrenergic receptors (subtypes α1, α2, β1, and β2) are a prototypic family of G protein-coupled receptors that mediate the physiological effects of the hormone epinephrine and the neurotransmitter norepinephrine as described by the GenBank database of the National Center for Biotechnology Information at ncbi.nlm.nih.gov.

The GenBank database provides the DNA sequence for ADRB1 as accession no. NM_000684, provided in the "Sequence Listing" as SEQ ID NO:3. SEQ ID NO:3 provides the sense strand sequence of DNA that corresponds to the mRNA encoding β1-adrenergic receptor (with the exception of "T" bases for "U" bases). The coding sequence for β1-adrenergic receptor is from nucleotides 87-1520.

Equivalents of the above cited ADRB1 mRNA sequence are alternative splice forms, allelic forms, or a cognate thereof. A cognate is an ADRB1 mRNA from another mammalian species that is homologous to SEQ ID NO:3 (i.e., an ortholog). ADRB1 nucleic acid sequences related to SEQ ID NO:3 include those having GenBank accession numbers AF169006, AF169007, AY567837, and J03019.

The GenBank database provides the DNA sequence for ADRB2 as accession no. NM_000024, provided below as SEQ ID NO:4. SEQ ID NO:4 provides the sense strand sequence of DNA that corresponds to the mRNA encoding β2-adrenergic receptor (with the exception of "T" bases for "U" bases). The coding sequence for β2-adrenergic receptor is from nucleotides 220-1461.

Equivalents of the above cited ADRB2 mRNA sequence are alternative splice forms, allelic forms, or a cognate thereof. A cognate is an ADRB2 mRNA from another mammalian species that is homologous to SEQ ID NO:4 (i.e., an ortholog). ADRB2 nucleic acid sequences related to SEQ ID NO:4 include those having GenBank accession numbers AF022953, AF022954, AF022955, AF022956, AF169225, AF202305, AF203386, AY011291, J02960, Y00106, AY136741, BC012481, BC063486, BC073856, M15169, and X04827.

Acetylcholinesterase mRNA splice variants E4-E6 and E4-E5 (ACHE): As described by the GenBank database of the National Center for Biotechnology Information at ncbi.nlm.nih.gov, acetylcholinesterase hydrolyzes the neurotransmitter acetylcholine at neuromuscular junctions and brain cholinergic synapses, and thus terminates signal transmission. It is also found on red blood cell membranes, where it constitutes the Yt blood group antigen. Acetylcholinesterase exists in multiple molecular forms which possess similar catalytic properties, but differ in their oligomeric assembly and mode of cell attachment to the cell surface. It is encoded by the single ACHE gene, and the structural diversity in the gene products arises from alternative mRNA splicing, and post-translational associations of catalytic and structural subunits. The major form of acetylcholinesterase found in brain, muscle and other tissues is the hydrophilic species, which forms disulfide-linked oligomers with collagenous, or lipid-containing structural subunits. The other, alternatively spliced form, expressed primarily in the erythroid tissues, differs at the C-terminal end, and contains a cleavable hydrophobic peptide with a GPI-anchor site. It associates with the membranes through the phosphoinositide (PI) moieties added post-translationally. The splice variant E4-E6 is the major transcript and results from the splicing of exon 4 to exon 6. The splice variant E4-E5 results from alternative splicing of exon 4 to exon 5.

The GenBank database provides the DNA sequence for ACHE splice variant E4-E5 as accession no. NM_015831, provided in the "Sequence Listing" as SEQ ID NO:5. SEQ ID NO:5 provides the sense strand sequence of DNA that corresponds to the mRNA encoding acetylcholinesterase E4-E5 (with the exception of "T" bases for "U" bases). The coding sequence for acetylcholinesterase E4-E5 is from nucleotides 95-1948.

Equivalents of the above cited ACHE mRNA sequence are alternative splice forms, allelic forms, or a cognate thereof. A cognate is an ACHE mRNA from another mammalian species that is homologous to SEQ ID NO:5 (i.e., an ortholog). ACHE nucleic acid sequences related to SEQ ID NO:5 include those having GenBank accession numbers AC011895, AF002993, AF312032, AY750146, CH236956, L06484, L42812, S71129, AF334270, BC026315, BC036813, M55040 and NM_000665.

The GenBank database provides the DNA sequence for ACHE splice variant E4-E6 as accession no. NM_000665, provided in the "Sequence Listing" as SEQ ID NO:123. SEQ ID NO:123 provides the sense strand sequence of DNA that corresponds to the mRNA encoding acetylcholinesterase E4-E6 variant (with the exception of "T" bases for "U" bases). The coding sequence for acetylcholinesterase E4-E6 is from nucleotides 95-1939.

Equivalents of the above cited ACHE mRNA sequence are alternative splice forms, allelic forms, or a cognate thereof. A cognate is an ACHE mRNA from another mammalian species that is homologous to SEQ ID NO:123 (i.e., an ortholog). ACHE nucleic acid sequences related to SEQ ID NO:123 include those having GenBank accession numbers NM_015831, AC011895, AF002993, AF312032, AY750146, CH236956, L06484, L42812, S71129, AF334270, BC026315, BC036813, and M55040.

$Na^+/K^+$-ATPase α and β mRNA (ATP1-A1 variant 1, -A1 variant 2, -A2, -A3, -A4 variant 1, -A4 variant 2, -B1 variant 1, -B1 variant 2, -B2, and -B3): As described by the GenBank database, the proteins encoded by these genes belong to the family of P-type cation transport ATPases, and to the subfamily of $Na^+/K^+$-ATPases. $Na^+/K^+$-ATPase is an integral membrane protein responsible for establishing and maintaining the electrochemical gradients of Na and K ions across the plasma membrane. These gradients are essential for osmo-regulation, for sodium-coupled transport of a variety of organic and inorganic molecules, and for electrical excitability of nerve and muscle. This enzyme is composed of two subunits, a large catalytic subunit (α or A) and a smaller glycoprotein subunit (β or B). The catalytic subunit of $Na^+/K^+$-ATPase is encoded by multiple genes.

The GenBank database provides the DNA sequence for ATP1A1 variant 1 as accession no. NM_000701, provided in the "Sequence Listing" as SEQ ID NO:124. SEQ ID NO:124 provides the sense strand sequence of DNA that corresponds to the mRNA encoding $Na^+/K^+$-ATPase subunit A1 variant 1 (with the exception of "T" bases for "U" bases). The coding sequence for $Na^+/K^+$-ATPase subunit A1 variant 1 is from nucleotides 299-3370.

Equivalents of the above cited ATP1A1 variant 1 mRNA sequence are alternative splice forms, allelic forms, or a cognate thereof. A cognate is an ATP1A1 variant 1 mRNA from another mammalian species that is homologous to SEQ ID NO:124 (i.e., an ortholog).

The GenBank database provides the DNA sequence for ATP1A1 variant 2 as accession no. NM_001001586, provided in the "Sequence Listing" as SEQ ID NO:125. SEQ ID NO:125 provides the sense strand sequence of DNA that corresponds to the mRNA encoding $Na^+/K^+$-ATPase subunit A1 variant 2 (with the exception of "T" bases for "U" bases). The coding sequence for $Na^+/K^+$-ATPase subunit A1 variant 2 is from nucleotides 299-2344.

Equivalents of the above cited ATP1A1 variant 2 mRNA sequence are alternative splice forms, allelic forms, or a cognate thereof. A cognate is an ATP1A1 variant 2 mRNA from another mammalian species that is homologous to SEQ ID NO:125 (i.e., an ortholog).

The GenBank database provides the DNA sequence for ATP1A2 as accession no. NM_000702, provided in the "Sequence Listing" as SEQ ID NO:6. SEQ ID NO:6 provides the sense strand sequence of DNA that corresponds to the mRNA encoding $Na^+/K^+$-ATPase A2 subunit (with the exception of "T" bases for "U" bases). The coding sequence for $Na^+/K^+$-ATPase A2 subunit is from nucleotides 105-3167.

Equivalents of the above cited ATP1A2 mRNA sequence are alternative splice forms, allelic forms, or a cognate thereof. A cognate is an ATP1A2 mRNA from another mammalian species that is homologous to SEQ ID NO:6 (i.e., an ortholog). ATP1A2 nucleic acid sequences related to SEQ ID NO:6 include those having GenBank accession numbers J05096, M27578, AB018321, AK091617, AK124581, AK126573, AL831991, AL831997, BC013680, BC047533, BC052271, M16795, and Y07494.

The GenBank database provides the DNA sequence for ATP1A3 as accession no. NM_152296, provided in the "Sequence Listing" as SEQ ID NO:126. SEQ ID NO:126 provides the sense strand sequence of DNA that corresponds to the mRNA encoding $Na^+/K^+$-ATPase A3 subunit (with the exception of "T" bases for "U" bases). The coding sequence for $Na^+/K^+$-ATPase A3 subunit is from nucleotides 155-3196.

Equivalents of the above cited ATP1A3 mRNA sequence are alternative splice forms, allelic forms, or a cognate thereof. A cognate is an ATP1A3 mRNA from another mammalian species that is homologous to SEQ ID NO:126 (i.e., an ortholog).

The GenBank database provides the DNA sequence for ATP1A4 variant 1 as accession no. NM_144699, provided in the "Sequence Listing" as SEQ ID NO:127. SEQ ID NO:127 provides the sense strand sequence of DNA that corresponds to the mRNA encoding $Na^+/K^+$-ATPase A4 subunit variant 1 (with the exception of "T" bases for "U" bases). The coding sequence for $Na^+/K^+$-ATPase A4 subunit variant 1 is from nucleotides 469-3558.

Equivalents of the above cited ATP1A4 variant 1 mRNA sequence are alternative splice forms, allelic forms, or a cognate thereof. A cognate is an ATP1A4 variant 1 mRNA from another mammalian species that is homologous to SEQ ID NO:127 (i.e., an ortholog).

The GenBank database provides the DNA sequence for ATP1A4 variant 2 as accession no. NM_001001734, provided in the "Sequence Listing" as SEQ ID NO:128. SEQ ID NO:128 provides the sense strand sequence of DNA that corresponds to the mRNA encoding $Na^+/K^+$-ATPase A4 subunit variant 2 (with the exception of "T" bases for "U" bases). The coding sequence for $Na^+/K^+$-ATPase A4 subunit variant 2 is from nucleotides 111-608.

Equivalents of the above cited ATP1A4 variant 2 mRNA sequence are alternative splice forms, allelic forms, or a cognate thereof. A cognate is an ATP1A4 variant 2 mRNA from another mammalian species that is homologous to SEQ ID NO:128 (i.e., an ortholog).

The GenBank database provides the DNA sequence for ATP1B1 variant 1 as accession no. NM_001677, provided in the "Sequence Listing" as SEQ ID NO:129. SEQ ID NO:129 provides the sense strand sequence of DNA that corresponds to the mRNA encoding $Na^+/K^+$-ATPase B1 subunit variant 1 (with the exception of "T" bases for "U" bases). The coding sequence for $Na^+/K^+$-ATPase B1 subunit variant 1 is from nucleotides 122-1033.

Equivalents of the above cited ATP1B1 variant 1 mRNA sequence are alternative splice forms, allelic forms, or a cognate thereof. A cognate is an ATP1B1 variant 1 mRNA from another mammalian species that is homologous to SEQ ID NO:129 (i.e., an ortholog).

The GenBank database provides the DNA sequence for ATP1B1 variant 2 as accession no. NM_001001787, provided in the "Sequence Listing" as SEQ ID NO:130. SEQ ID NO:130 provides the sense strand sequence of DNA that corresponds to the mRNA encoding $Na^+/K^+$-ATPase B1 subunit variant 2 (with the exception of "T" bases for "U" bases). The coding sequence for $Na^+/K^+$-ATPase B1 subunit variant 2 is from nucleotides 122-1027.

Equivalents of the above cited ATP1B1 variant 2 mRNA sequence are alternative splice forms, allelic forms, or a cognate thereof. A cognate is an ATP1B1 variant 2 mRNA from another mammalian species that is homologous to SEQ ID NO:130 (i.e., an ortholog).

The GenBank database provides the DNA sequence for ATP1B2 as accession no. NM_001678, provided in the "Sequence Listing" as SEQ ID NO:131. SEQ ID NO:131 provides the sense strand sequence of DNA that corresponds to the mRNA encoding $Na^+/K^+$-ATPase B2 subunit (with the exception of "T" bases for "U" bases). The coding sequence for $Na^+/K^+$-ATPase B2 subunit is from nucleotides 584-1456.

Equivalents of the above cited ATP1B2 mRNA sequence are alternative splice forms, allelic forms, or a cognate thereof. A cognate is an ATP1B2 mRNA from another mammalian species that is homologous to SEQ ID NO:131 (i.e., an ortholog).

The GenBank database provides the DNA sequence for ATP1B3 as accession no. NM_001679, provided in the "Sequence Listing" as SEQ ID NO:132. SEQ ID NO:132 provides the sense strand sequence of DNA that corresponds to the mRNA encoding $Na^+/K^+$-ATPase B3 subunit (with the exception of "T" bases for "U" bases). The coding sequence for $Na^+/K^+$-ATPase B3 subunit is from nucleotides 175-1014.

Equivalents of the above cited ATP1B3 mRNA sequence are alternative splice forms, allelic forms, or a cognate thereof. A cognate is an ATP1B3 mRNA from another mammalian species that is homologous to SEQ ID NO:132 (i.e., an ortholog).

Na—K-2Cl cotransporter mRNA (SLC12A1 and SLC12A2): The sodium-potassium-chloride cotransporter (Na—K-2Cl cotransporter or NKCC) facilitates the coupled cotransport of $Na^+$, $K^+$, and $Cl^-$ ions across the plasma membrane. There are two isoforms: NKCC1 and NKCC2. NKCC1 is expressed in most tissues, including the eye. In contrast, NKCC2 is expressed primarily in the kidney, however, there is evidence for lower level expression of this isoform in the eye as well. NKCC1 is encoded by the SLC12A2 gene (solute carrier family 12, member 2) and NKCC2 is encoded by the SLC12A1 gene. Trabecular meshwork cells possess a robust Na—K-2Cl cotransporter. The activity of this cotransporter is modulated by neurotransmitters and hormones such as norepinephrine, which reduces cotransport activity, or vasopressin, which increases cotransport activity.

The GenBank database provides the DNA sequence for SLC12A1 as accession no. NM_000338, provided in the "Sequence Listing" as SEQ ID NO:7. SEQ ID NO:7 provides the sense strand sequence of DNA that corresponds to the mRNA encoding Na—K-2Cl cotransporter NKCC2 (with the exception of "T" bases for "U" bases). The coding sequence for Na—K-2Cl cotransporter NKCC2 is from nucleotides 20-3319.

Equivalents of the above cited Na—K-2Cl NKCC2 cotransporter mRNA sequence are alternative splice forms, allelic forms, or a cognate thereof. A cognate is a Na—K-2Cl cotransporter NKCC2 mRNA from another mammalian species that is homologous to SEQ ID NO:7 (i.e., an ortholog). SLC12A1 nucleic acid sequences related to SEQ ID NO:7 include those having GenBank accession numbers AJ005332, AJ005333, AB032525, AB032527, BC040138, BX647067, BX647484, and U58130.

The GenBank database provides the DNA sequence for SLC12A2 as accession no. NM_001046, provided in the "Sequence Listing" as SEQ ID NO:133. SEQ ID NO:133 provides the sense strand sequence of DNA that corresponds to the mRNA encoding Na—2Cl cotransporter NKCC1

(with the exception of "T" bases for "U" bases). The coding sequence for Na—K-2Cl cotransporter NKCC1 is from nucleotides 165-3803.

Equivalents of the above cited Na—K-2Cl cotransporter NKCC1 mRNA sequence are alternative splice forms, allelic forms, or a cognate thereof. A cognate is a Na—K-2Cl cotransporter NKCC1 mRNA from another mammalian species that is homologous to SEQ ID NO:133 (i.e., an ortholog).

Attenuating expression of an mRNA: The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention. In one embodiment, a single interfering RNA targeting one of the ocular hypertension targets is administered to lower IOP. In other embodiments, two or more interfering RNAs targeting the same ocular hypertension target (e.g., CA2) are administered to lower IOP. In still other embodiments, two or more interfering RNAs targeting multiple hypertension targets (e.g., CA2 and ADRB2) are administered to lower IOP.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Inhibition of targets cited herein is also inferred in a human or mammal by observing an improvement in a glaucoma symptom such as improvement in intraocular pressure, improvement in visual field loss, or improvement in optic nerve head changes, for example.

Interfering RNA of embodiments of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

Interfering RNA: In one embodiment of the invention, interfering RNA (e.g., siRNA) has a sense strand and an antisense strand, and the sense and antisense strands comprise a region of at least near-perfect contiguous complementarity of at least 19 nucleotides. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA.

The length of each strand of the interfering RNA comprises 19 to 49 nucleotides, and may comprise a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression.

In the present invention, interfering RNA target sequences (e.g., siRNA target sequences) within a target mRNA sequence are selected using available design tools. Interfering RNAs corresponding to these target sequences are then tested by transfection of cells expressing the target mRNA followed by assessment of knockdown as described above. Interfering RNAs that produce a knockdown in expression of between 50% and 100% are selected for further analysis.

Techniques for selecting target sequences for siRNAs are provided by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA.

An embodiment of a 19-nucleotide DNA target sequence for carbonic anyhdrase II is present at nucleotides 232 to 250 of SEQ ID NO:1:

```
5'-CCCTGAGGATCCTCAACAA-3'.      SEQ ID NO: 8
```

An siRNA of the invention for targeting a corresponding mRNA sequence of SEQ ID NO:8 and having 21-nucleotide strands and a 2-nucleotide 3' overhang is:

```
5'-CCCUGAGGAUCCUCAACAANN-3'     SEQ ID NO: 9
3'-NNGGGACUCCUAGGAGUUGUU-5'.    SEQ ID NO: 10
```

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An siRNA of the invention for targeting a corresponding mRNA sequence of SEQ ID NO:8 and having 21-nucleotide strands and a 3'UU overhang on each strand is:

```
5'-CCCUGAGGAUCCUCAACAAUU-3'     SEQ ID NO: 11
3'-UUGGGACUCCUAGGAGUUGUU-5'.    SEQ ID NO: 12
```

The interfering RNA may also have a 5' overhang of nucleotides or it may have blunt ends. An siRNA of the invention for targeting a corresponding mRNA sequence of SEQ ID NO:8 and having 19-nucleotide strands and blunt ends is:

```
5'-CCCUGAGGAUCCUCAACAA-3'       SEQ ID NO: 722
3'-GGGACUCCUAGGAGUUGUU-5'.      SEQ ID NO: 723
```

The strands of a double-stranded interfering RNA (e.g., an siRNA) may be connected to form a hairpin or stem-loop structure (e.g., an shRNA). An shRNA of the invention targeting a corresponding mRNA sequence of SEQ ID NO:8 and having a 19 bp double-stranded stem region and a 3'UU overhang is:

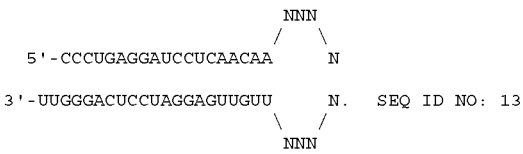

```
                    NNN
                  /     \
    5'-CCCUGAGGAUCCUCAACAA   N
    3'-UUGGGACUCCUAGGAGUUGUU   N.    SEQ ID NO: 13
                  \     /
                    NNN
```

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) *Science* 296: 550) and 5'-UUUGUGUAG-3' (Castanotto, D. et al. (2002) *RNA* 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3' end to facilitate the design of dicer-substrate 27-mer duplexes. Extension of the 19-nucleotide DNA target sequence (SEQ ID NO:8) identified in the carbonic anhydrase II DNA sequence (SEQ ID NO:1) by 6 nucleotides yields a 25-nucleotide DNA target sequence present at nucleotides 232 to 256 of SEQ ID NO:1:

```
5'-CCCTGAGGATCCTCAACAATGGTCA-3'.    SEQ ID NO: 724
```

A dicer-substrate 27-mer duplex of the invention for targeting a corresponding mRNA sequence of SEQ ID NO:724 is:

```
    5'-CCCUGAGGAUCCUCAACAAUGGUCA-3'   SEQ ID NO: 718
3'-UUGGGACUCCUAGGAGUUGUUACCAGU-5'.   SEQ ID NO: 719
```

The two nucleotides at the 3' end of the sense strand (i.e., the CA nucleotides of SEQ ID NO:718) may be deoxynucleotides for enhanced processing. Design of dicer-substrate 27-mer duplexes from 19-21 nucleotide target sequences, such as provided herein, is further discussed by the Integrated DNA Technologies (IDT) website and by Kim, D.-H. et al., (February, 2005) *Nature Biotechnology* 23:2; 222-226.

When interfering RNAs are produced by chemical synthesis, phosphorylation at the 5' position of the nucleotide at the 5' end of one or both strands (when present) can enhance siRNA efficacy and specificity of the bound RISC complex but is not required since phosphorylation can occur intracellularly.

Table 1 lists examples of siRNA target sequences within the CA2, CA4, and CA12 variant 1 and variant 2 DNA sequences (SEQ ID NO:1, SEQ ID NO:2, SEQ ID NO:101, and SEQ ID NO:134, respectively) from which siRNAs of the present invention are designed in a manner as set forth above. CA2, CA4, and CA12 variant 1 and variant 2 encode carbonic anhydrase II, IV, and XII variant 1 and 2, respectively.

TABLE 1

CA2, CA4, and CA12 Target Sequences for siRNAs

| CA2 Target Sequence | # of Starting Nucleotide with reference to SEQ ID NO: 1 | SEQ ID NO: |
|---|---|---|
| CCCTGAGGATCCTCAACAA | 232 | 8 |
| GGGCCTTCAGAAAGTTGTT | 527 | 14 |
| GCGAGCAGGTGTTGAAATT | 721 | 15 |
| GGTGTTGAAATTCCGTAAA | 728 | 16 |
| GCCACTGAAGAACAGGCAA | 809 | 17 |
| CCACTGAAGAACAGGCAAA | 810 | 18 |
| CCCATAGTCTGTATCCAAA | 855 | 19 |
| CCATAGTCTGTATCCAAAT | 856 | 20 |
| GGTGATTTGGACCCTGGTT | 921 | 21 |
| GGGTGATGAGCACTCACAA | 1139 | 22 |
| GAAGGTTGGCAGCGCTAAA | 506 | 83 |
| ATGTGCTGGATTCCATTAA | 547 | 84 |
| TGTGCTGGATTCCATTAAA | 548 | 85 |
| CCGTAAACTTAACTTCAAT | 740 | 86 |
| GATCTACCTTGGTGATTTG | 911 | 87 |
| GACCAATTGTCATGCTTGA | 1009 | 88 |
| GGTGATGAGCACTCACAAT | 1140 | 89 |
| CACTCACAATTGTTGACTA | 1149 | 90 |
| ACTCACAATTGTTGACTAA | 1150 | 91 |
| CTCACAATTGTTGACTAAA | 1151 | 92 |
| AGGAAAGTAGAATGGTTGA | 1188 | 93 |
| GTAGAATGGTTGAGTGCAA | 1194 | 94 |
| TAGAATGGTTGAGTGCAAA | 1195 | 95 |
| CAAGATAAATTGAGCTAGT | 1223 | 96 |
| AGTTAAGGCAAATCAGGTA | 1239 | 97 |
| GAGTTGTGATACAGAGTAT | 1456 | 98 |
| AGTTGTGATACAGAGTATA | 1457 | 99 |
| GTTGTGATACAGAGTATAT | 1458 | 100 |
| GACCTGAGCACTGGCATAA | 100 | 135 |
| TGACATCGACACTCATACA | 158 | 136 |
| ACACTCATACAGCCAAGTA | 166 | 137 |
| ACAATGGTCATGCTTTCAA | 247 | 138 |
| AGGACAAAGCAGTGCTCAA | 286 | 139 |
| GATGGCACTTACAGATTGA | 318 | 140 |
| GCACTTACAGATTGATTCA | 322 | 141 |
| ACAGATTGATTCAGTTTCA | 328 | 142 |

TABLE 1-continued

| CA4 Target Sequence | # of Starting Nucleotide with reference to SEQ ID NO: 2 | SEQ ID NO: |
|---|---|---|
| ACAAGGTTCAGAGCATACT | 371 | 143 |
| CAGAACTTCACTTGGTTCA | 412 | 144 |
| ACTGGCCGTTCTAGGTATT | 482 | 145 |
| TTGAAGGTTGGCAGCGCTA | 504 | 146 |
| TGAAGGTTGGCAGCGCTAA | 505 | 147 |
| TTGTTGATGTGCTGGATTC | 541 | 148 |
| GAAATTCCGTAAACTTAAC | 734 | 149 |
| CCGAAGAACTGATGGTGGA | 772 | 150 |
| GAACTGATGGTGGACAACT | 777 | 151 |
| TGAAGAACAGGCAAATCAA | 814 | 152 |
| CTTACTTGATAGACTTACT | 972 | 153 |
| TGTGAAGACTAGACCAATT | 998 | 154 |
| TTGAGCTAGTTAAGGCAAA | 1232 | 155 |
| GGATGGCACTTACAGATTG | 317 | 720 |
| GAAATATGCTGCAGAACTT | 401 | 721 |

| CA4 Target Sequence | # of Starting Nucleotide with reference to SEQ ID NO: 2 | SEQ ID NO: |
|---|---|---|
| TCGTCACCACCAAGGCAAA | 213 | 23 |
| GCTTCTTCTTCTCTGGCTA | 252 | 24 |
| TCTTCTCTGGCTACGATAA | 258 | 25 |
| GGCTACGATAAGAAGCAAA | 266 | 26 |
| GGTCCGACTTGCCATATAA | 399 | 27 |
| GGAGATGCACATAGTACAT | 457 | 28 |
| GCACATAGTACATGAGAAA | 463 | 29 |
| GACATCGAGGAATGTGAAA | 490 | 30 |
| GGTGGAGGCACTGTCTAAT | 595 | 31 |
| GGGACTTTAGGCATGATTA | 1064 | 32 |
| ACACTGGTGCTACGAGGTT | 109 | 156 |
| CTGGTGCTACGAGGTTCAA | 112 | 157 |
| GTTCAAGCCGAGTCCTCCA | 125 | 158 |
| TTCAAGCCGAGTCCTCCAA | 126 | 159 |
| CCTGCTTGGTGCCAGTCAA | 150 | 160 |
| TCTCTGGCTACGATAAGAA | 261 | 161 |
| TGGCTACGATAAGAAGCAA | 265 | 162 |
| GCAAACGTGGACTGTCCAA | 280 | 163 |
| TGGTCCGACTTGCCATATA | 398 | 164 |
| CCATGGAGATGCACATAGT | 453 | 165 |
| AGATGCACATAGTACATGA | 459 | 166 |
| TGCACATAGTACATGAGAA | 462 | 167 |

| CA12, variant 1 and 2 Common Target Sequences | # of Starting Nucleotide with reference to SEQ ID NO: 101 | SEQ ID NO: |
|---|---|---|
| ATAGTACATGAGAAAGAGA | 467 | 168 |
| CATCGAGGAATGTGAAAGA | 492 | 169 |
| TTGCGGTGCTGGCCTTTCT | 534 | 170 |
| GAACAGATCCTGGCATTCT | 785 | 171 |
| TCTCTCAGAAGCTGTACTA | 801 | 172 |
| AGGAACAGACAGTGAGCAT | 825 | 173 |
| GAACAGACAGTGAGCATGA | 827 | 174 |
| GGCAGCGCACGGTGATAAA | 876 | 175 |
| CAGCCTCTCTGTTGCCTCA | 1003 | 176 |
| TGTTGCCTCAGCTCTCCAA | 1012 | 177 |

| CA12, variant 1 and 2 Common Target Sequences | # of Starting Nucleotide with reference to SEQ ID NO: 101 | SEQ ID NO: |
|---|---|---|
| TCCTGCTGGTGATCTTAAA | 191 | 102 |
| ACGGTTCCAAGTGGACTTA | 239 | 103 |
| GAGAATAGCTGGTCCAAGA | 274 | 104 |
| AGAATAGCTGGTCCAAGAA | 275 | 105 |
| GTGACATCCTCCAGTATGA | 341 | 106 |
| GCTACAATCTGTCTGCCAA | 389 | 107 |
| CAGTTTCTCCTGACCAACA | 412 | 108 |
| AGTTTCTCCTGACCAACAA | 413 | 109 |
| GACCAACAATGGCCATTCA | 423 | 110 |
| CTCCTTCAATCCGTCCTAT | 687 | 111 |
| CCTTCAATCCGTCCTATGA | 689 | 112 |
| ATCCGTCCTATGACAAGAT | 695 | 113 |
| AGATCTTCAGTCACCTTCA | 710 | 114 |
| CGGAGAGGACCGCTGAATA | 791 | 115 |
| GGAGAGGACCGCTGAATAT | 792 | 116 |
| AGAGGACCGCTGAATATTA | 794 | 117 |
| AGGTCCAGAAGTTCGATGA | 983 | 118 |
| GTTCGATGAGAGGCTGGTA | 993 | 119 |
| TTCGATGAGAGGCTGGTAT | 994 | 120 |
| TCGATGAGAGGCTGGTATA | 995 | 121 |
| TTCAATCCGTCCTATGACA | 691 | 178 |

| CA12, variant 1 Target Sequence | # of Starting Nucleotide with reference to SEQ ID NO: 101 | SEQ ID NO: |
|---|---|---|
| TGTACTGCGGCAGGACTGA | 1039 | 122 |
| AGAGCGTGCTTTCAAGTGT | 1568 | 179 |

TABLE 1-continued

| | | |
|---|---|---|
| GATGTCAAATCGTGGTTTA | 2326 | 180 |
| AAATCGTGGTTTAGATCAA | 2332 | 181 |
| ATGGAATGCTACTAAGATA | 2425 | 182 |
| CTACTAAGATACTCCATAT | 2433 | 183 |
| ACAACGATGGCAAGCCTTA | 2844 | 184 |
| CAACGATGGCAAGCCTTAT | 2845 | 185 |
| TTGCTAGGCAAAGTTACAA | 2880 | 186 |
| TAGGCAAAGTTACAAGTGA | 2884 | 187 |
| AGTTACAAGTGACCTAATG | 2891 | 188 |
| TGTGCACTCAAGACCTCTA | 2954 | 189 |
| GTGCACTCAAGACCTCTAA | 2955 | 190 |
| TGCACTCAAGACCTCTAAC | 2956 | 191 |
| GCACTCAAGACCTCTAACA | 2957 | 192 |
| AGACCTCTAACAGCCTCGA | 2964 | 193 |
| GACCTCTAACAGCCTCGAA | 2965 | 194 |
| TGCCATTAGCATGCCTCAT | 3006 | 195 |
| GCCATTAGCATGCCTCATG | 3007 | 196 |
| TAGCATGCCTCATGCATCA | 3012 | 197 |
| CATCATCAGATGACAAGGA | 3026 | 198 |

| CA12, variant 2 Target Sequence | # of Starting Nucleotide with reference to SEQ ID NO: 134 | SEQ ID NO: |
|---|---|---|
| CTCCTTCAATCCGTCCTAT | 687 | 199 |
| AGAGCGTGCTTTCAAGTGT | 1535 | 200 |
| GATGTCAAATCGTGGTTTA | 2293 | 201 |
| AAATCGTGGTTTAGATCAA | 2299 | 202 |
| ATGGAATGCTACTAAGATA | 2392 | 203 |
| CTACTAAGATACTCCATAT | 2400 | 204 |
| ACAACGATGGCAAGCCTTA | 2811 | 205 |
| CAACGATGGCAAGCCTTAT | 2812 | 206 |
| TTGCTAGGCAAAGTTACAA | 2847 | 207 |
| TAGGCAAAGTTACAAGTGA | 2851 | 208 |
| AGTTACAAGTGACCTAATG | 2858 | 209 |
| TGTGCACTCAAGACCTCTA | 2921 | 210 |
| GTGCACTCAAGACCTCTAA | 2922 | 211 |
| TGCACTCAAGACCTCTAAC | 2923 | 212 |
| GCACTCAAGACCTCTAACA | 2924 | 213 |
| AGACCTCTAACAGCCTCGA | 2931 | 214 |
| GACCTCTAACAGCCTCGAA | 2932 | 215 |
| TGCCATTAGCATGCCTCAT | 2973 | 216 |

TABLE 1-continued

| | | |
|---|---|---|
| GCCATTAGCATGCCTCATG | 2974 | 217 |
| TAGCATGCCTCATGCATCA | 2979 | 218 |
| CATCATCAGATGACAAGGA | 2993 | 219 |

Table 2 lists examples of siRNA target sequences within the ADRB1 and ADRB2 DNA sequences (SEQ ID NO:3 and SEQ ID NO:4, respectively) from which siRNAs of the present invention are designed in a manner as set forth above. As noted above, ADRB1 and ADRB2 encode the β1- and β2-adrenergic receptors, respectively.

TABLE 2

ADRB1 and ADRB2 Target Sequences for siRNAs

| ADRB1 Target Sequence | # of Starting Nucleotide with reference to SEQ ID NO: 3 | SEQ ID NO: |
|---|---|---|
| TCCTTCTTCTGCGAGCTGT | 468 | 33 |
| TCGAGACCCTGTGTGTCAT | 523 | 34 |
| GCATCATGGCCTTCGTGTA | 799 | 35 |
| GAACGAGGAGATCTGTGTT | 1563 | 36 |
| ACGAGGAGATCTGTGTTTA | 1565 | 37 |
| GGAGATCTGTGTTTACTTA | 1569 | 38 |
| GATAGCAGGTGAACTCGAA | 1593 | 39 |
| CCCACAATCCTCGTCTGAA | 1613 | 40 |
| CCACAATCCTCGTCTGAAT | 1614 | 41 |
| TCTGAATCATCCGAGGCAA | 1626 | 42 |
| GCAATGTGCTGGTGATCGT | 310 | 220 |
| TGATCGTGGCCATCGCCAA | 322 | 221 |
| AAGTGCTGCGACTTCGTCA | 726 | 222 |
| CGTCCGTAGTCTCCTTCTA | 769 | 223 |
| CCGTAGTCTCCTTCTACGT | 772 | 224 |
| ATCATGGCCTTCGTGTACC | 801 | 225 |
| TCATGGCCTTCGTGTACCT | 802 | 226 |
| CCTCGGAATCCAAGGTGTA | 1501 | 227 |
| TGTGTTTACTTAAGACCGA | 1576 | 228 |
| GTGTTTACTTAAGACCGAT | 1577 | 229 |
| GTTTACTTAAGACCGATAG | 1579 | 230 |
| TTTACTTAAGACCGATAGC | 1580 | 231 |
| TTACTTAAGACCGATAGCA | 1581 | 232 |
| TAAGACCGATAGCAGGTGA | 1586 | 233 |
| ACCGATAGCAGGTGAACTC | 1590 | 234 |
| CGATAGCAGGTGAACTCGA | 1592 | 235 |
| ATAGCAGGTGAACTCGAAG | 1594 | 236 |

TABLE 2-continued

| | | |
|---|---|---|
| CACAATCCTCGTCTGAATC | 1615 | 237 |
| ACAATCCTCGTCTGAATCA | 1616 | 238 |
| TCATCCGAGGCAAAGAGAA | 1632 | 239 |
| CATCCGAGGCAAAGAGAAA | 1633 | 240 |
| CCACGGACCGTTGCACAAA | 1654 | 241 |

| ADRB2 Target Sequence | # of Starting Nucleotide with reference to SEQ ID NO: 4 | SEQ ID NO: |
|---|---|---|
| GCATCGTCATGTCTCTCAT | 329 | 43 |
| GCTGGTCATCACAGCCATT | 375 | 44 |
| CCCTCAAGACGTTAGGCAT | 1031 | 45 |
| GCATCATCATGGGCACTTT | 1046 | 46 |
| CCTAAATTGGATAGGCTAT | 1149 | 47 |
| GCTATGTCAATTCTGGTTT | 1163 | 48 |
| GGAAGACTTTGTGGGCCAT | 1371 | 49 |
| GCCTAGCGATAACATTGAT | 1401 | 50 |
| GGGAGGAATTGTAGTACAA | 1426 | 51 |
| GCTGTGAACATGGACTCTT | 1880 | 52 |
| CACGACGTCACGCAGCAAA | 283 | 242 |
| GATCGCTACTTTGCCATTA | 607 | 243 |
| ATCGCTACTTTGCCATTAC | 608 | 244 |
| TCGCTACTTTGCCATTACT | 609 | 245 |
| GCCATTACTTCACCTTTCA | 619 | 246 |
| TTACTTCACCTTTTCAAGTA | 623 | 247 |
| CCATTCAGATGCACTGGTA | 722 | 248 |
| TGATCATGGTCTTCGTCTA | 857 | 249 |
| AGACGTTAGGCATCATCAT | 1037 | 250 |
| TCGTTAACATTGTGCATGT | 1091 | 251 |
| AGGATAACCTCATCCGTAA | 1115 | 252 |
| TCATCCGTAAGGAAGTTTA | 1124 | 253 |
| AAGTTTACATCCTCCTAAA | 1136 | 254 |
| AGTTTACATCCTCCTAAAT | 1137 | 255 |
| TAAATTGGATAGGCTATGT | 1151 | 256 |
| CTATGTCAATTCTGGTTTC | 1164 | 257 |
| GGTACTGTGCCTAGCGATA | 1393 | 258 |
| GTACTGTGCCTAGCGATAA | 1394 | 259 |
| TACTGTGCCTAGCGATAAC | 1395 | 260 |
| GCGATAACATTGATTCACA | 1406 | 261 |
| CGATAACATTGATTCACAA | 1407 | 262 |

TABLE 2-continued

| | | |
|---|---|---|
| GGAGGAATTGTAGTACAAA | 1427 | 263 |
| GAGGAATTGTAGTACAAAT | 1428 | 264 |
| AGGAATTGTAGTACAAATG | 1429 | 265 |
| CAAATGACTCACTGCTGTA | 1442 | 266 |
| GACCTGAGTCTGCTATATT | 1725 | 267 |
| ACCTGAGTCTGCTATATTT | 1726 | 268 |
| CCATGTATCTACCTCACTA | 1756 | 269 |
| CATGTATCTACCTCACTAT | 1757 | 270 |
| ATGTATCTACCTCACTATT | 1758 | 271 |
| CCTCACTATTCAAGTATTA | 1767 | 272 |
| TAATATATTGCTGCTGGTA | 1790 | 273 |
| AATATATTGCTGCTGGTAA | 1791 | 274 |
| ATATATTGCTGCTGGTAAT | 1792 | 275 |
| TATATTGCTGCTGGTAATT | 1793 | 276 |
| CTGGTAATTTGTATCTGAA | 1803 | 277 |
| GAGTATCTCGGACCTTTCA | 1861 | 278 |
| CGGACCTTTCAGCTGTGAA | 1869 | 279 |
| CGAGCAAAGGTCTAAAGTT | 1971 | 280 |
| GAGCAAAGGTCTAAAGTTT | 1972 | 281 |
| GGTCTAAAGTTTACAGTAA | 1979 | 282 |

Table 3 lists examples of siRNA target sequences within the ACHE DNA sequences for splice variants E4-E5 and E4-E6 (SEQ ID NO:5 and SEQ ID NO:123, respectively) from which siRNAs of the present invention are designed in a manner as set forth above. As noted above, ACHE encodes acetylcholinesterase.

TABLE 3

ACHE Target Sequences for siRNAs

| ACHE E4-E5 Target Sequence | # of Starting Nucleotide with reference to SEQ ID NO: 5 | SEQ ID NO: |
|---|---|---|
| CCAGAGTGTCTGCTACCAA | 382 | 53 |
| GCTACCAATATGTGGACAC | 393 | 54 |
| CCAATATGTGGACACCCTA | 397 | 55 |
| GCTGGTGTCCATGAACTAC | 622 | 56 |
| TCATCAACGCGGGAGACTT | 1131 | 57 |
| GGTCTACGCCTACGTCTTT | 1459 | 58 |
| GCTACGAGATCGAGTTCAT | 1530 | 59 |
| GCTATAACGGTCAACCATT | 2251 | 60 |
| GGCTGCAAATAAACTGTTA | 2885 | 61 |
| GCTGCAAATAAACTGTTAC | 2886 | 62 |

TABLE 3-continued

| | | |
|---|---|---|
| AGTGTCTGCTACCAATATG | 386 | 283 |
| AGACAACGAGTCTCTCATC | 1231 | 284 |
| GGCTGTGGTCCTGCATTAC | 1315 | 285 |
| CTTCCTCCTCAAACCGAGA | 2047 | 286 |
| TCCTCCTCAAACCGAGAGA | 2049 | 287 |
| CCTCAAACCGAGAGACTCA | 2053 | 288 |
| TCAAACCGAGAGACTCACA | 2055 | 289 |
| AAACCGAGAGACTCACACT | 2057 | 290 |
| CCACGCCTTTGTTGTTTGA | 2125 | 291 |
| CACGCCTTTGTTGTTTGAA | 2126 | 292 |
| ACGCCTTTGTTGTTTGAAT | 2127 | 293 |
| GGCTATAACGGTCAACCAT | 2250 | 294 |
| TATAACGGTCAACCATTTC | 2253 | 295 |
| CGGTCAACCATTTCTGTCT | 2258 | 296 |
| GTCAACCATTTCTGTCTCT | 2260 | 297 |
| CCGTCTTCCGGTCATTCTT | 2318 | 298 |
| CCTCTCGTCTTTCGCACAT | 2395 | 299 |
| TCTCGTCTTTCGCACATTC | 2397 | 300 |
| TTTCGCACATTCTCCTGAT | 2404 | 301 |
| TTCGCACATTCTCCTGATC | 2405 | 302 |
| AGAACCAGTTCGACCACTA | 2643 | 303 |
| AACCAGTTCGACCACTACA | 2645 | 304 |
| CTGCAAATAAACTGTTACA | 2887 | 305 |

| ACHE E4-E5 and E4-E6 Target Sequences in Common | # of Starting Nucleotide with reference to SEQ ID NO: 5 | SEQ ID NO: |
|---|---|---|
| TAGACGCTACAACCTTCCA | 366 | 306 |
| CGCTACAACCTTCCAGAGT | 370 | 307 |
| AGAGTGTCTGCTACCAATA | 384 | 308 |
| GAGTGTCTGCTACCAATAT | 385 | 309 |
| CTGTCCTCGTCTGGATCTA | 525 | 310 |
| ATGGCCGCTTCTTGGTACA | 588 | 311 |
| CGACATCAGTGACGCTGTT | 768 | 312 |
| GCACGTGCTGCCTCAAGAA | 1045 | 313 |
| CACGTGCTGCCTCAAGAAA | 1046 | 314 |
| GAAAGCGTCTTCCGGTTCT | 1061 | 315 |
| TGTGGTAGATGGAGACTTC | 1090 | 316 |
| GACAACGAGTCTCTCATCA | 1232 | 317 |
| AGGCTGTGGTCCTGCATTA | 1314 | 318 |
| GCTGTGGTCCTGCATTACA | 1316 | 319 |

TABLE 3-continued

| | | |
|---|---|---|
| GTCTACGCCTACGTCTTTG | 1460 | 320 |
| TCTACGCCTACGTCTTTGA | 1461 | 321 |
| CTACGCCTACGTCTTTGAA | 1462 | 322 |
| CGGCTACGAGATCGAGTTC | 1528 | 323 |
| CAGCGACTGATGCGATACT | 1607 | 324 |
| GGCTCAGCAGTACGTTAGT | 1705 | 325 |
| AGTACGTTAGTCTGGACCT | 1713 | 326 |

| ACHE E4-E6 Target Sequence | # of Starting Nucleotide with reference to SEQ ID NO: 123 | SEQ ID NO: |
|---|---|---|
| ACATGGTGCACTGGAAGAA | 1875 | 327 |
| AGAACCAGTTCGACCACTA | 1890 | 328 |
| GAACCAGTTCGACCACTAC | 1891 | 329 |
| GGCTATAACACAGACGAGC | 2011 | 330 |
| GCTATAACACAGACGAGCC | 2012 | 331 |
| GCTGCAAATAAACTGTTAC | 2133 | 332 |
| CTGCAAATAAACTGTTACA | 2134 | 333 |

Table 4 lists examples of siRNA target sequences within the Na$^+$/K$^+$-ATPase A and B subunit DNA sequences (ATP1A1 variant 1, SEQ ID NO:124; ATP1A1 variant 2, SEQ ID NO:125; ATP1A2, SEQ ID NO:6; ATP1A3, SEQ ID NO:126; ATP1A4 variant 1, SEQ ID NO:127; ATP1A4 variant 2, SEQ ID NO:128; ATP1B1 variant 1, SEQ ID NO:129; ATP1B1 variant 2, SEQ ID NO:130; ATP1B2, SEQ ID NO:131; and ATP1B3, SEQ ID NO:132) from which siRNAs of the present invention are designed in a manner as set forth above.

TABLE 4

ATP1A and ATP1B Target Sequences for siRNAs

| ATP1A1 variant 1 Target Sequence | # of Starting Nucleotide with reference to SEQ ID NO: 124 | SEQ ID NO: |
|---|---|---|
| GCAATGAGACCGTGGAAGA | 2208 | 334 |
| TGCCAAGGCCTGCGTAGTA | 2275 | 335 |
| TAAAGGACATGACCTCCGA | 2307 | 336 |
| AGCAAGCTGCTGACATGAT | 2526 | 337 |
| ACATGATTCTTCTGGATGA | 2538 | 338 |
| GTCGTCTGATCTTTGATAA | 2592 | 339 |
| CTTATACCTTAACCAGTAA | 2628 | 340 |
| GGATCAACGATGTGGAAGA | 2979 | 341 |
| ACGATGTGGAAGACAGCTA | 2985 | 342 |
| CCGACTTGGTCATCTGTAA | 3093 | 343 |

TABLE 4-continued

| | # of Starting Nucleotide with reference to | |
|---|---|---|
| ATP1A1 Target Sequence | SEQ ID NO: | SEQ ID NO: |
| TAGGAAAGCACCGCAGCAT | 3474 | 344 |
| AGACGTCCTGGAATGAAGC | 3504 | 345 |
| GACGTCCTGGAATGAAGCA | 3505 | 346 |
| ACGTCCTGGAATGAAGCAT | 3506 | 347 |
| GAAGCATGTAGCTCTATGG | 3518 | 348 |

| ATP1A1 variant 1 and variant 2 Common Target Sequences | # of Starting Nucleotide with reference to SEQ ID NO: 124 | SEQ ID NO: |
|---|---|---|
| TTCAGAACAAGGTGATAAA | 343 | 349 |
| TGATGAACTTCATCGTAAA | 442 | 350 |
| GGTGCTATCAGCCGTTGTA | 700 | 351 |
| TCAGCCGTTGTAATCATAA | 707 | 352 |
| GATTCGAAATGGTGAGAAA | 811 | 353 |
| CAGAATCATATCTGCAAAT | 907 | 354 |
| CACGTGGTATTGTTGTCTA | 1059 | 355 |
| CTGCTTAGTGAAGAACTTA | 1363 | 356 |
| GTTTCAGGCTAACCAGGAA | 1594 | 357 |
| CACTCTTAAAGTGCATAGA | 1662 | 358 |
| AGTACCAGTTGTCTATTCA | 1758 | 359 |
| TACCAGTTGTCTATTCATA | 1760 | 360 |
| AGCTGAAAGACGCCTTTCA | 1896 | 361 |
| TCGATAATCTGTGCTTTGT | 2037 | 362 |
| ACAGGAGACCATCCAATCA | 2147 | 363 |

| ATP1A1 variant 2 Target Sequence | # of Starting Nucleotide with reference to SEQ ID NO: 125 | SEQ ID NO: |
|---|---|---|
| TAGCCTTGATGAACTTCAT | 436 | 364 |
| TTGATGAACTTCATCGTAA | 441 | 365 |
| GATGAACTTCATCGTAAAT | 443 | 366 |
| CTACTCCTGAATGGATCAA | 552 | 367 |
| GGAGCGATTCTTTGTTTCT | 617 | 368 |
| GTGCTATCAGCCGTTGTAA | 701 | 369 |
| TGCTATCAGCCGTTGTAAT | 702 | 370 |
| GAGCATAAATGCGGAGGAA | 832 | 371 |
| GAAGGCAATGGACCTATGA | 2204 | 372 |
| CCGACTTGGTCATCTGTAA | 2291 | 373 |
| TATATGACGAAGTCAGAAA | 2495 | 374 |

| ATP1A2 Target Sequence | # of Starting Nucleotide with reference to SEQ ID NO: 6 | SEQ ID NO: |
|---|---|---|
| CCATCCAACGACAATCTAT | 471 | 63 |
| GCATCATATCAGAGGGTAA | 1990 | 64 |
| CCTCCTCATCTTCATCTAT | 3080 | 65 |
| GGAAGTGAGGTAGTGCCAA | 3797 | 66 |
| GGATGTCACTCATGTACTT | 4037 | 67 |
| GCTCCATGCTGTTCTGAAA | 4093 | 68 |
| GCTGGCCATTGGCTAGAAT | 4225 | 69 |
| GGTCAGAACCTTTGGACAA | 4323 | 70 |
| GCTAGAGGTGGCATGTTTA | 5213 | 71 |
| GCGAGTGCATGGGCTAATT | 5285 | 72 |
| TGGCAATGGATGACCACAA | 214 | 375 |
| TGAACCATCCAACGACAAT | 467 | 376 |
| ACCATCCAACGACAATCTA | 470 | 377 |
| CATCCAACGACAATCTATA | 472 | 378 |
| ATCCAACGACAATCTATAT | 473 | 379 |
| GCAGATCAACGCAGAGGAA | 632 | 380 |
| TGTTTCTTCTCCACCAACT | 825 | 381 |
| CCATAGCAATGGAGATTGA | 946 | 382 |
| AGATGCAAGATGCCTTTCA | 1693 | 383 |
| CTGAATCTGCCATCTGGAA | 1767 | 384 |
| TGAATCTGCCATCTGGAAA | 1768 | 385 |
| ATCGTCTTTGCTGAACGT | 2157 | 386 |
| CTGCATTGAAGAAGGCTGA | 2263 | 387 |
| ATGAAGCGGCAGCCACGAA | 2589 | 388 |
| TGAAGCGGCAGCCACGAAA | 2590 | 389 |
| GGATGACCGGACCATGAAT | 2765 | 390 |
| GCTGCCTTTCTCTCTTACT | 2988 | 391 |
| TCTATGATGAGGTCCGAAA | 3094 | 392 |
| GTGGAGAAGGAGACATACT | 3144 | 393 |
| TGGAGAAGGAGACATACTA | 3145 | 394 |
| TAGACCTAACTGTGAACAA | 3344 | 395 |
| AGACCTAACTGTGAACAAT | 3345 | 396 |
| TCCACTATGTTGTCTATTT | 3418 | 397 |
| TGAGTGCAAGAGCCTGAGA | 3666 | 398 |

TABLE 4-continued

| | | |
|---|---|---|
| TGACATGAGTCTCCAGATA | 3828 | 399 |
| GTCGTGGACTCCAGCTCTA | 3850 | 400 |
| TGTCACTCATGTACTTAAT | 4040 | 401 |
| GTCACTCATGTACTTAATA | 4041 | 402 |
| CACTTCACCTTCTGTAATA | 4061 | 403 |
| GTAGAGAGAGACCTAGATA | 4882 | 404 |
| CTAGATAGGTCATGCAAGT | 4894 | 405 |
| AGGTCATGCAAGTGAGAAA | 4900 | 406 |
| TATCAGAAGCAAGGAAGTA | 5040 | 407 |
| TCCGATTAATTGGAGATTA | 5114 | 408 |
| CCGATTAATTGGAGATTAC | 5115 | 409 |
| GATTACTAACTGTGGACAA | 5128 | 410 |
| ATTACTAACTGTGGACAAA | 5129 | 411 |
| TCAGGCACTTTAGAAATAT | 5253 | 412 |
| GGCTAATTATCATCAATCT | 5296 | 413 |
| AGTTTGAGGTACTACCTAT | 5375 | 414 |
| TACTACCTATGTACTTGAA | 5384 | 415 |
| ACTACCTATGTACTTGAAA | 5385 | 416 |

| ATP1A3 Target Sequence | # of Starting Nucleotide with reference to SEQ ID NO: 126 | SEQ ID NO: |
|---|---|---|
| TGGCTATGACAGAGCACAA | 240 | 417 |
| GAGGTCTGCCGGAAATACA | 272 | 418 |
| CTCACGCCACCGCCTACCA | 362 | 419 |
| TCGACTGTGATGACGTGAA | 1836 | 420 |
| TGAACTTCACCACGGACAA | 1851 | 421 |
| CCAAGGCCTGCGTGATCCA | 2103 | 422 |
| GGACTTCACCTCCGAGCAA | 2137 | 423 |
| GACTTCACCTCCGAGCAAA | 2138 | 424 |
| ACTTCACCTCCGAGCAAAT | 2139 | 425 |
| TCGACGAGATCCTGCAGAA | 2157 | 426 |
| CGACGAGATCCTGCAGAAT | 2158 | 427 |
| ACGAGATCCTGCAGAATCA | 2160 | 428 |
| GATCTTCGACAACCTAAAG | 2425 | 429 |
| CCATCTCACTGGCGTACGA | 2580 | 430 |
| CTGCCGAAAGCGACATCAT | 2601 | 431 |
| CGGACAAATTGGTCAATGA | 2646 | 432 |
| CAAATTGGTCAATGAGAGA | 2650 | 433 |
| GGATGACCGCACCGTCAAT | 2794 | 434 |
| CACCGTCAATGACCTGGAA | 2803 | 435 |
| ATCTTCGTCTACGACGAAA | 3116 | 436 |
| CTACGACGAAATCCGCAAA | 3124 | 437 |
| ACGACGAAATCCGCAAACT | 3126 | 438 |
| ACGAAATCCGCAAACTCAT | 3129 | 439 |
| CCAAACCTCTCTCCTCTCT | 3377 | 440 |

| ATP1A4 variant 1 Target Sequence | # of Starting Nucleotide with reference to SEQ ID NO: 127 | SEQ ID NO: |
|---|---|---|
| GGCACCTGGTTACGCTTCA | 113 | 441 |
| CATGGATGATCACAAATTA | 612 | 442 |
| AATCCTGACTCGAGATGGA | 702 | 443 |
| CCTACAGCATCCAGATATA | 833 | 444 |
| CCGGCTTATCTCTGCACAA | 1101 | 445 |
| AGCTCTGATACCTGGTTTA | 1732 | 446 |
| GCTCTGATACCTGGTTTAT | 1733 | 447 |
| AGGTGATGCTTCCGAGTCA | 1836 | 448 |
| GTACTCAATGAACGATGAA | 2070 | 449 |
| TACTCAATGAACGATGAAA | 2071 | 450 |
| GTGCTAGGCTTCTGCTTCT | 2143 | 451 |
| CATGGTAACAGGAGATCAT | 2328 | 452 |
| TGTGGTGCATGGTGCAGAA | 2475 | 453 |
| TGTTCATCATCCTCGGTAT | 2861 | 454 |
| GTTCATCATCCTCGGTATA | 2862 | 455 |
| GGCTTATGAGTCAGCTGAA | 2952 | 456 |
| GGACCTATGAGCAACGAAA | 3203 | 457 |
| CGGATCTCATCATCTCCAA | 3281 | 458 |
| TGGCTGCATTTCTGTCCTA | 3377 | 459 |
| GCTGCATTTCTGTCCTACA | 3379 | 460 |
| GTATTCTCATCTTCGTCTA | 3470 | 461 |
| TATTCTCATCTTCGTCTAT | 3471 | 462 |
| ACTAAACTCAGCAGATGAA | 3554 | 463 |
| GGCCAGAGATTATAAGTTT | 3614 | 464 |
| GCCAGAGATTATAAGTTTG | 3615 | 465 |
| CCAGAGATTATAAGTTTGA | 3616 | 466 |
| CAGAGATTATAAGTTTGAC | 3617 | 467 |
| ATAAGTTTGACACAACATC | 3625 | 468 |

TABLE 4-continued

| ATP1A4 variant 2 Target Sequence | # of Starting Nucleotide with reference to SEQ ID NO: 128 | SEQ ID NO: |
|---|---|---|
| TAAGTTTGACACAACATCT | 3626 | 469 |
| TCTGAGACACTAGGATGAA | 3642 | 470 |
| AGACACTAGGATGAATTAT | 3646 | 471 |
| GACACTAGGATGAATTATC | 3647 | 472 |
| AGGATGAATTATCTTGGAT | 3653 | 473 |
| GATGAATTATCTTGGATGA | 3655 | 474 |
| CGTAGCCAGTCTAGACAGT | 3797 | 475 |
| GCCAGTCTAGACAGTAAAT | 3801 | 476 |
| CAGTCTAGACAGTAAATGT | 3803 | 477 |
| AGACAGTAAATGTCTGGAA | 3809 | 478 |
| GACAGTAAATGTCTGGAAA | 3810 | 479 |

| ATP1A4 variant 2 Target Sequence | # of Starting Nucleotide with reference to SEQ ID NO: 128 | SEQ ID NO: |
|---|---|---|
| GCTGGATTCTTTACCTACT | 126 | 480 |
| GTGGACCTATGAGCAACGA | 251 | 481 |
| TGGACCTATGAGCAACGAA | 252 | 482 |
| GGACCTATGAGCAACGAAA | 253 | 483 |
| CGGATCTCATCATCTCCAA | 331 | 484 |
| TGGCTGCATTTCTGTCCTA | 427 | 485 |
| GCTGCATTTCTGTCCTACA | 429 | 486 |
| GTATTCTCATCTTCGTCTA | 520 | 487 |
| TATTCTCATCTTCGTCTAT | 521 | 488 |
| CTTCGTCTATGATGAAATC | 530 | 489 |
| ACTACTAAACTCAGCAGAT | 601 | 490 |
| CTACTAAACTCAGCAGATG | 602 | 491 |
| TACTAAACTCAGCAGATGA | 603 | 492 |
| ACTAAACTCAGCAGATGAA | 604 | 493 |
| GGCCAGAGATTATAAGTTT | 664 | 494 |
| GCCAGAGATTATAAGTTTG | 665 | 495 |
| CCAGAGATTATAAGTTTGA | 666 | 496 |
| CAGAGATTATAAGTTTGAC | 667 | 497 |
| ATAAGTTTGACACAACATC | 675 | 498 |
| TAAGTTTGACACAACATCT | 676 | 499 |
| TCTGAGACACTAGGATGAA | 692 | 500 |
| AGACACTAGGATGAATTAT | 696 | 501 |
| GACACTAGGATGAATTATC | 697 | 502 |
| TAGGATGAATTATCTTGGA | 702 | 503 |
| AGGATGAATTATCTTGGAT | 703 | 504 |
| GATGAATTATCTTGGATGA | 705 | 505 |
| TGAATTATCTTGGATGAGA | 707 | 506 |
| CGTAGCCAGTCTAGACAGT | 847 | 507 |
| GCCAGTCTAGACAGTAAAT | 851 | 508 |
| CAGTCTAGACAGTAAATGT | 853 | 509 |
| AGACAGTAAATGTCTGGAA | 859 | 510 |
| GACAGTAAATGTCTGGAAA | 860 | 511 |

| ATP1B1 variant 1 Target Sequence | # of Starting Nucleotide with reference to SEQ ID NO: 129 | SEQ ID NO: |
|---|---|---|
| ACCTACTAGTCTTGAACAA | 1096 | 512 |
| TACTAGTCTTGAACAAACT | 1099 | 513 |
| GGACCTACACTTAATCTAT | 1130 | 514 |
| GACCTACACTTAATCTATA | 1131 | 515 |
| CTGCATTTAATAGGTTAGA | 1167 | 516 |
| CGTAACTGACTTGTAGTAA | 1299 | 517 |
| AGCAAGGTTTGCTGTCCAA | 1441 | 518 |
| TGCTGTCCAAGGTGTAAAT | 1450 | 519 |
| GCTGTCCAAGGTGTAAATA | 1451 | 520 |
| CTGTCCAAGGTGTAAATAT | 1452 | 521 |
| TTAACATACTCCATAGTCT | 1564 | 522 |
| GCCTTGTCCTCCGGTATGT | 1746 | 523 |
| TGTCCTCCGGTATGTTCTA | 1750 | 524 |
| GTCCTCCGGTATGTTCTAA | 1751 | 525 |
| TCCTCCGGTATGTTCTAAA | 1752 | 526 |
| CCATCACTTTGGCTAGTGA | 1795 | 527 |

| ATP1B1 variant 1 and variant 2 Common Target Sequences | # of Starting Nucleotide with reference to SEQ ID NO: 129 | SEQ ID NO: |
|---|---|---|
| ACCGGTGGCAGTTGGTTTA | 203 | 528 |
| CCGGTGGCAGTTGGTTTAA | 204 | 529 |
| TTGGTTTAAGATCCTTCTA | 214 | 530 |
| AGATCCTTCTATTCTACGT | 222 | 531 |
| ATCCTTCTATTCTACGTAA | 224 | 532 |
| TCCTTCTATTCTACGTAAT | 225 | 533 |
| CCTTCTATTCTACGTAATA | 226 | 534 |
| GAAATTCCTTTCGTCCTA | 380 | 535 |
| AACGAGGAGACTTTAATCA | 525 | 536 |
| GAAATTGCTCTGGATTAAA | 591 | 537 |
| ATGAAACTTATGGCTACAA | 612 | 538 |

TABLE 4-continued

| | | |
|---|---|---|
| TGAAACTTATGGCTACAAA | 613 | 539 |
| AAACTTATGGCTACAAAGA | 615 | 540 |
| GGCAAACCGTGCATTATTA | 635 | 541 |
| GCAAACCGTGCATTATTAT | 636 | 542 |
| ACCGAGTTCTAGGCTTCAA | 663 | 543 |
| CCGAGTTCTAGGCTTCAAA | 664 | 544 |
| TTCTAGGCTTCAAACCTAA | 669 | 545 |
| ATGAGTCCTTGGAGACTTA | 699 | 546 |
| GCAAGCGAGATGAAGATAA | 765 | 547 |
| AGTTGGAAATGTGGAGTAT | 790 | 548 |
| CTGCAGTATTATCCGTACT | 839 | 549 |
| TGCAGTATTATCCGTACTA | 840 | 550 |
| GCAGTATTATCCGTACTAT | 841 | 551 |
| CCGTACAGTTCACCAATCT | 900 | 552 |
| TCACCAATCTTACCATGGA | 909 | 553 |
| AAATTCGCATAGAGTGTAA | 933 | 554 |
| TGTAAGGCGTACGGTGAGA | 947 | 555 |

| ATP1B1 variant 2 Target Sequence | # of Starting Nucleotide with reference to SEQ ID NO: 130 | SEQ ID NO: |
|---|---|---|
| TGTGTTATGCTTGTATTGA | 1063 | 556 |
| GCCTTGTCCTCCGGTATGT | 1102 | 557 |
| TGTCCTCCGGTATGTTCTA | 1106 | 558 |
| GTCCTCCGGTATGTTCTAA | 1107 | 559 |
| TCCTCCGGTATGTTCTAAA | 1108 | 560 |
| CCTCCGGTATGTTCTAAAG | 1109 | 561 |
| TCCGGTATGTTCTAAAGCT | 1111 | 562 |
| CCATCACTTTGGCTAGTGA | 1151 | 563 |

| ATP1B2 Target Sequence | # of Starting Nucleotide with reference to SEQ ID NO: 131 | SEQ ID NO: |
|---|---|---|
| CCGAGGACGCACCAGTTTA | 653 | 564 |
| CGAGGACGCACCAGTTTAT | 654 | 565 |
| TGCAGACTGTCTCCGACCA | 771 | 566 |
| CAGACTGTCTCCGACCATA | 773 | 567 |
| CAAGACTGAGAACCTTGAT | 841 | 568 |
| AGAACCTTGATGTCATTGT | 849 | 569 |
| CCTTGATGTCATTGTCAAT | 853 | 570 |
| AAGTTCTTGGAGCCTTACA | 917 | 571 |
| AGTTCTTGGAGCCTTACAA | 918 | 572 |

TABLE 4-continued

| | | |
|---|---|---|
| GAGCCTTACAACGACTCTA | 926 | 573 |
| AGCCTTACAACGACTCTAT | 927 | 574 |
| TTACAACGACTCTATCCAA | 931 | 575 |
| GCTATTACGAACAGCCAGA | 981 | 576 |
| TATTACGAACAGCCAGATA | 983 | 577 |
| ATTACGAACAGCCAGATAA | 984 | 578 |
| CAGATAATGGAGTCCTCAA | 996 | 579 |
| GATAATGGAGTCCTCAACT | 998 | 580 |
| AAACGTGCCTGCCAATTCA | 1022 | 581 |
| AACGTGCCTGCCAATTCAA | 1023 | 582 |
| AACCAGAGCATGAATGTTA | 1160 | 583 |
| CTCGGCAACTTCGTCATGT | 1214 | 584 |
| AATGTAGAATGTCGCATCA | 1355 | 585 |
| ATGTAGAATGTCGCATCAA | 1356 | 586 |
| CAACATCGCCACAGACGAT | 1381 | 587 |
| GACGATGAGCGAGACAAGT | 1394 | 588 |
| TGGCCTTCAAACTCCGCAT | 1425 | 589 |
| CCATCTCTCTCCTGTGGAT | 1474 | 590 |
| TTTGATAACAGAGCTATGA | 1550 | 591 |
| CCATTGCGGTTCCGTCACT | 1620 | 592 |
| AGGAGTTAGGAGCCTTTCT | 1707 | 593 |
| TGTGAGAGCTATCCACTCT | 1740 | 594 |
| CACTCTCCTGCCTGCATAT | 1753 | 595 |
| CGCCACACACACACACAAA | 1825 | 596 |
| TCTACACAGTCGCCATCTT | 1956 | 597 |
| TCGCCATCTTGGTGACTTT | 1965 | 598 |
| GGTTGACCTAGGCTGAATA | 2598 | 599 |
| GTTGACCTAGGCTGAATAT | 2599 | 600 |
| GGCTGAATATCCACTTTGT | 2608 | 601 |
| AGCAAGTTATCAACTAATC | 2828 | 602 |
| GCAAGTTATCAACTAATCA | 2829 | 603 |
| CCAAATCTAGCCTCTGAAT | 2888 | 604 |
| CTCCTGCTCTGAATATTCT | 3012 | 605 |
| TGTGTCAGATCTACTGTAA | 3251 | 606 |

| ATP1B3 Target Sequence | # of Starting Nucleotide with reference to SEQ ID NO: 132 | SEQ ID NO: |
|---|---|---|
| TTGCTCTTCTACCTAGTTT | 292 | 607 |
| CAGTGACCGCATTGGAATA | 434 | 608 |

TABLE 4-continued

| | | |
|---|---|---|
| GACCGCATTGGAATATACA | 438 | 609 |
| TTCAGTAGGTCTGATCCAA | 457 | 610 |
| CAGTAGGTCTGATCCAACT | 459 | 611 |
| GGTACATTGAAGACCTTAA | 488 | 612 |
| TACATTGAAGACCTTAAGA | 490 | 613 |
| AGACCTTAAGAAGTTTCTA | 498 | 614 |
| GACCTTAAGAAGTTTCTAA | 499 | 615 |
| GTTTATGTTGCATGTCAGT | 592 | 616 |
| TGGTATGAATGATCCTGAT | 639 | 617 |
| TGAAGGAGTGCCAAGGATA | 723 | 618 |
| TGTAGCAGTTTATCCTCAT | 774 | 619 |
| GTAGCAGTTTATCCTCATA | 775 | 620 |
| CTCATAATGGAATGATAGA | 788 | 621 |
| AGCCATTGGTTGCTGTTCA | 857 | 622 |
| GCCATTGGTTGCTGTTCAG | 858 | 623 |
| GTAACAGTTGAGTGCAAGA | 910 | 624 |
| TAACAGTTGAGTGCAAGAT | 911 | 625 |
| TGATGGATCAGCCAACCTA | 930 | 626 |
| GATGGATCAGCCAACCTAA | 931 | 627 |
| ATGGATCAGCCAACCTAAA | 932 | 628 |
| GCATAGTATGAGTAGGATA | 1009 | 629 |
| CATAGTATGAGTAGGATAT | 1010 | 630 |
| GGATATCTCCACAGAGTAA | 1023 | 631 |
| GATATCTCCACAGAGTAAA | 1024 | 632 |
| AGAAAGGTGTGTGGTACAT | 1111 | 633 |
| ATAACGTGCTTCCAGATCA | 1146 | 634 |
| TAACGTGCTTCCAGATCAT | 1147 | 635 |
| AGTGTACAGTCGCCAGATA | 1220 | 636 |
| GTGAACACCTGATTCCAAA | 1246 | 637 |
| AGCTTAATATGCCGTGCTA | 1321 | 638 |
| TAATATGCCGTGCTATGTA | 1325 | 639 |
| AATATGCCGTGCTATGTAA | 1326 | 640 |
| ATATGCCGTGCTATGTAAA | 1327 | 641 |
| GCCGTGCTATGTAAATATT | 1331 | 642 |
| TGCAAGAAATGTGGTATGT | 1437 | 643 |
| ATGCTGAATTAGCCTCGAT | 1548 | 644 |
| TTGATTAAGAGCACAAACT | 1571 | 645 |
| AGCAGACTGTGGACTGTAA | 1785 | 646 |

TABLE 4-continued

| | | |
|---|---|---|
| GCAGACTGTGGACTGTAAT | 1786 | 647 |
| CAGACTGTGGACTGTAATA | 1787 | 648 |

Table 5 lists examples of siRNA target sequences within the SLC12A1 and SLC12A2 DNA sequences (SEQ ID NO:7 and SEQ ID NO:133, respectively) from which siRNAs of the present invention are designed in a manner as set forth above. As noted above, SLC12A1 and SLC12A2 encode the Na—K-2Cl cotransporter, NKCC2 and NKCC1, respectively.

TABLE 5

SLC12A1 Target Sequences for siRNAs

| SLC12A1 Target Sequence | # of Starting Nucleotide with reference to SEQ ID NO: 7 | SEQ ID NO: |
|---|---|---|
| CCACCATAGTAACGACAAT | 675 | 73 |
| GGAATGGAATGGGAGGCAA | 974 | 74 |
| GGGATGAACTGCAATGGTT | 1373 | 75 |
| CCATGCCTCTTATGCCAAA | 1780 | 76 |
| CCTGCTCTCCTGGACATAA | 2102 | 77 |
| GCATCTGCTGTGAAGTCTT | 2151 | 78 |
| GCCTCAGGCTTAGGAAGAA | 2315 | 79 |
| GGAAGCGACTATCAAAGAT | 2542 | 80 |
| GCTGGCAAGTTGAACATTA | 2609 | 81 |
| GCAAGAAAGGGATCCATAT | 3197 | 82 |
| TAATACCAATCGCTTTCAA | 67 | 649 |
| ACCAATCGCTTTCAAGTTA | 71 | 650 |
| CAATCGCTTTCAAGTTAGT | 73 | 651 |
| ATAGAGTACTATCGTAACA | 353 | 652 |
| CCAGCCTGCTTGAGATTCA | 405 | 653 |
| CTGTAGTAGATCTACTTAA | 864 | 654 |
| ACCAATGACATCCGGATTA | 911 | 655 |
| CCAATGACATCCGGATTAT | 912 | 656 |
| CAATGACATCCGGATTATA | 913 | 657 |
| GGCTATGACTTCTCAAGAT | 1409 | 658 |
| GCCTCATATGCACTTATTA | 1748 | 659 |
| AGACCTGCGTATGGAATTT | 1811 | 660 |
| ACGTCTATGTGACTTGTAA | 1935 | 661 |
| GTCTATGTGACTTGTAAGA | 1937 | 662 |
| TTCCTACGTGAGTGCTTTA | 1993 | 663 |
| GACAATGCTCTGGAATTAA | 2012 | 664 |
| CTCTGGTGATTGGATATAA | 2346 | 665 |
| TGACAGAGATTGAGAACTA | 2388 | 666 |

TABLE 5-continued

| | # of Starting Nucleotide with reference to SEQ ID NO: 133 | SEQ ID NO: |
|---|---|---|
| TGAGATTGGCGTGGTTATA | 2437 | 667 |
| GCATCCGAGGCTTGTTTAA | 2586 | 668 |
| ACCATATCGTCTCCATGAA | 3007 | 669 |
| CCATATCGTCTCCATGAAA | 3008 | 670 |
| TGAAAGCTGCAAAGATTTA | 3022 | 671 |
| TCGACTGAATGAACTCTTA | 3130 | 672 |
| CCATATCGGATTTGTTGTA | 3210 | 673 |
| GGTTGGAAATCCTCACAAA | 3237 | 674 |
| CTTACTAGTTAGAGGAAAT | 3271 | 675 |

| SLC12A2 Target Sequence | # of Starting Nucleotide with reference to SEQ ID NO: 133 | SEQ ID NO: |
|---|---|---|
| ACCACCAGCACTACTATTA | 748 | 676 |
| CCACCAGCACTACTATTAT | 749 | 677 |
| CAGCACTACTATTATGATA | 753 | 678 |
| CTATCAGTCCTTGTAATAA | 1119 | 679 |
| ATTGTCTACTTCAGCAATA | 1169 | 680 |
| TATTGGTGATTTCGTCATA | 1499 | 681 |
| TTCGTCATAGGAACATTTA | 1509 | 682 |
| TAATGACACTATCGTAACA | 1820 | 683 |
| GATGTTTGCTAAAGGTTAT | 2081 | 684 |
| CTTCGTGGCTACATCTTAA | 2118 | 685 |
| TGCACTTGGATTCATCTTA | 2147 | 686 |
| GATGATCTGTGGCCATGTA | 2615 | 687 |
| CTCGAAGACAAGCCATGAA | 2644 | 688 |
| TGAAAGAGATGTCCATCGA | 2659 | 689 |
| AGAGATGTCCATCGATCAA | 2663 | 690 |
| CCATCGATCAAGCCAAATA | 2671 | 691 |
| CATCGATCAAGCCAAATAT | 2672 | 692 |
| GGTCGTATGAAGCCAAACA | 2793 | 693 |
| CACTTGTCCTTGGATTTAA | 2812 | 694 |
| TAGTGGTTATTCGCCTAAA | 2914 | 695 |
| ATCTCATCTTCAAGGACAA | 2948 | 696 |
| CGATTTAGATACTTCCAAA | 3044 | 697 |
| TCATTGGTGGAAAGATAAA | 3334 | 698 |
| TTAGCAAGTTCCGGATAGA | 3391 | 699 |
| GAAATCATTGAGCCATACA | 3480 | 700 |
| AGCAAGATATTGCAGATAA | 3520 | 701 |
| GATGAACCATGGCGAATAA | 3549 | 702 |
| CATTCAAGCACAGCTAATA | 3639 | 703 |
| TTCAGTGCCTAGTGTAGTA | 3840 | 704 |
| AGGAAAGTTGCTCCATTGA | 3941 | 705 |
| AAAGTTGCTCCATTGATAA | 3944 | 706 |
| CAATCTTAATGGTGATTCT | 4001 | 707 |
| TTGACATCATAGTCTAGTA | 4995 | 708 |
| GACATCATAGTCTAGTAAA | 4997 | 709 |
| GTGTGTGTGTGTGTATATA | 5141 | 710 |
| GTGTGTGTGTGTATATATA | 5143 | 711 |
| TAGGCAAACTTTGGTTTAA | 5249 | 712 |
| GGAGAATACTTCGCCTAAA | 5375 | 713 |
| TGAGTATGACCTAGGTATA | 5834 | 714 |
| AGAGATCTGATAACTTGAA | 5852 | 715 |
| GGTAAAGACAGTAGAAATA | 5981 | 716 |
| TTTAAGCTCTGGTGGATGA | 6678 | 717 |

As cited in the examples above, one of skill in the art is able to use the target sequence information provided in Tables 1-5 to design interfering RNAs having a length shorter or longer than the sequences provided in Table 1-5 by referring to the sequence position in SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, and adding or deleting nucleotides complementary or near complementary to SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, respectively.

The target RNA cleavage reaction guided by siRNAs and other forms of interfering RNA is highly sequence specific. In general, siRNA containing a sense nucleotide strand identical in sequence to a portion of the target mRNA and an antisense nucleotide strand exactly complementary to a portion of the target mRNA are siRNA embodiments for inhibition of mRNAs cited herein. However, 100% sequence complementarity between the antisense siRNA strand and the target mRNA, or between the antisense siRNA strand and the sense siRNA strand, is not required to practice the present invention. Thus, for example, the invention allows for sequence variations that might be expected due to genetic mutation, strain polymorphism, or evolutionary divergence.

In one embodiment of the invention, the antisense strand of the siRNA has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical" to at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

The relationship between a target mRNA (sense strand) and one strand of an siRNA (the sense strand) is that of identity. The sense strand of an siRNA is also called a passenger strand, if present. The relationship between a target mRNA (sense strand) and the other strand of an siRNA (the antisense strand) is that of complementarity. The antisense strand of an siRNA is also called a guide strand.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

The phrase "a region of at least 13 contiguous nucleotides having at least 90% sequence complementarity to, or at least 90% sequence identity with, the penultimate 13 nucleotides of the 3' end of any one of (a sequence identifier)" allows a one nucleotide substitution. Two nucleotide substitutions (i.e., 11/13=85% identity/complementarity) are not included in such a phrase.

In one embodiment of the invention, the region of contiguous nucleotides is a region of at least 14 contiguous nucleotides having at least 85% sequence complementarity to, or at least 85% sequence identity with, the penultimate 14 nucleotides of the 3' end of the sequence identified by each sequence identifier. Two nucleotide substitutions (i.e., 12/14=86% identity/complementarity) are included in such a phrase.

In a further embodiment of the invention, the region of contiguous nucleotides is a region of at least 15, 16, 17, or 18 contiguous nucleotides having at least 80% sequence complementarity to, or at least 80% sequence identity with, the penultimate 14 nucleotides of the 3' end of the sequence of the sequence identifier. Three nucleotide substitutions are included in such a phrase.

The target sequence in the mRNAs corresponding to SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, may be in the 5' or 3' untranslated regions of the mRNA as well as in the coding region of the mRNA.

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single molecule where the regions of complementarity are base-paired and are covalently linked by a hairpin loop so as to form a single strand. It is believed that the hairpin is cleaved intracellularly by a protein termed dicer to form an interfering RNA of two individual base-paired RNA molecules.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

There may be a region or regions of the antisense interfering RNA strand that is (are) not complementary to a portion of SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134. Non-complementary regions may be at the 3', 5' or both ends of a complementary region or between two complementary regions.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.).

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

Hybridization under Physiological Conditions: In certain embodiments of the present invention, an antisense strand of an interfering RNA hybridizes with an mRNA in vivo as part of the RISC complex.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning. A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m$ °C.=81.5+16.6($\log_{10}$[Na+])+0.41 (% G+C)−(600/N) where N is the number of bases in the hybrid, and [Na+] is the concentration of sodium ions in the hybridization buffer.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Single-stranded interfering RNA: As cited above, interfering RNAs ultimately function as single strands. Single-stranded (ss) interfering RNA has been found to effect mRNA silencing, albeit less efficiently than double-stranded RNA. Therefore, embodiments of the present invention also provide for administration of a ss interfering RNA that hybridizes under physiological conditions to a portion of SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, and has a region of at least near-perfect contiguous complementarity of at least 19 nucleotides with the hybridizing portion of SEQ ID NO:1, SEQ ID NO:2, SEQ ID NO:3, SEQ ID NO:4, SEQ ID NO:5, SEQ ID NO:6, SEQ ID NO:7, SEQ ID NO:101, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, or SEQ ID NO:134, respectively. The ss interfering RNA has a length of 19 to 49 nucleotides as for the ds interfering RNA cited above. The ss interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

SS interfering RNAs are synthesized chemically or by in vitro transcription or expressed endogenously from vectors or expression cassettes as for ds interfering RNAs. 5' Phosphate groups may be added via a kinase, or a 5' phosphate may be the result of nuclease cleavage of an RNA. Delivery is as for ds interfering RNAs. In one embodiment, ss interfering RNAs having protected ends and nuclease resistant modifications are administered for silencing. SS interfering RNAs may be dried for storage or dissolved in an aqueous solution. The solution may contain buffers or salts to inhibit annealing or for stabilization.

Hairpin interfering RNA: A hairpin interfering RNA is a single molecule (e.g., a single oligonucleotide chain) that comprises both the sense and antisense strands of an interfering RNA in a stem-loop or hairpin structure (e.g., a shRNA).

For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Mode of administration: Interfering RNA may be delivered directly to the eye by ocular tissue injection such as periocular, conjunctival, subtenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or within the eye. Intracameral injection may be through the cornea into the anterior chamber to allow the agent to reach the trabecular meshwork. Intracanalicular injection may be into the venous collector channels draining Schlemm's canal or into Schlemm's canal. Systemic or parenteral administration is contemplated including but not limited to intravenous, subcutaneous, and oral delivery.

Subject: A subject in need of treatment for ocular hypertension or at risk for developing ocular hypertension is a human or other mammal having ocular hypertension or at risk of having ocular hypertension associated with undesired or inappropriate expression or activity of targets as cited herein, i.e., carbonic anhydrase II, IV, or XII; β1- or β2-adrenergic receptors; acetylcholinesterase; Na$^+$/K$^+$-ATPase; or Na—K-2Cl cotransporter. Ocular structures associated with such disorders may include the eye, retina, choroid, lens, cornea, trabecular meshwork, iris, optic nerve, optic nerve head, sclera, aqueous chamber, vitreous chamber, or ciliary body, for example. A subject may also be an ocular cell, cell culture, organ or an ex vivo organ or tissue.

Formulations and Dosage: Pharmaceutical formulations comprise an interfering RNA, or salt thereof, of the invention up to 99% by weight mixed with a physiologically acceptable ophthalmic carrier medium such as water, buffer, saline, glycine, hyaluronic acid, mannitol, and the like.

Interfering RNAs of the present invention are administered as solutions, suspensions, or emulsions. The following are examples of possible formulations embodied by this invention.

| | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |

-continued

| | Amount in weight % |
|---|---|
| Cremophor EL | 0.1 |
| Benzalkonium chloride | 0.01 |
| HCl and/or NaOH | pH 7.3-7.4 |
| Purified water (RNase-free) | q.s. to 100% |
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

Generally, an effective amount of the interfering RNA of embodiments of the invention results in an extracellular concentration at the surface of the target cell of from 100 pM to 100 nM, or from 1 nM to 50 nM, or from 5 nM to about 10 nM, or to about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions are delivered to the surface of the eye one to four times per day, or on an extended delivery schedule such as daily, weekly, bi-weekly, monthly, or longer, according to the routine discretion of a skilled clinician. The pH of the formulation is about pH 4-9, or pH 4.5 to pH 7.4.

Therapeutic treatment of patients with siRNAs directed against the ocular hypertension target mRNAs is expected to be beneficial over small molecule topical ocular drops by increasing the duration of action, thereby allowing less frequent dosing and greater patient compliance.

While the precise regimen is left to the discretion of the clinician, interfering RNA may be administered by placing one drop in each eye as directed by the clinician. An effective amount of a formulation may depend on factors such as the age, race, and sex of the subject, the severity of the ocular hypertension, the rate of target gene transcript/protein turnover, the interfering RNA potency, and the interfering RNA stability, for example. In one embodiment, the interfering RNA is delivered topically to the eye and reaches the trabecular meshwork, retina or optic nerve head at a therapeutic dose thereby ameliorating an ocular hypertension-associated disease process.

Acceptable carriers: An ophthalmically acceptable carrier refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (Mirus Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); or liposomes. Liposomes are formed from standard vesicle-forming lipids and a sterol, such as cholesterol, and may include a targeting molecule such as a monoclonal antibody having binding affinity for endothelial cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone, as components of covalent conjugates, complexed with cationic lipids, cationic peptides, or cationic polymers, or encapsulated in targeted or non-targeted nanoparticles.

For ophthalmic delivery, an interfering RNA may be combined with ophthalmologically acceptable preservatives, co-solvents, surfactants, viscosity enhancers, penetration enhancers, buffers, sodium chloride, or water to form an aqueous, sterile ophthalmic suspension or solution. Ophthalmic solution formulations may be prepared by dissolving the interfering RNA in a physiologically acceptable isotonic aqueous buffer. Further, the ophthalmic solution may include an ophthalmologically acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art for other ophthalmic formulations. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

Kits: Embodiments of the present invention provide a kit that includes reagents for attenuating the expression of an mRNA as cited herein in a cell. The kit contains an siRNA or an shRNA expression vector. For siRNAs and non-viral shRNA expression vectors the kit also may contain a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an ophthalmically acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The ability of interfering RNA to knock-down the levels of endogenous target gene expression in, for example, human trabecular meshwork (TM) cells is evaluated in vitro as follows. Transformed human TM cells, for example, cell lines designated GTM-3 or HTM-3 (see Pang, I. H. et al.,. 1994. *Curr. Eye Res.* 13:51-63), are plated 24 h prior to transfection in standard growth medium (e.g., DMEM supplemented with 10% fetal bovine serum). Transfection is performed using Dharmafect 1 (Dharmacon, Lafayette, Colo.) according to the manufacturer's instructions at interfering RNA concentrations ranging from 0.1 nM-100 nM. Non-targeting control interfering RNA and lamin A/C interfering RNA (Dharmacon) are used as controls. Target mRNA levels are assessed by qPCR 24 h post-transfection using, for example, TAQMAN® forward and reverse primers and a probe set that encompasses the target site (Applied Biosystems, Foster City, Calif.). Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA should be used that will produce the desired level of knock-down in target gene expression.

The ability of interfering RNAs of the present invention to knock-down levels of CA2 protein expression is further exemplified in Example 1 as follows.

EXAMPLE 1

Interfering RNA for Specifically Silencing CA2 in HeLa Cells

The present study examines the ability of CA2-interfering RNA to knock down the levels of endogenous CA2 expression in cultured HeLa cells.

Transfection of HeLa cells was accomplished using standard in vitro concentrations (100 nM and 1 nM) of CA2 siRNAs, or a non-targeting control siRNA and DharmaFECT™ 1 transfection reagent (Dharmacon, Lafayette, Colo.). All siRNAs were dissolved in 1× siRNA buffer, an aqueous solution of 20 mM KCl, 6 mM HEPES (pH 7.5), 0.2 mM $MgCl_2$. CA2 protein expression and actin protein expression (loading control) was evaluated by western blot analysis 72 hours post-transfection. The CA2 siRNAs are double-stranded interfering RNAs having specificity for the following target sequences: siCA2#1 targets SEQ ID NO:721; siCA2#3 targets SEQ ID NO:15; siCA2#4 targets SEQ ID NO:720; siCA2#5 targets SEQ ID NO:141. Each of the four CA2 siRNAs decreased CA2 expression significantly at both 100 nM and 1 nM relative to a non-targeting control siRNA as shown by the western blot data of FIG. 1. SiCA2#4 targeting SEQ ID NO:720 and siCA2#5 targeting SEQ ID NO:141 appeared to be particularly effective.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. A method of attenuating expression of an ocular hypertension target mRNA in a subject wherein the ocular hypertension is treated, the method comprising:
administering to the subject a composition comprising an effective amount of interfering RNA having a length of 19 to 49 nucleotides and a pharmaceutically acceptable carrier, the interfering RNA comprising:
a region of at least 13 contiguous nucleotides having at least 90% sequence complementarity to, or at least 90% sequence identity with, the penultimate 13 nucleotides of the 3' end of SEQ ID NO: 140 or SEQ ID NO: 720.

2. The method of claim 1 wherein the region of contiguous nucleotides is a region of at least 14 contiguous nucleotides having at least 85% sequence complementarity to, or at least 85% sequence identity with, the penultimate 14 nucleotides of the 3' end of the sequence of the sequence identifier.

3. The method of claim 1 wherein the region of contiguous nucleotides is a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of the sequence of the sequence identifier.

4. The method of claim 1 wherein the interfering RNA is an shRNA.

5. The method of claim 1 wherein the composition is administered via a topical, intravitreal, transcleral, periocular, conjunctival, subtenon, intracameral, subretinal, subconjunctival, retrobulbar, or intracanalicular route.

6. The method of claim 1 wherein the composition is administered via in vivo expression from an expression vector capable of expressing the interfering RNA.

7. The method of claim 1 wherein the interfering RNA is an siRNA.

8. A method of treating ocular hypertension in a subject in need thereof, the method comprising:
administering to an eye of the subject a composition comprising an effective amount of interfering RNA having a length of 19 to 49 nucleotides and a pharmaceutically acceptable carrier, the interfering RNA comprising:
a region of at least 13 contiguous nucleotides having at least 90% sequence complementarity to, or at least 90% sequence identity with, the penultimate 13 nucleotides of the 3' end of SEQ ID NO: 140 or SEQ ID NO: 720,
wherein the ocular hypertension is treated thereby.

9. The method of claim 8 wherein the interfering RNA is an shRNA.

10. The method of claim 8 wherein the composition is administered via a topical, intravitreal, transcleral, periocular, conjunctival, subtenon, intracameral, subretinal, subconjunctival, retrobulbar, or intracanalicular route.

11. The method of claim 8 wherein the composition is administered via in vivo expression from an expression vector capable of expressing the interfering RNA.

12. The method of claim 8 wherein the interfering RNA is an siRNA.

13. A method of attenuating expression of an ocular hypertension target mRNA of a subject, comprising:
administering to the subject a composition comprising an effective amount of interfering RNA having a length of 19 to 49 nucleotides and a pharmaceutically acceptable carrier, the interfering RNA comprising:
a sense nucleotide strand, an antisense nucleotide strand, and a region of at least near-perfect contiguous complementarity of at least 19 nucleotides;
wherein the antisense strand hybridizes under physiological conditions to a portion of mRNA corresponding to SEQ ID NO:1, and has a region of at least near-perfect contiguous complementarity of at least 19 nucleotides with the hybridizing portion of mRNA corresponding to SEQ ID NO:1, wherein the antisense strand is designed to target an mRNA corresponding to SEQ ID NO:1 comprising nucleotide 317 or 318, wherein the expression of an ocular hypertension target mRNA is attenuated.

14. The method of claim 13 wherein the subject is a human and the human has ocular hypertension.

15. The method of claim 13 wherein the subject is a human and the human is at risk of developing ocular hypertension.

16. The method of claim 13 further comprising administering to the subject a second interfering RNA having a length of 19 to 49 nucleotides, and comprising a sense nucleotide strand, an antisense nucleotide strand, and a region of at least near-perfect complementarity of at least 19 nucleotides;

wherein the antisense strand of the second interfering RNA hybridizes under physiological conditions to a second portion of mRNA corresponding to SEQ ID NO:1, and the antisense strand has a region of at least near-perfect contiguous complementarity of at least 19 nucleotides with the second hybridizing portion of mRNA corresponding to SEQ ID NO:1.

17. The method of claim 13 wherein the sense nucleotide strand and the antisense nucleotide strand are connected by a loop nucleotide sequence.

18. The method of claim 14 wherein the composition is administered via a topical, intravitreal, transcleral, periocular, conjunctival, subtenon, intracameral, subretinal, subconjunctival, retrobulbar, or intracanalicular route.

19. The method of claim 15 wherein the composition is administered via a topical, intravitreal, transcleral, periocular, conjunctival, subtenon, intracameral, subretinal, subconjunctival, retrobulbar, or intracanalicular route.

20. The method of claim 13 wherein the composition is administered via in vivo expression from an expression vector capable of expressing the interfering RNA.

21. The method of claim 14 wherein the composition is administered via in vivo expression from an expression vector capable of expressing the interfering RNA.

22. The method of claim 15 wherein the composition is administered via in vivo expression from an expression vector capable of expressing the interfering RNA.

23. A method of treating ocular hypertension in a subject in need thereof comprising:

administering to an eye of the subject a composition comprising an effective amount of interfering RNA having a length of 19 to 49 nucleotides and a pharmaceutically acceptable carrier, the interfering RNA comprising:

a sense nucleotide strand, an antisense nucleotide strand, and a region of at least near-perfect contiguous complementarity of at least 19 nucleotides;

wherein the antisense strand hybridizes under physiological conditions to a portion of mRNA corresponding to SEQ ID NO:1, and has a region of at least near-perfect contiguous complementarity of at least 19 nucleotides with the hybridizing portion of mRNA corresponding to SEQ ID NO:1, wherein the antisense strand is designed to target an mRNA corresponding to SEQ ID NO:1 comprising nucleotide 317 or 318, wherein the ocular hypertension is treated thereby.

24. The method of claim 23 wherein the subject is a human.

25. The method of claim 23 further comprising administering to the subject a second interfering RNA having a length of 19 to 49 nucleotides, and comprising a sense nucleotide strand, an antisense nucleotide strand, and a region of at least near-perfect complementarity of at least 19 nucleotides;

wherein the antisense strand of the second interfering RNA hybridizes under physiological conditions to a second portion of mRNA corresponding to SEQ ID NO:1, and the antisense strand has a region of at least near-perfect contiguous complementarity of at least 19 nucleotides with the second hybridizing portion of mRNA corresponding to SEQ ID NO:1.

26. The method of claim 23 wherein the sense nucleotide strand and the antisense nucleotide strand are connected by a loop nucleotide sequence.

27. The method of claim 23 wherein the composition is administered via a topical, intravitreal, transcleral, periocular, conjunctival, subtenon, intracameral, subretinal, subconjunctival, retrobulbar, or intracanalicular route.

28. The method of claim 24 wherein the composition is administered via a topical, intravitreal, transcleral, periocular, conjunctival, subtenon, intracameral, subretinal, subconjunctival, retrobulbar, or intracanalicular route.

29. The method of claim 23 wherein the composition is administered via in vivo expression from an expression vector capable of expressing the interfering RNA.

30. The method of claim 24 wherein the composition is administered via in vivo expression from an expression vector capable of expressing the interfering RNA.

31. A method of attenuating expression of an ocular hypertension target mRNA of a subject, comprising:

administering to the subject a composition comprising an effective amount of single-stranded interfering RNA having a length of 19 to 49 nucleotides and a pharmaceutically acceptable carrier, wherein the single-stranded interfering RNA hybridizes under physiological conditions to a portion of mRNA corresponding to SEQ ID NO:1 comprising nucleotide 317 or 318, and the interfering RNA has a region of at least near-perfect contiguous complementarity with the hybridizing portion of mRNA corresponding to SEQ ID NO:1;

wherein the expression of an ocular hypertension target mRNA is thereby attenuated.

32. The method of claim 31 wherein the composition is administered via a topical, intravitreal, transcleral, periocular, conjunctival, subtenon, intracameral, subretinal, subconjunctival, retrobulbar, or intracanalicular route.

33. The method of claim 31 wherein the composition is administered via in vivo expression from an expression vector capable of expressing the interfering RNA.

34. The method of claim 31 wherein the interfering RNA is an siRNA.

35. A composition comprising interfering RNA having a length of 19 to 49 nucleotides and having a nucleotide sequence of SEQ ID NO: 140 or SEQ ID NO: 720, or a complement thereof, and a pharmaceutically acceptable carrier.

36. The composition of claim 35 wherein the interfering RNA is an shRNA.

37. The composition of claim 35 wherein the interfering RNA is an siRNA.

* * * * *

UNITED STATES PATENT AND TRADEMARK OFFICE
CERTIFICATE OF CORRECTION

PATENT NO. : 7,592,324 B2  Page 1 of 1
APPLICATION NO. : 11/345361
DATED : September 22, 2009
INVENTOR(S) : Shepard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 398 days.

Signed and Sealed this

Twenty-first Day of September, 2010

David J. Kappos
*Director of the United States Patent and Trademark Office*